US007884202B2

(12) United States Patent
Yamakawa et al.

(10) Patent No.: US 7,884,202 B2
(45) Date of Patent: Feb. 8, 2011

(54) NUCLEOBASE HAVING PERFLUOROALKYL GROUP AND PROCESS FOR PRODUCING THE SAME

(75) Inventors: Tetsu Yamakawa, Nishitokyo (JP); Kyoko Yamamoto, Odawara (JP); Daisuke Uraguchi, Nagoya (JP); Kenji Tokuhisa, Shunan (JP)

(73) Assignees: Tosoh Corporation, Shunan-shi, Yamaguchi-ken (JP); Tosoh F-Tech, Inc., Shunan-shi, Yamaguchi (JP); Sagami Chemical Research Center, Ayase-shi, Kanagawa (JP)

( * ) Notice: Subject to any disclaimer, the term of this patent is extended or adjusted under 35 U.S.C. 154(b) by 342 days.

(21) Appl. No.: 12/083,780

(22) PCT Filed: Nov. 6, 2006

(86) PCT No.: PCT/JP2006/322094

§ 371 (c)(1),
(2), (4) Date: Apr. 18, 2008

(87) PCT Pub. No.: WO2007/055170

PCT Pub. Date: May 18, 2007

(65) Prior Publication Data

US 2009/0124796 A1 May 14, 2009

(30) Foreign Application Priority Data

Nov. 9, 2005 (JP) .............................. 2005-324943

(51) Int. Cl.
C07H 19/04 (2006.01)
C07D 473/00 (2006.01)
C07D 239/02 (2006.01)

(52) U.S. Cl. .................... 536/27.11; 544/265; 544/267; 544/276; 544/277; 544/309; 544/312; 544/317

(58) Field of Classification Search ....................... None
See application file for complete search history.

(56) References Cited

U.S. PATENT DOCUMENTS 3,900,474 A 8/1975 Ginger et al.
5,352,787 A 10/1994 Andres et al.

FOREIGN PATENT DOCUMENTS

| JP | 55-66583 | 5/1980 |
| JP | 58-152857 | 9/1983 |
| JP | 61-257977 | 11/1986 |
| JP | 4-149193 | 5/1992 |
| JP | 4-503814 | 7/1992 |
| JP | 4-261161 | 9/1992 |
| JP | 5-1066 | 1/1993 |
| JP | 5-508647 | 12/1993 |
| JP | 6-73023 | 3/1994 |
| JP | 11-246590 | 9/1999 |
| JP | 2001-247551 | 9/2001 |
| WO | WO 2005/054191 A1 | 6/2005 |
| WO | 2006/045565 | 5/2006 |
| WO | WO 2008/056677 | 5/2008 |

OTHER PUBLICATIONS

Kobayashi et al., Studies on Organic Fluorine Compounds. Part 35. Trifluoromethylation of Pyrimidine- and Purine-nucleosides with Trifluoromethyl-copper Complex, J. Chem. Soc., Perkin Tr. I, 1980, pp. 2755-2761.*
Medebielle et al., "A Convenient Synthesis of Perfluoroalkylated and Fluorinated-Aryl Nitrogen Bases by Electrochemically Induced SRN1 Substitution", *The Journal of Organic Chemistry*, vol. 61, No. 4, 1996, pp. 1331-1340.
Jacobson et al., "Effect of Trifluoromethyl and Other Substituents on Activity of Xanthines at Adenosine Receptors", *Journal of Medicinal Chemistry*, vol. 36, No. 18, 1993, pp. 2639-2644.
Medebielle et al., An Electrochemical Approach for the Synthesis of Perfluoroalkylated Purine and Indole Angalogues of Plant Growth Regulators, *Tetrahedron*, vol. 56, No. 17, 2000, pp. 2655-2664.
Baciocchi et al., "Synthesis of Perfluoroalkylpyrroles by Homolytic Substitution with Perfluoroalkyl Radicals", *Tetrahedron Letters*, vol. 34, No. 23, 1993, pp. 3799-3800.
Bravo et al., "New Methods of Free-Radical Perfluoroalkylation of Aromatics and Alkenes. Absolute Rate Constants and Partial Rate Factors for the Homolytic Aromatic Substitution by n-Perfluorobutyl Radical", *The Journal of Organic Chemistry*, vol. 62, No. 21, 1997, pp. 7128-7136.
International Search Report for PCT/JP2006/322094 mailed Dec. 12, 2006.
Tanabe et al, "Direct Perfluoroalkylation Including . . . ", Journal of Organic Chemistry, vol. 53, pp. 4582-4585, 1988.
Diringer et al, "Fluorinated Pyrimidines. XXXVI. Synthesis . . . ", Journal of Medicinal Chemistry, vol. 13, pp. 151-152, 1970.
Giner-Sorolla et al, "Fluorine-containing Pyrimidines and Purines: . . . ", Journal of the American Chemical Society, vol. 80, pp. 5744-5752, 1958.
Pfleiderer et al, "Synthese und Eigenschaften . . . ", Justus Libigs Annalen der Chemie, vol. 726, pp. 201-215, 1969.
Medebielle et al, "Perfluoroalkylation of Purine . . . ", Tetrahedron Letters, vol. 33, pp. 7351-7354, 1992.
Kramer et al, "Selective Inhibition of Cyclic Nucleotide Phosphodiesterases by Analogues of 1-Methyl-3-isobutylxanthine", Biochemistry, vol. 16, No. 15, 1977; XP-002169138, pp. 3316-3321.
Khanna et al, "1,2-Diarylpyrroles as Potent and Selective Inhibitors of Cyclooxygenase-2", J. Med. Chem., 1997, 40, 1619-1633.
Hall et al, "Structure-activity relationships of 1,5-biaryl pyrroles as $EP_1$ receptor antagonists", Bioorganic & Medicinal Chemistry Letters, 16 (2006), 3657-3662.

* cited by examiner

*Primary Examiner*—Lawrence E Crane
(74) *Attorney, Agent, or Firm*—Nixon & Vanderhye P.C.

(57) ABSTRACT

Nucleobases are perfluoroalkylated in a one step process with a perfluoroalkyl halide in the presence of a sulfoxide, a peroxide and an iron compound. Compounds so produced are useful as medicinal drugs, intermediates for medicinal drugs and agricultural chemicals.

15 Claims, No Drawings

NUCLEOBASE HAVING PERFLUOROALKYL GROUP AND PROCESS FOR PRODUCING THE SAME

This application is the U.S. national phase of International Application No. PCT/JP2006/322094 filed 6 Nov. 2006 which designated the U.S. and claims priority to Japanese Application No. 2005-324943 filed 9 Nov. 2005, the entire contents of each of which are hereby incorporated by reference.

TECHNICAL FIELD

The present invention relates to a process for producing a nucleobase having a perfluoroalkyl group.

BACKGROUND ART

Nucleobases substituted by a perfluoroalkyl group are important compounds as medical drugs and intermediates for medical and agricultural chemicals, and nucleobases having a trifluoromethyl group are particularly useful compounds. Therefore, many studies have been conducted on processes for producing the trifluoromethyl-substituted nucleobases.

With respect to a method for producing 5-trifluoromethyl uracil which is important as an intermediate for an anticancer agent, an antiviral agent, or the like, for example, Patent Document 1 discloses a method for producing 5-trifluoromethyl uracil by reacting 5-trifluoromethyl-5,6-dihydrouracil which is obtained by a reaction of $\alpha$-trifluoromethyl acrylic acid and urea, with dimethyl sulfoxide and iodine in the presence of concentrated sulfuric acid as a catalyst. Furthermore, Patent Document 2 discloses a method of reacting 5-iodouracils with copper iodide and methyl fluorosulfonyldifluoroacetate to convert them to a 5-trifluoromethyluracils. Moreover, Patent Document 3 discloses a method for producing 5-trifluoromethyluracil, in which thymine is chlorinated with a chlorine gas to form 2,4-dichloro-5-trichloromethylpyrimidine, and then fluorinated with anhydrous hydrofluoric acid or antimony trifluoride in the coexistence with antimony pentachloride, followed by a treatment with water.

However, these methods have problems that all the methods include multi-steps and the last method uses anhydrous hydrofluoric acid and the antimony compound which are industrially hard to handle. Moreover, Non-patent Document 1 discloses a method for trifluoromethylating 3',5'-diacetyl-2'-deoxyuridine at the 5-position with trifluoroacetic acid and xenon difluoride. However, this method also uses a special reagent and is industrially hard to employ.

Furthermore, with respect to a method for producing 5-trifluoromethylcytosine, Non-patent Document 2 discloses a method for producing 5-trifluoromethylcytosine by hydrolyzing 4-amino-2-chloro-5-trifluoromethylpyrimidine obtained by a reaction of 2,4-dichloro-5-trifluoromethylpyrimidine and liquid ammonia, and treating it with an ion-exchange resin. However, this method has a problem of multi-steps including production of raw materials.

With respect to a method for producing a purine compound having a trifluoromethyl group, for example, Non-patent Document 3 discloses a method for producing 8-trifluoromethyladenine, 2,6-diamino-8-trifluoromethylpurine and 8-trifluoromethylhypoxanthine by reacting 4,5-diaminopyrimidines with trifluoroacetic acid or trifluoroacetic anhydride. Non-patent Document 4 discloses a method for producing 8-trifluoromethylguanine by reacting 2,4-diamino-5-trifluoroacetamino-6-oxo-1,6-dihydropyrimidine, which is obtained by a reaction of 2,4,5-triamino-6-oxo-1,6-dihydropyrimidine and trifluoroacetic acid, with trifluoroacetic anhydride. However, all of these methods also industrially have a problem of multi-steps including production of raw materials.

With respect to direct perfluoroalkylation of these nucleobases, for example, Patent Document 4 discloses a method for producing purines having a perfluoroalkyl group at the 8-position or 2-position by reacting purines with N,O-bis(trimethylsilyl)trifluoroacetamide in the presence of pyridine and trimethylchlorosilane as catalysts and then reacting the resultant with bis (perfluoroalkyl)peroxide. However, this method has problems that it uses di(haloacyl)peroxide which is industrially hard to handle, that it uses a chlorofluorocarbon solvent and that it forms regioisomers with the substituent at the different positions. Furthermore, non-patent Documents 5 and 6 disclose a method for producing 5-perfluorobutyluracil, 8-perfluorobutylhypoxanthine and an 8-perfluorobutylxanthine salts by the formation of a uracil anion electrochemically, followed by the reaction with perfluorobutyl iodide. However, this method has problems that it uses the electrochemical technique which is industrially hard to use and that the resulting product is a salt of a supporting electrolyte.

Non-patent Document 7 discloses a method for producing 8-trifluoromethylcaffeine by reacting 8-trifluoromethyltheophylline obtained by a reaction of 5,6-diamino-1,3-dimethyluracil and trifluoroacetic anhydride, with potassium carbonate and methyl iodide in N,N-dimethylformamide. However, this method industrially has a problem of multi-steps including production of raw materials.

With respect to perfluoroalkylation with a perfluoroalkyl halide, Non-patent Document 8 discloses a method for obtaining trifluoromethylnucleosides by reacting 2',3',5'-tri-O-acetylated iodonucleosides with copper powder and trifluoromethyl iodide in hexamethylphosphoric triamide to obtain a 2',3',5'-tri-O-acetylated trifluoromethylnucleosides, and followed by deprotecting them. However, this method also has problems of multi-steps and use of hexamethylphosphoric triamide which is industrially hard to use.

Moreover, Non-patent Documents 9 and 10 disclose a process using perfluorobutyl iodide or perfluoropropyl iodide which is liquid at room temperature, through the use of dimethyl sulfoxide, hydrogen peroxide and iron (II) sulfate. However, substrates are restricted to pyrroles, indoles and substituted benzenes. Furthermore, there is no description with respect to trifluoromethylation using a perfluoroalkyl halide which is gas at room temperature, for example, trifluoromethyl iodide.

Patent Document 1: JP-A-2001-247551
Patent Document 2: JP-A-11-246590
Patent Document 3: JP-A-6-73023
Non-patent Document 1: Journal of Organic Chemistry, Vol. 53, pp. 4582-4585, in 1988
Non-patent Document 2: Journal of Medicinal Chemistry, Vol. 13, pp. 151-152, in 1970
Non-patent Document 3: Journal of the American Chemical Society, Vol. 80, pp. 5744-5752, in 1957
Non-patent Document 4: Justus Libigs Annalen der Chemie, Vol. 726, pp. 201-215, in 1969
Patent Document 4: JP-A-5-1066
Non-patent Document 5: Tetrahedron Letters, Vol. 33, pp. 7351-7354, in 1992
Non-patent Document 6: Tetrahedron, Vol. 56, pp. 2655-2664, in 2000
Non-patent Document 7: Journal of Medicinal Chemistry, Vol. 36, pp. 2639-2644, in 1993
Non-patent Document 8: Journal of the Chemical Society, Perkin Transaction 1, pp. 2755-2761, in 1980

Non-patent Document 9: Tetrahedron Letters, Vol. 34, No. 23, pp. 3799-3800, in 1993

Non-patent Document 10: Journal of Organic Chemistry, Vol. 62, pp. 7128-7136, in 1997

DISCLOSURE OF THE INVENTION

Object to be Accomplished by the Invention

An object of the present invention is to provide a simple and efficient process for producing a nucleobase having a perfluoroalkyl group.

Means to Accomplish the Object

In order to accomplish the above object, the inventors of the present invention have conducted intensive and extensive studies and as a result, found that a nucleobase could be perfluoroalkylated in one step with a perfluoroalkyl halide in the presence of a sulfoxide, a peroxide and an iron compound, thereby very simply producing the nucleobase having a perfluoroalkyl group, so as to accomplish the present invention.

Namely, the present invention has the following aspects:
1. A process for producing a nucleobase having a perfluoroalkyl group, the process comprising: carrying out a reaction of a nucleobase with a perfluoroalkyl halide represented by the general formula (2)

wherein Rf is a C1-C6 perfluoroalkyl group and X is a halogen atom, in the presence of a sulfoxide represented by the general formula (1)

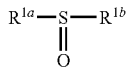

wherein each of $R^{1a}$ and $R^{1b}$ is a C1-C12 alkyl group or an optionally substituted phenyl group, a peroxide and an iron compound.
2. The process according to the above aspect 1, wherein the reaction is carried out in the presence of an acid.
3. The process according to the above aspect 1 or 2, wherein the nucleobase are uracils represented by the general formula (3)

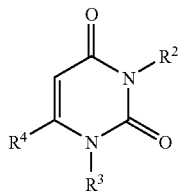

wherein $R^2$ is a hydrogen atom, an optionally substituted C1-C6 alkyl group or a protecting group for nitrogen, $R^3$ is a hydrogen atom, an optionally substituted C1-C6 alkyl group, a protecting group for nitrogen, or one of pentose residues and analogs thereof, and $R^4$ is a hydrogen atom, an optionally substituted C1-C6 alkyl group, an optionally substituted C1-C4 alkoxy group, an optionally substituted amino group, a carboxy group, an optionally substituted carbamoyl group, or an optionally substituted C2-C5 alkoxycarbonyl group; cytosines represented by the general formula (4)

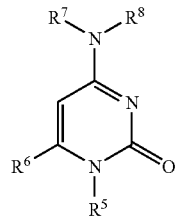

wherein $R^5$ is a hydrogen atom, an optionally substituted C1-C6 alkyl group, a protecting group for nitrogen, or one of pentose residues and analogs thereof, $R^6$ is a hydrogen atom, an optionally substituted C1-C6 alkyl group, an optionally substituted amino group, a carboxy group, an optionally substituted carbamoyl group, or an optionally substituted C2-C5 alkoxycarbonyl group, and each of $R^7$ and $R^8$ is a hydrogen atom or a protecting group for nitrogen; adenines represented by the general formula (5)

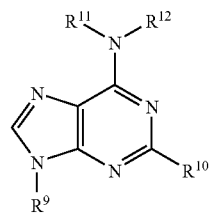

wherein $R^9$ is a hydrogen atom, an optionally substituted C1-C6 alkyl group, a protecting group for nitrogen, or one of pentose residues and analogs thereof, $R^{10}$ is a hydrogen atom, an optionally substituted C1-C6 alkyl group, an optionally substituted amino group, a carboxy group, an optionally substituted carbamoyl group, or an optionally substituted C2-C5 alkoxycarbonyl group, and each of $R^{11}$ and $R^{12}$ is a hydrogen atom or a protecting group for nitrogen; guanines represented by the general formula (6)

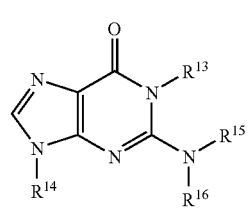

wherein $R^{13}$ is a hydrogen atom, an optionally substituted C1-C6 alkyl group or a protecting group for nitrogen, $R^{14}$ is a hydrogen atom, an optionally substituted C1-C6 alkyl group, a protecting group for nitrogen, or one of pentose residues and analogs thereof, and each of $R^{15}$ and $R^{16}$ is a hydrogen atom or a protecting group for nitrogen; a hypoxanthine compound represented by the general formula (7)

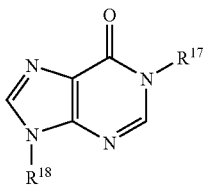

(7)

wherein $R^{17}$ is a hydrogen atom, an optionally substituted C1-C6 alkyl group or a protecting group for nitrogen, and $R^{18}$ is a hydrogen atom, an optionally substituted C1-C6 alkyl group, a protecting group for nitrogen, or one of pentose residues and analogs thereof; or xanthines represented by the general formula (8)

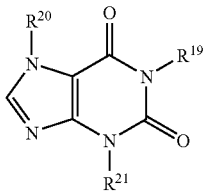

(8)

wherein $R^{19}$ is a hydrogen atom, an optionally substituted C1-C6 alkyl group or a protecting group for nitrogen, $R^{20}$ is a hydrogen atom, an optionally substituted C1-C6 alkyl group, a protecting group for nitrogen, or one of pentose residues and analogs thereof, and $R^{21}$ is a hydrogen atom, an optionally substituted C1-C6 alkyl group or a protecting group for nitrogen.

4. The process according to the above aspect 3, wherein the nucleobase are uracils represented by the general formula (3)

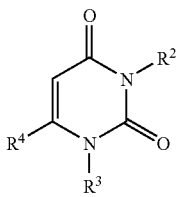

(3)

wherein $R^2$, $R^3$ and $R^4$ are the same as those defined above.

5. The process according to any one of the above aspects 1 to 4, wherein X is iodine or bromine.

6. The process according to any one of the above aspects 1 to 5, wherein Rf is a trifluoromethyl group or a perfluoroethyl group.

7. The process according to any one of the above aspects 1 to 6, wherein the iron compound is iron (II) sulfate, ammonium iron (II) sulfate, iron (II) tetrafluoroborate, iron (II) chloride, iron (II) bromide, iron (II) iodide, iron (II) acetate, iron (II) oxalate, bis(acetylacetonato)iron(II), ferrocene, bis($\eta^5$-pentamethylcyclopentadieny)iron or an iron powder.

8. The process according to the above aspect 7, wherein the iron compound is iron (II) sulfate, ammonium iron (II) sulfate, iron (II) tetrafluoroborate, ferrocene or an iron powder.

9. The process according to any one of the above aspects 1 to 8, wherein the peroxide is hydrogen peroxide, a hydrogen peroxide-urea composite, tert-butyl peroxide or peroxyacetic acid.

10. The process according to the above aspect 9, wherein the peroxide is hydrogen peroxide or a hydrogen peroxide-urea composite.

11. The process according to any one of the above aspects 2 to 10, wherein the acid is sulfuric acid, hydrochloric acid, hydrogen bromide, hydrogen iodide, nitric acid, phosphoric acid, hexafluorophosphoric acid, tetrafluoroboric acid, formic acid, acetic acid, propionic acid, oxalic acid, p-toluenesulfonic acid, trifluoromethanesulfonic acid or trifluoroacetic acid.

12. The process according to the above aspect 11, wherein the acid is sulfuric acid, tetrafluoroboric acid or trifluoromethanesulfonic acid.

13. The process according to any one of the above aspects 1 to 12, wherein each of $R^{1a}$ and $R^{1b}$ is a methyl group, a butyl group or a phenyl group.

14. The process according to any one of the above aspects 1 to 13, wherein a temperature of the reaction is from 20 to 100° C.

15. The process according to any one of the above aspects 1 to 14, wherein a pressure of the reaction is from the atmospheric pressure (0.1 MPa) to 1.0 MPa.

16. 5-Perfluoroalkyluracils represented by the general formula (9)

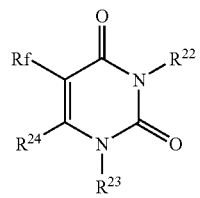

(9)

wherein Rf is a C1-C6 perfluoroalkyl group, each of $R^{22}$ and $R^{23}$ is a hydrogen atom or an optionally substituted C1-C6 alkyl group, and $R^{24}$ is an optionally substituted C1-C6 alkyl group, an optionally substituted amino group or an optionally substituted C2-C5 alkoxycarbonyl group, provided that in a case where each of $R^{22}$ and $R^{23}$ is a hydrogen atom, $R^{24}$ is an optionally substituted C2-C5 alkoxycarbonyl group.

17. 8-Perfluoroalkylxanthines represented by the general formula (10)

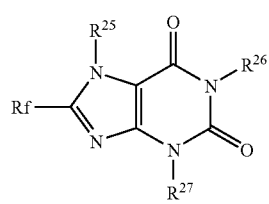

(10)

wherein Rf is a C1-C6 perfluoroalkyl group, and each of $R^{25}$, $R^{26}$ and $R^{27}$ is a hydrogen atom or an optionally substituted C1-C6 alkyl group, provided that $R^{25}$, $R^{26}$ and $R^{27}$ are not a hydrogen atom all together.

Effects of the Invention

The present invention realized high-yield and economical production of the nucleobase having a perfluoroalkyl group, which is a useful compound as a medical drug or an intermediate for medical and agricultural chemicals.

BEST MODE FOR CARRYING OUT THE INVENTION

Now, the present invention will be described in further detail.

Each of a nucleobase as a raw material and a nucleobase having a perfluoroalkyl group as a product in the present invention may be a mixture of tautomers such as a keto-form and an enol-form, and the present invention includes such tautomers. They are described in the keto-form in the description and claims of the present application for the sake of convenience.

Specific examples of the C1-C12 alkyl group denoted by each of $R^{1a}$ and $R^{1b}$ include a methyl group, an ethyl group, a propyl group, an isopropyl group, a cyclopropyl group, a butyl group, an isobutyl group, a sec-butyl group, a tert-butyl group, a cyclobutyl group, a cyclopropylmethyl group, a dodecyl group, and so on. Specific examples of the optionally substituted phenyl group denoted by each of $R^{1a}$ and $R^{1b}$ include a phenyl group, a p-tolyl group, a m-tolyl group, an o-tolyl group, and so on. Each of $R^{1a}$ and $R^{1b}$ is preferably a methyl group, a butyl group, a dodecyl group, a phenyl group or a p-tolyl group, and more preferably a methyl group, a butyl group or a phenyl group in terms of a good yield.

Specific examples of the C1-C6 perfluoroalkyl group denoted by Rf include a trifluoromethyl group, a perfluoroethyl group, a perfluoropropyl group, a perfluoroisopropyl group, a perfluorocyclopropyl group, a perfluorobutyl group, a perfluoroisobutyl group, a perfluoro-sec-butyl group, a perfluoro-tert-butyl group, a perfluorocyclobutyl group, a perfluorocyclopropylmethyl group, a perfluoropentyl group, a perfluoro-1,1-dimethylpropyl group, a perfluoro-1,2-dimethylpropyl group, a perfluoroneopentyl group, a perfluoro-1-methylbutyl group, a perfluoro-2-methylbutyl group, a perfluoro-3-methylbutyl group, a perfluorocyclobutylmethyl group, a perfluoro-2-cyclopropylethyl group, a perfluorocyclopentyl group, a perfluorohexyl group, a perfluoro-1-methylpentyl group, a perfluoro-2-methylpentyl group, a perfluoro-3-methylpentyl group, a perfluoroisohexyl group, a perfluoro-1,1-dimethylbutyl group, a perfluoro-1,2-dimethylbutyl group, a perfluoro-2,2-dimethylbutyl group, a perfluoro-1,3-dimethylbutyl group, a perfluoro-2,3-dimethylbutyl group, a perfluoro-3,3-dimethylbutyl group, a perfluoro-1-ethylbutyl group, a perfluoro-2-ethylbutyl group, a perfluoro-1,1,2-trimethylpropyl group, a perfluoro-1,2,2-trimethylpropyl group, a perfluoro-1-ethyl-1-methylpropyl group, a perfluoro-1-ethyl-2-methylpropyl group, a perfluorocyclohexyl group, and so on.

In terms of good performance as a medical drug and a good yield, Rf is preferably a trifluoromethyl group, a perfluoroethyl group, a perfluoropropyl group, a perfluoroisopropyl group, a perfluorobutyl group, a perfluoroisobutyl group, a perfluoro-sec-butyl group, a perfluoro-tert-butyl group or a perfluorohexyl group, more preferably a trifluoromethyl group or a perfluoroethyl group.

X is a halogen atom and specific examples thereof include a fluorine atom, a chlorine atom, a bromine atom and an iodine atom. In terms of a good yield, X is preferably an iodine atom or a bromine atom, and more preferably an iodine atom.

Examples of the nucleobase in the present invention include uracils, pseudouracils, thymines, cytosines, adenines, guanines, hypoxanthines and xanthines, whose basic skeletons are (N-1) to (N-8), respectively, as shown in Table 1.

TABLE 1

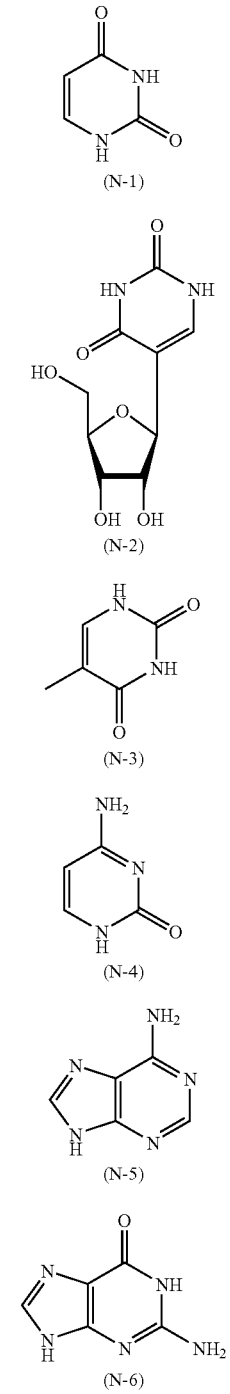

(N-1)

(N-2)

(N-3)

(N-4)

(N-5)

(N-6)

TABLE 1-continued

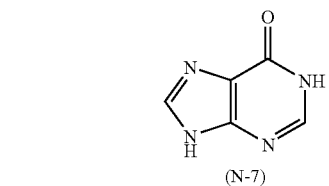

(N-7)

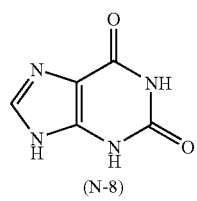

(N-8)

Of them the nucleobase are preferably uracils, cytosines, adenines, guanines, hypoxanthines or xanthines represented by the general formulae (3) to (8), respectively, and particularly preferably uracils represented by the general formula (3) among others in terms of good performance as a medical drug.

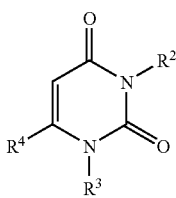

(3)

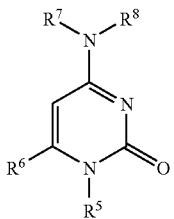

(4)

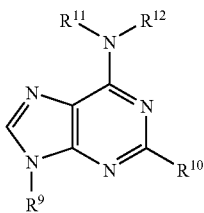

(5)

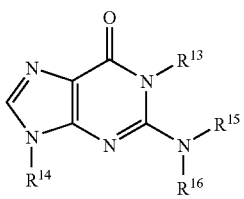

(6)

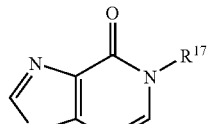

(7)

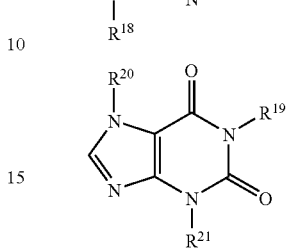

(8)

wherein $R^2$ is a hydrogen atom, an optionally substituted C1-C6 alkyl group or a protecting group for nitrogen, $R^3$ is a hydrogen atom, an optionally substituted C1-C6 alkyl group, a protecting group for nitrogen, or one of pentose residues and analogs thereof, $R^4$ is a hydrogen atom, an optionally substituted C1-C6 alkyl group, an optionally substituted C1-C4 alkoxy group, an optionally substituted amino group, a carboxy group, an optionally substituted carbamoyl group, or an optionally substituted C2-C5 alkoxycarbonyl group, $R^5$ is a hydrogen atom, an optionally substituted C1-C6 alkyl group, a protecting group for nitrogen, or one of pentose residues and analogs thereof, $R^6$ is a hydrogen atom, an optionally substituted C1-C6 alkyl group, an optionally substituted amino group, a carboxy group, an optionally substituted carbamoyl group, or an optionally substituted C2-C5 alkoxycarbonyl group, each of $R^7$ and $R^8$ is a hydrogen atom or a protecting group for nitrogen, $R^9$ is a hydrogen atom, an optionally substituted C1-C6 alkyl group, a protecting group for nitrogen, or one of pentose residues and analogs thereof, $R^{10}$ is a hydrogen atom, an optionally substituted C1-C6 alkyl group, an optionally substituted amino group, a carboxy group, an optionally substituted carbamoyl group, or an optionally substituted C2-C5 alkoxycarbonyl group, each of $R^{11}$ and $R^{12}$ is a hydrogen atom or a protecting group for nitrogen, $R^{13}$ is a hydrogen atom, an optionally substituted C1-C6 alkyl group or a protecting group for nitrogen, $R^{14}$ is a hydrogen atom, an optionally substituted C1-C6 alkyl group, a protecting group for nitrogen, or one of pentose residues and analogs thereof, each of $R^{15}$ and $R^{16}$ is a hydrogen atom or a protecting group for nitrogen, $R^{17}$ is a hydrogen atom, an optionally substituted C1-C6 alkyl group or a protecting group for nitrogen, $R^{18}$ is a hydrogen atom, an optionally substituted C1-C6 alkyl group, a protecting group for nitrogen, or one of pentose residues and analogs thereof, $R^{19}$ is a hydrogen atom, an optionally substituted C1-C6 alkyl group or a protecting group for nitrogen, $R^{20}$ is a hydrogen atom, an optionally substituted C1-C6 alkyl group, a protecting group for nitrogen, or one of pentose residues and analogs thereof, and $R^{21}$ is a hydrogen atom, an optionally substituted C1-C6 alkyl group or a protecting group for nitrogen.

Specific examples of the optionally substituted C1-C6 alkyl group denoted by each of $R^2$ and $R^3$ in the general formula (3) include a methyl group, an ethyl group, a propyl group, an isopropyl group, a cyclopropyl group, a butyl group, an isobutyl group, a sec-butyl group, a tert-butyl group, a cyclobutyl group, a cyclopropylmethyl group, a pentyl group, a neopentyl group, a hexyl group, a cyclohexyl group, and so on. Furthermore, each of these alkyl groups may be substituted by a halogen atom and specific examples of the substituted alkyl group include a chloromethyl group, a 2-chloroethyl group, a 3-chloropropyl group, a difluoromethyl group, a 3-fluoropropyl group, a trifluoromethyl group, a 2-fluoroethyl group, a 2,2,2-trifluoroethyl group, a 2,2,2-trichloroethyl group, and so on.

Specific examples of the protecting group for nitrogen denoted by each of $R^2$ and $R^3$ include an acetyl group, a propionyl group, a pivaloyl group, a propargyl group, a benzoyl group, a p-phenylbenzoyl group, a benzyl group, a p-methoxybenzyl group, a trityl group, a 4,4'-dimethoxytrityl group, a methoxyethoxymethyl group, a phenyloxycarbonyl group, a benzyloxycarbonyl group, a tert-butoxycarbonyl group, a 9-fluorenylmethoxycarbonyl group, an allyl group, a p-methoxyphenyl group, a trifluoroacetyl group, a methoxymethyl group, a 2-(trimethylsilyl)ethoxymethyl group, an allyloxycarbonyl group, a trichloroethoxycarbonyl group, and so on.

$R^2$ is preferably a hydrogen atom or a methyl group in terms of a good yield.

Specific examples of the pentose residues and analogs thereof denoted by $R^3$ include (P-1) to (P-401) shown in Tables 2 to 16. It is noted that in (P-1) to (P-401) a filled circle is a nitrogen atom to which the nucleobase bonds, Me is a methyl group, Et is an ethyl group, Pr is a propyl group, $^i$Pr is an isopropyl group, Bu is a butyl group, $^t$Bu is a tert-butyl group, Ph is a phenyl group, TMS is a trimethylsilyl group, TBDPS is a tert-butyldiphenylsilyl group and TS is a tosyl group.

In addition, a free hydroxyl group in the pentose residue may be protected with a protecting group generally used such as a benzoyl group, a p-chlorobenzoyl group, a toluoyl group, a benzyl group, a tert-butylcarbonyl group, a tert-butyldimethylsilyl group, an acetyl group, a mesyl group, a benzyloxycarbonyl group, a tert-butyldiphenylsilyl group, a trimethylsilyl group, a tosyl group, a tert-butylcarbonyl group, a p-methoxyphenylcarbonyl group, a p-monomethoxytrityl group, a di(p-methoxy)trityl group, a p-chlorophenylcarbonyl group, a m-trifluoromethylcarbonyl group, a pivaloyl group, a (9-fluorenyl)methoxycarbonyl group, a (biphenyl-4-yl)carbonyl group, a formyl group, a (2-naphthyl)carbonyl group, a tert-butyldimethylsilyl group, a triisopropylsilyl group, a tripropylsilyl group, a triphenylmethyl group, a butylcarbonyl group, an ethylcarbonyl group, a propylcarbonyl group, a nonylcarbonyl group or a p-methoxyphenyl group.

In addition, when the hydroxyl groups exist both at the 2'-position and 3'-position, they may be protected together by an isopropylidene group or the like to form a ring. Furthermore, a free amino group may be protected with a protecting group generally used such as a trifluoromethylcarbonyl group, a 2,4-dinitrophenyl group, a tosyl group, an acetyl group, a benzyloxycarbonyl group, a triphenylmethyl group, a benzoyl group, a benzyl group, an adamantylcarbonyl group, a butylcarbonyl group, a phthaloyl group or a tetrabromophthaloyl group. Moreover, a free mercapto group may be protected with a protecting group generally used such as a 2,4,6-triisopropylphenyl group, a benzoyl group, a benzyl group or an acetyl group.

TABLE 2

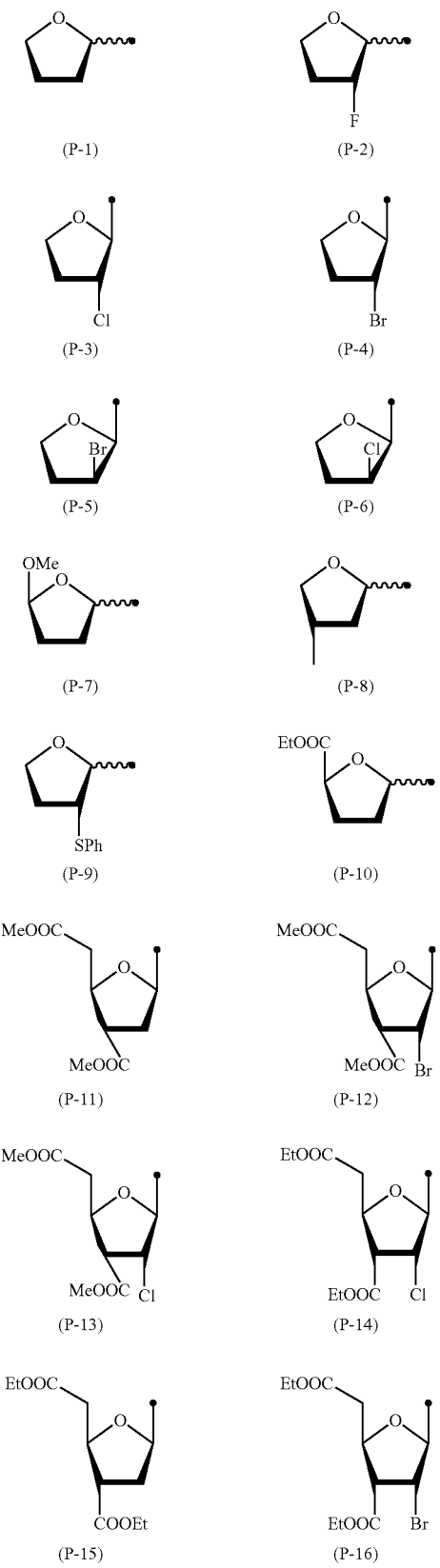

TABLE 2-continued
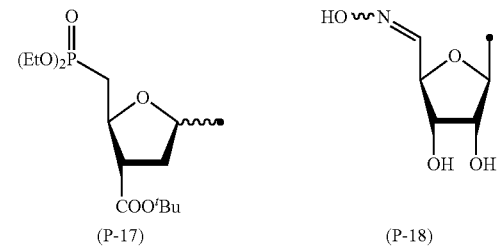
(P-17)　　　(P-18)
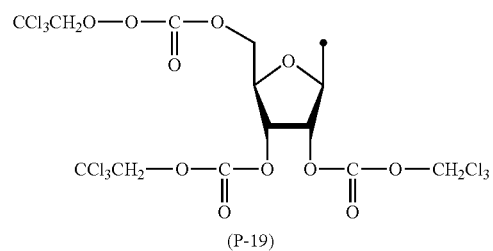
(P-19)
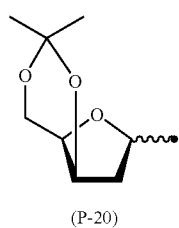 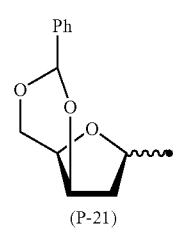
(P-20)　　　(P-21)
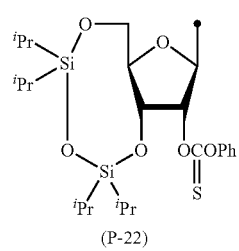 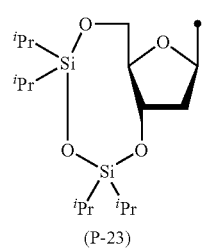
(P-22)　　　(P-23)
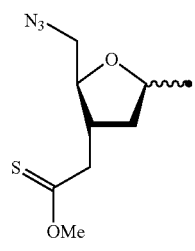 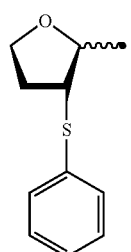
(P-24)　　　(P-25)
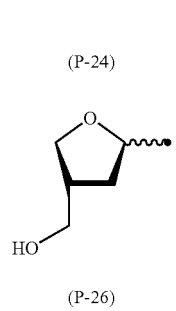
(P-26)　　　(P-27)
TABLE 2-continued
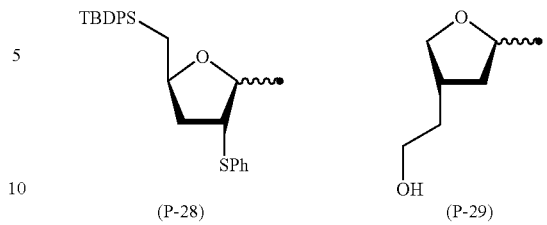
(P-28)　　　(P-29)
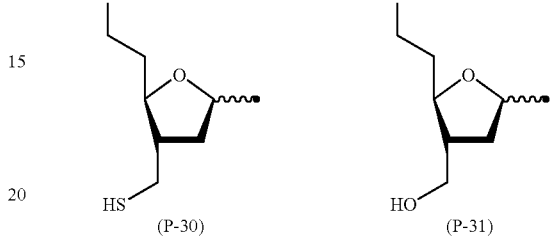
(P-30)　　　(P-31)
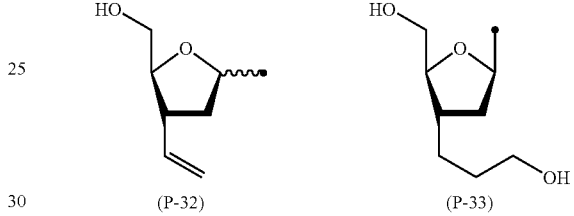
(P-32)　　　(P-33)
TABLE 3
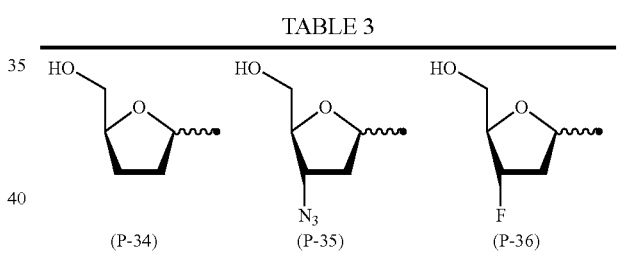
(P-34)　　(P-35)　　(P-36)
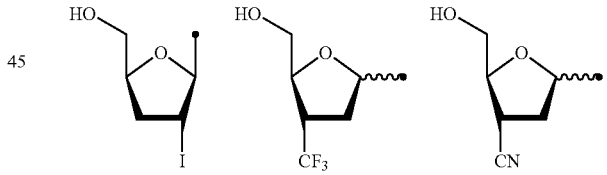
(P-37)　　(P-38)　　(P-39)
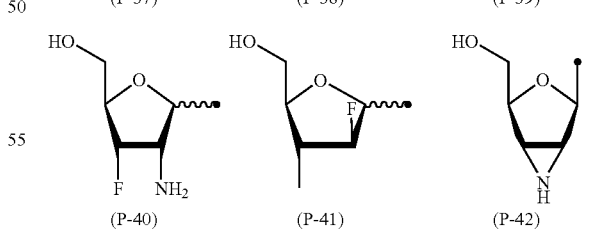
(P-40)　　(P-41)　　(P-42)
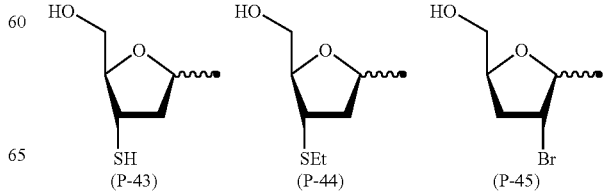
(P-43)　　(P-44)　　(P-45)

TABLE 3-continued
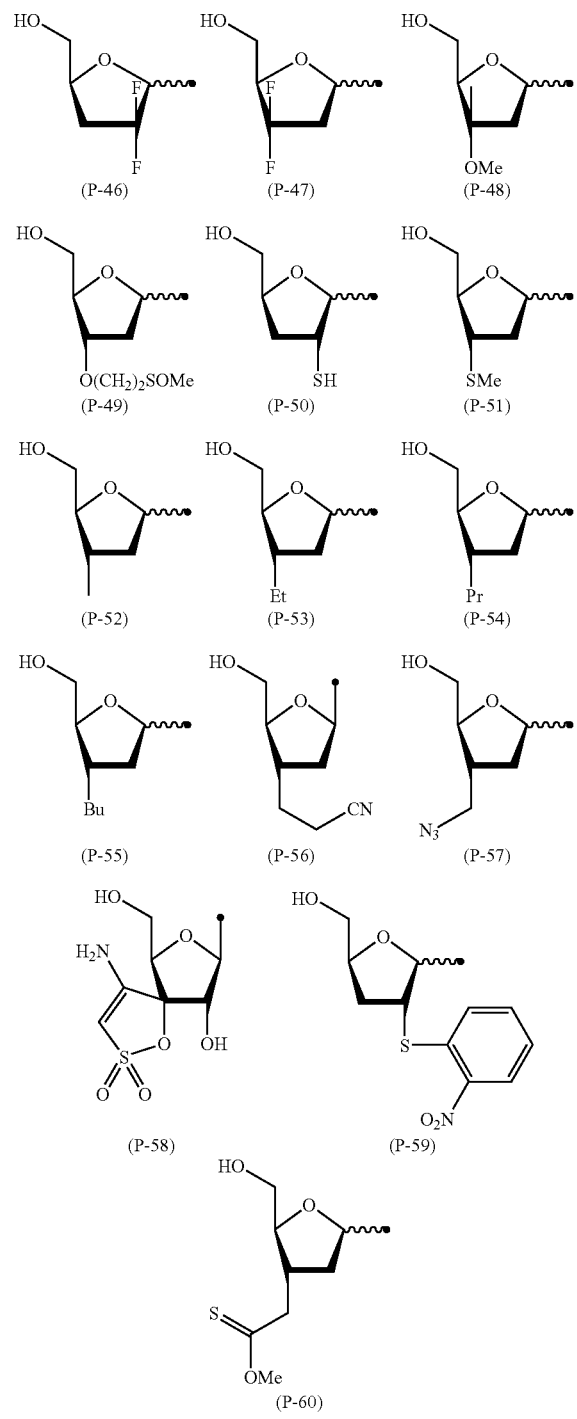
TABLE 4
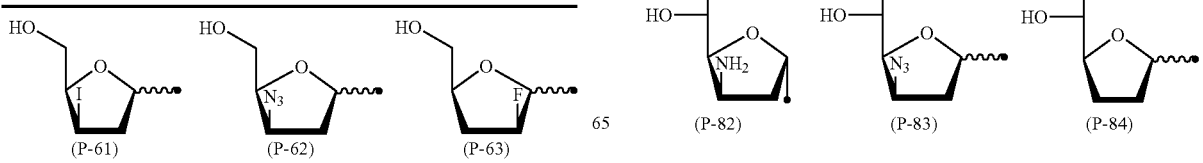
TABLE 4-continued
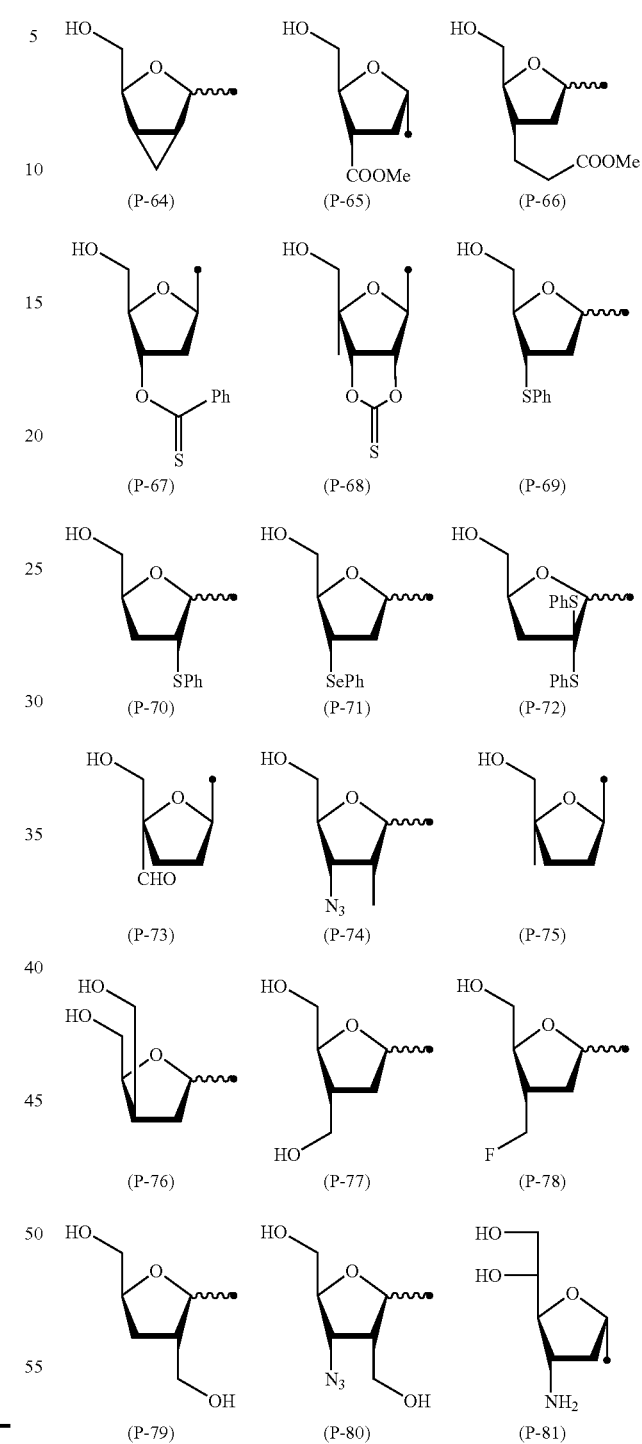

TABLE 4-continued
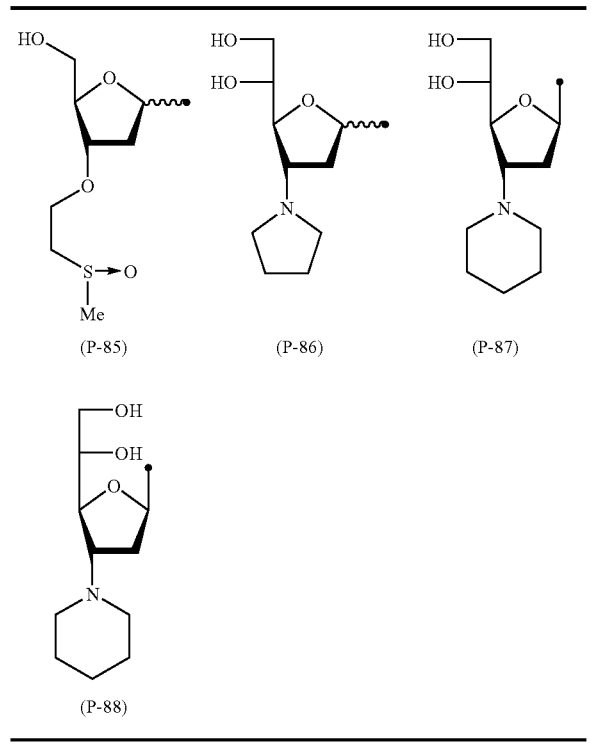
TABLE 5
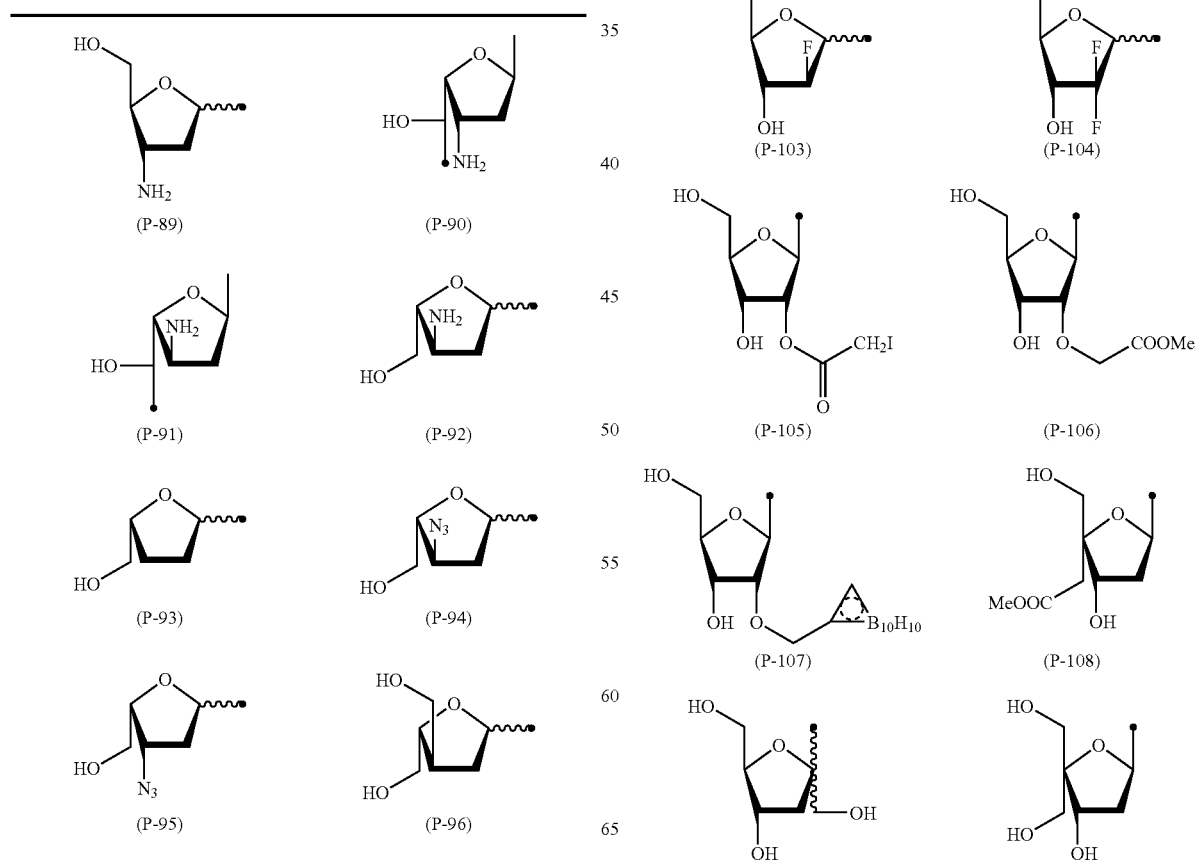
TABLE 5-continued
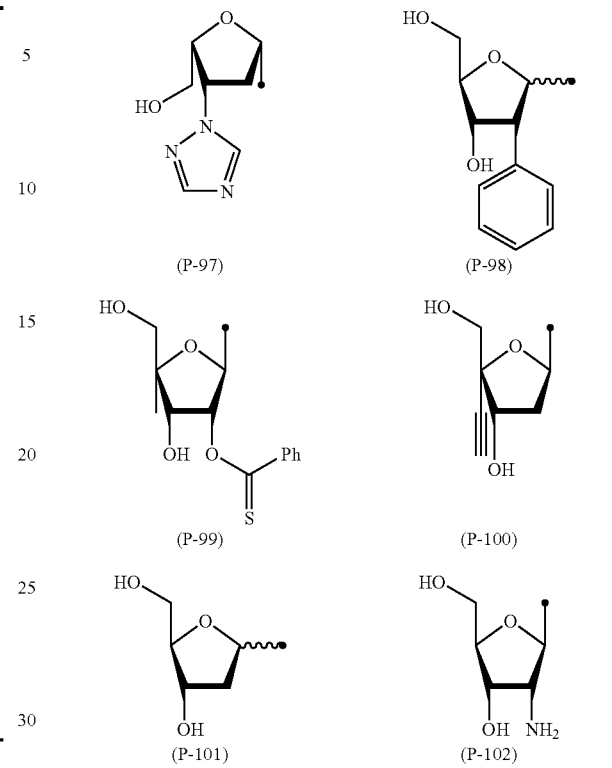

TABLE 5-continued

TABLE 6

TABLE 7
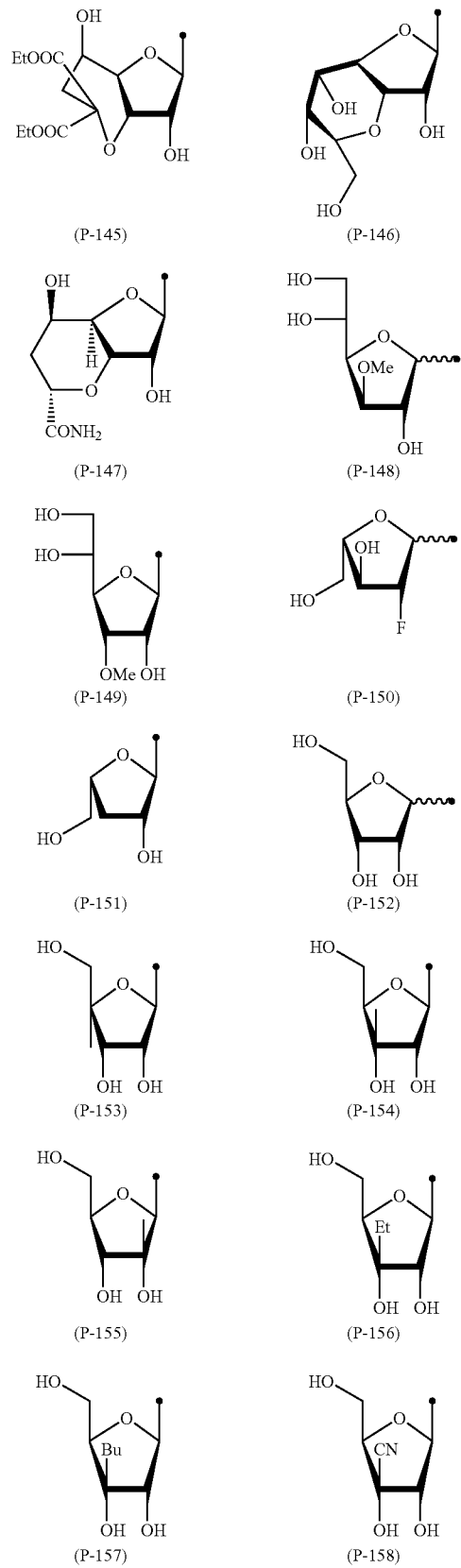
TABLE 7-continued
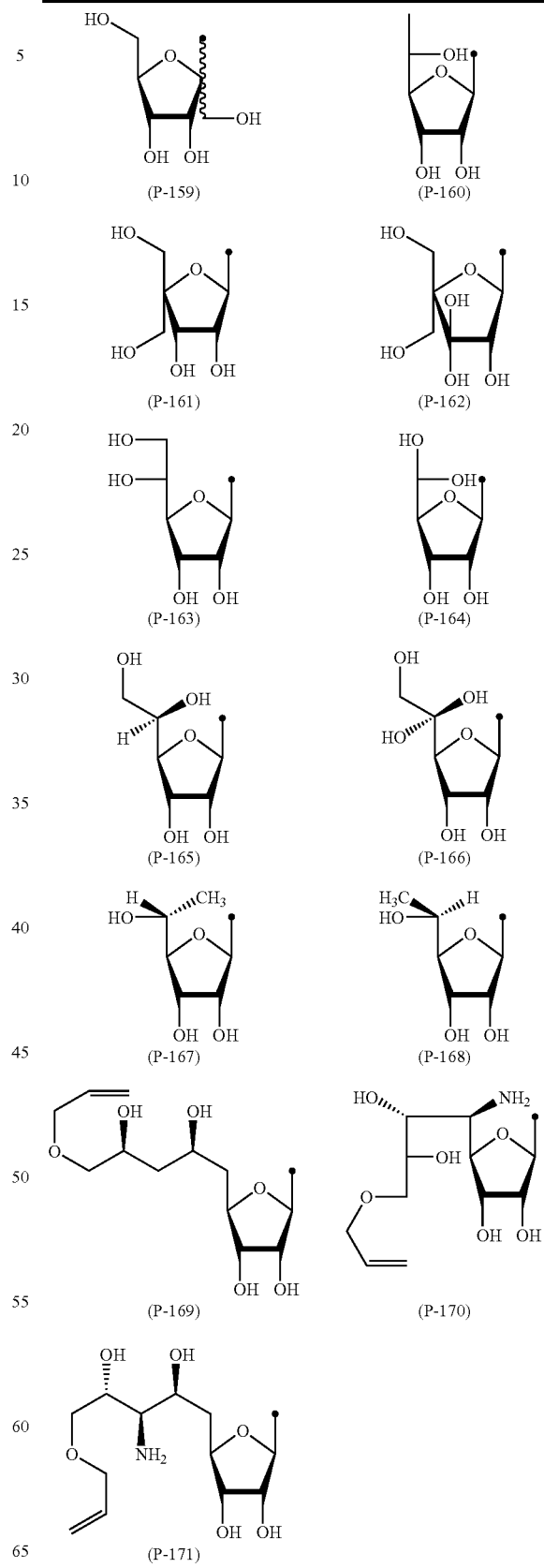

TABLE 8

(P-172), (P-173), (P-174), (P-175), (P-176), (P-177), (P-178), (P-179), (P-180), (P-181), (P-182), (P-183), (P-184), (P-185), (P-186), (P-187), (P-188), (P-189), (P-190), (P-191), (P-192), (P-193), (P-194), (P-195), (P-196), (P-197)

TABLE 8-continued
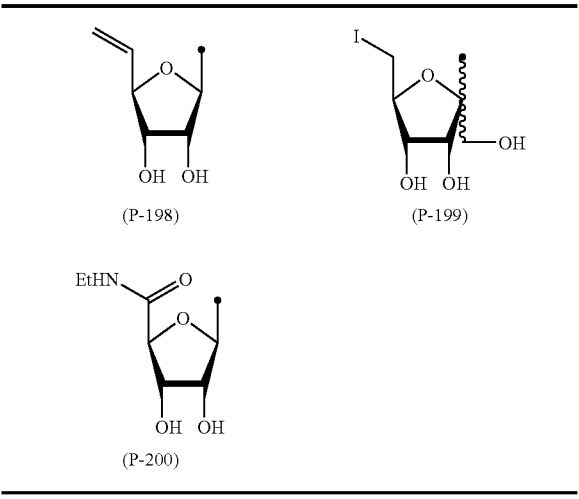
TABLE 9
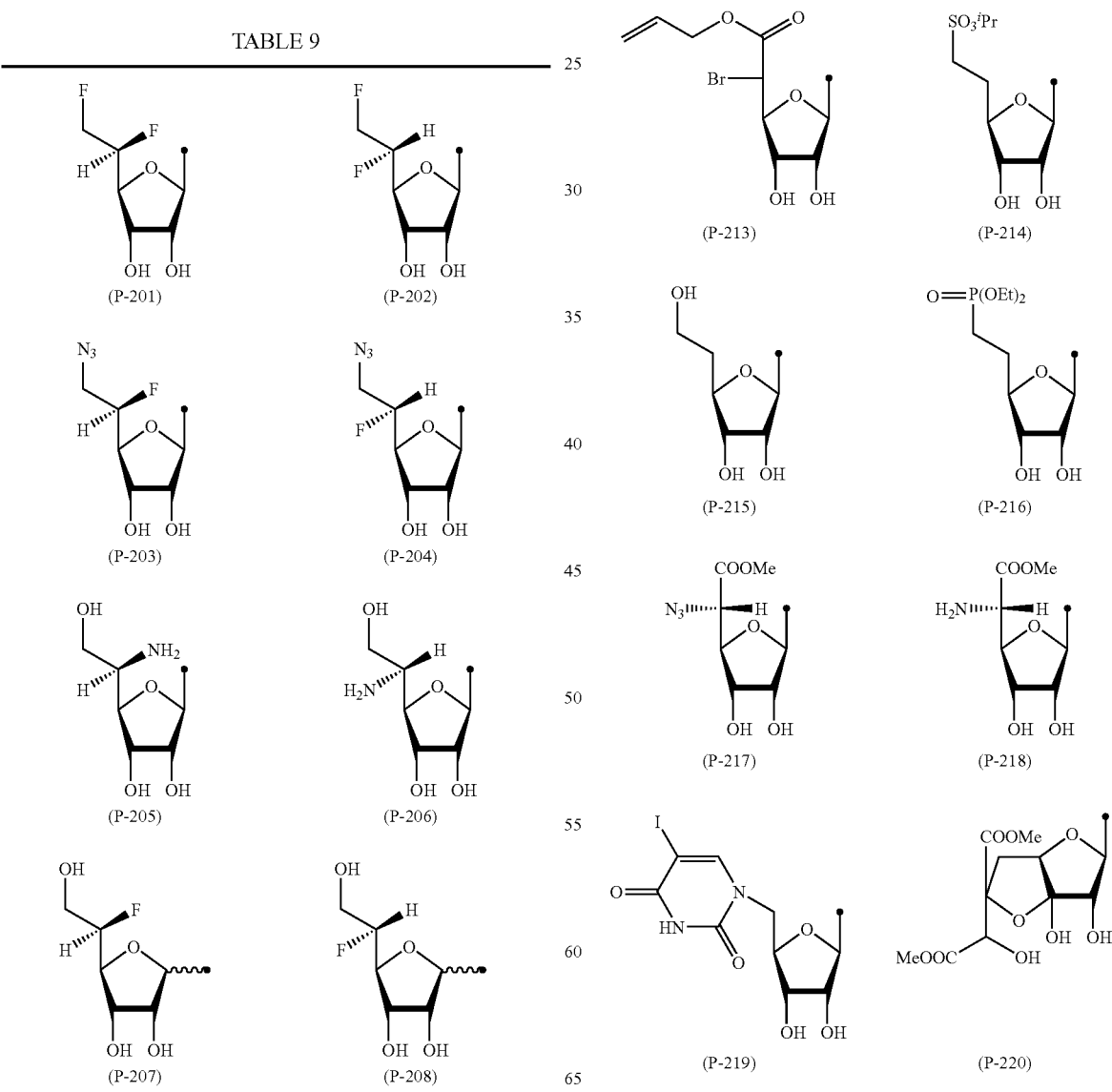

TABLE 9-continued
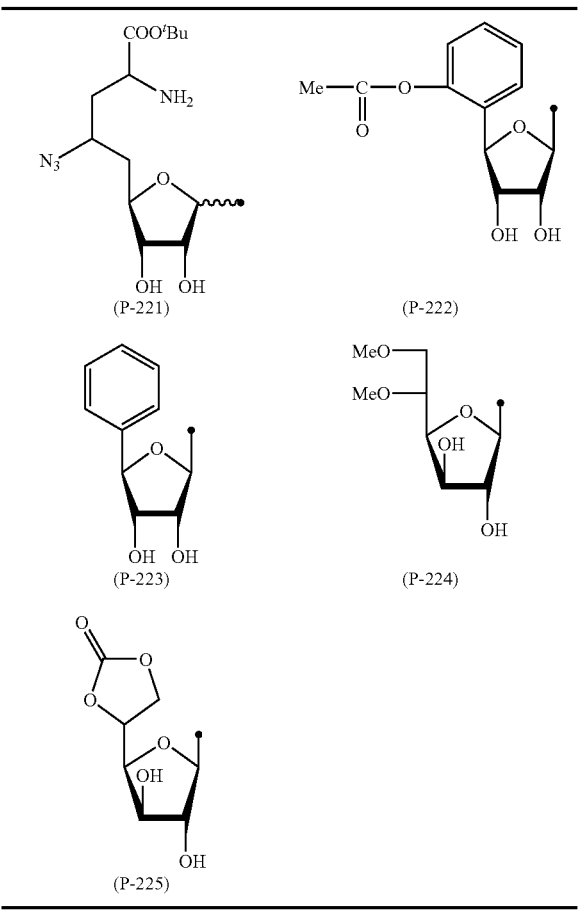
TABLE 10
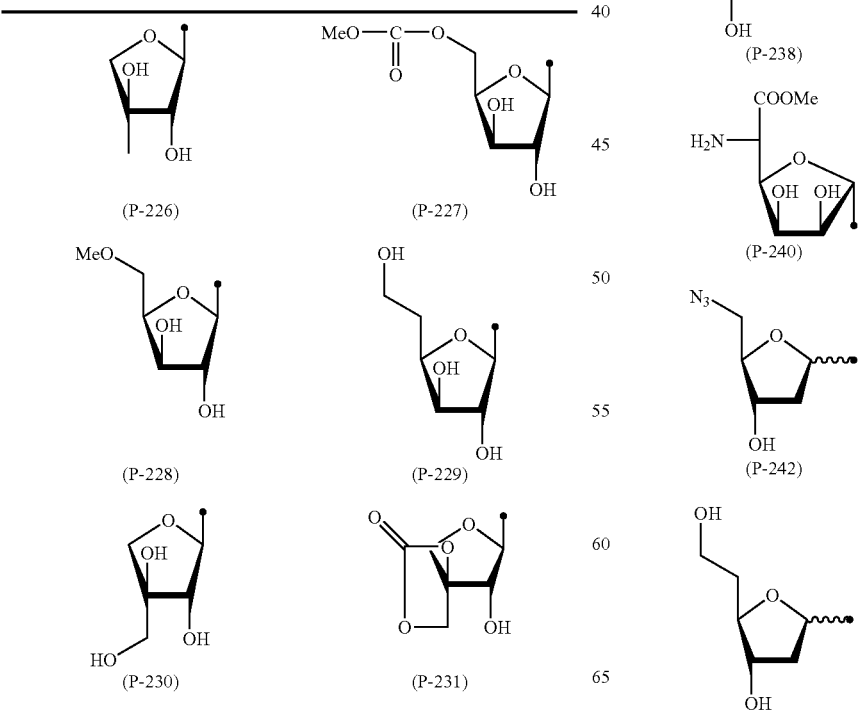
TABLE 10-continued
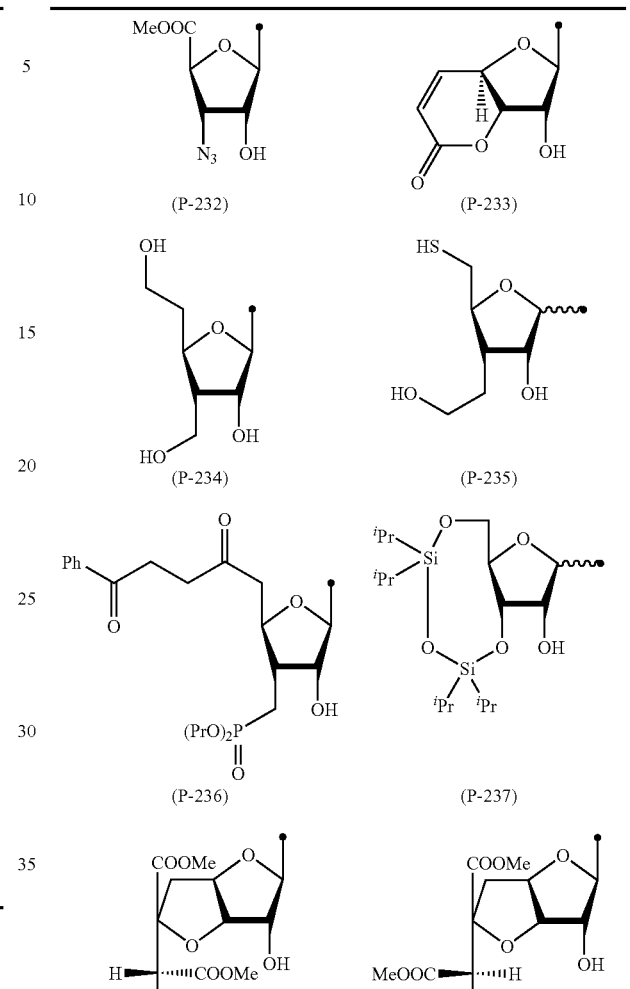

TABLE 10-continued
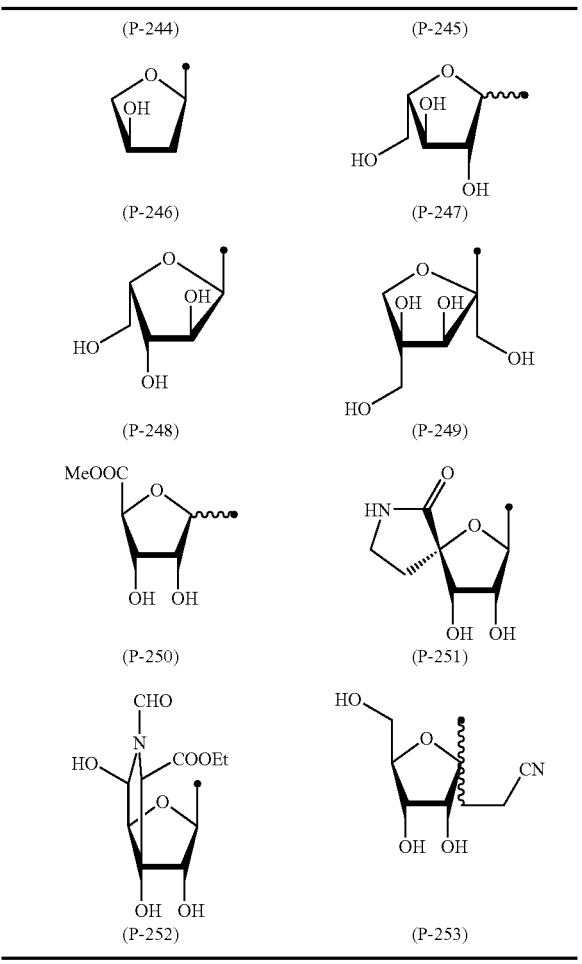
TABLE 11
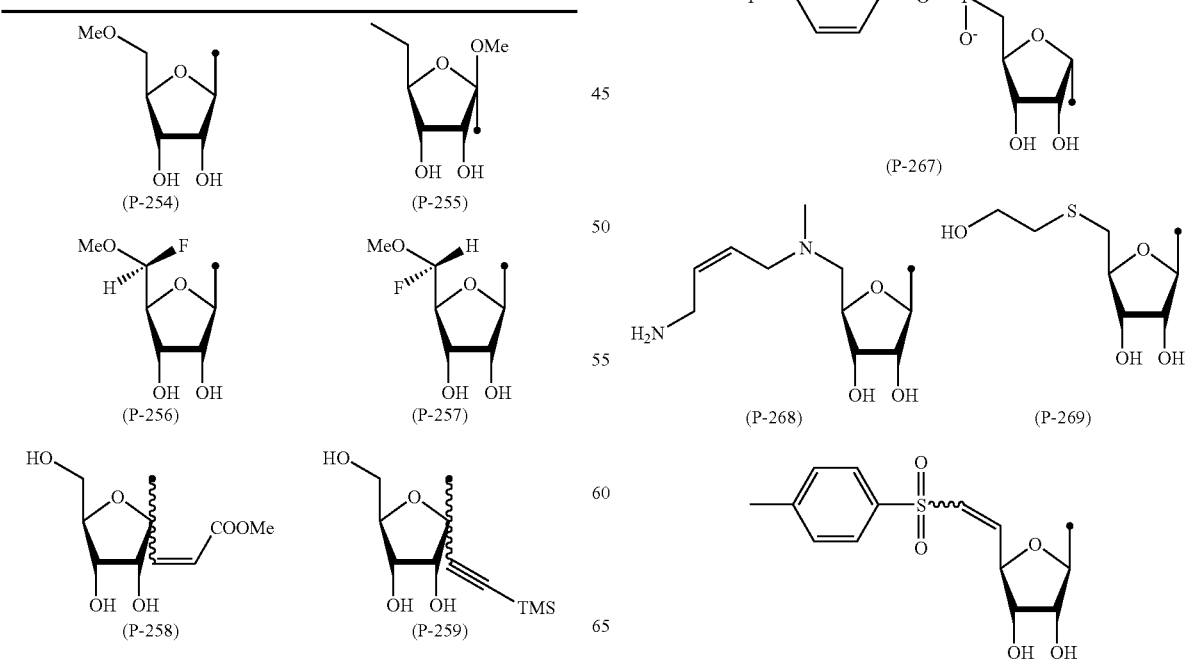

TABLE 11-continued
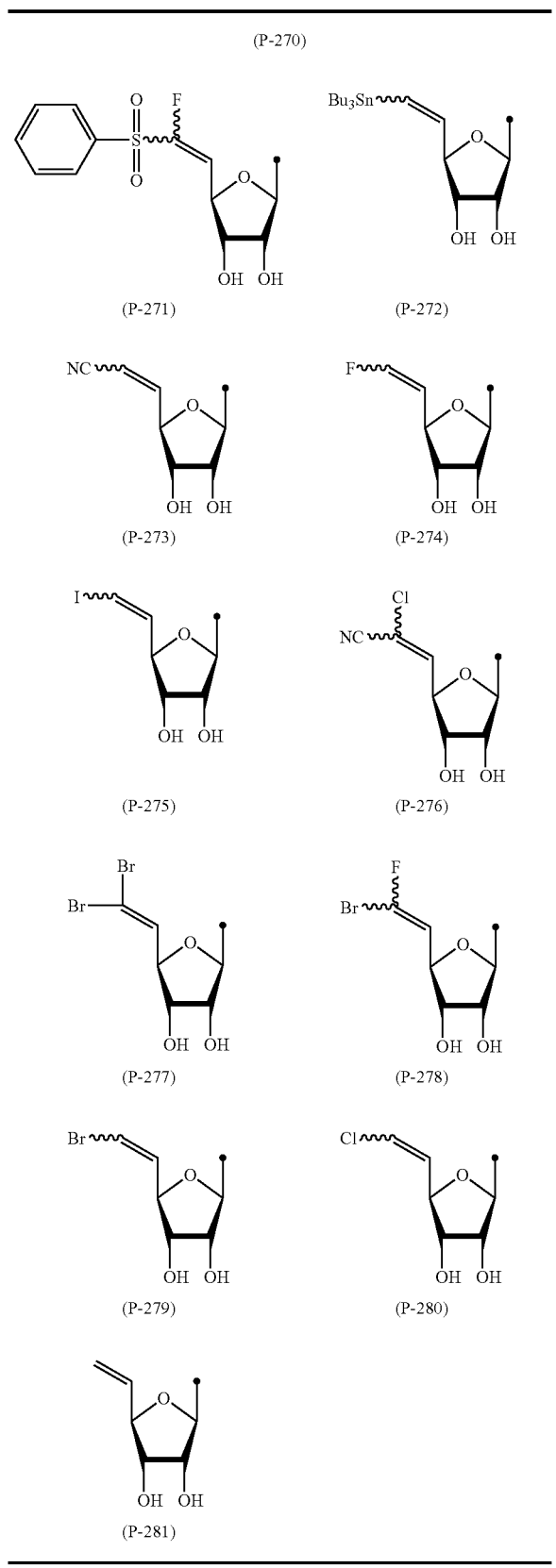
TABLE 12
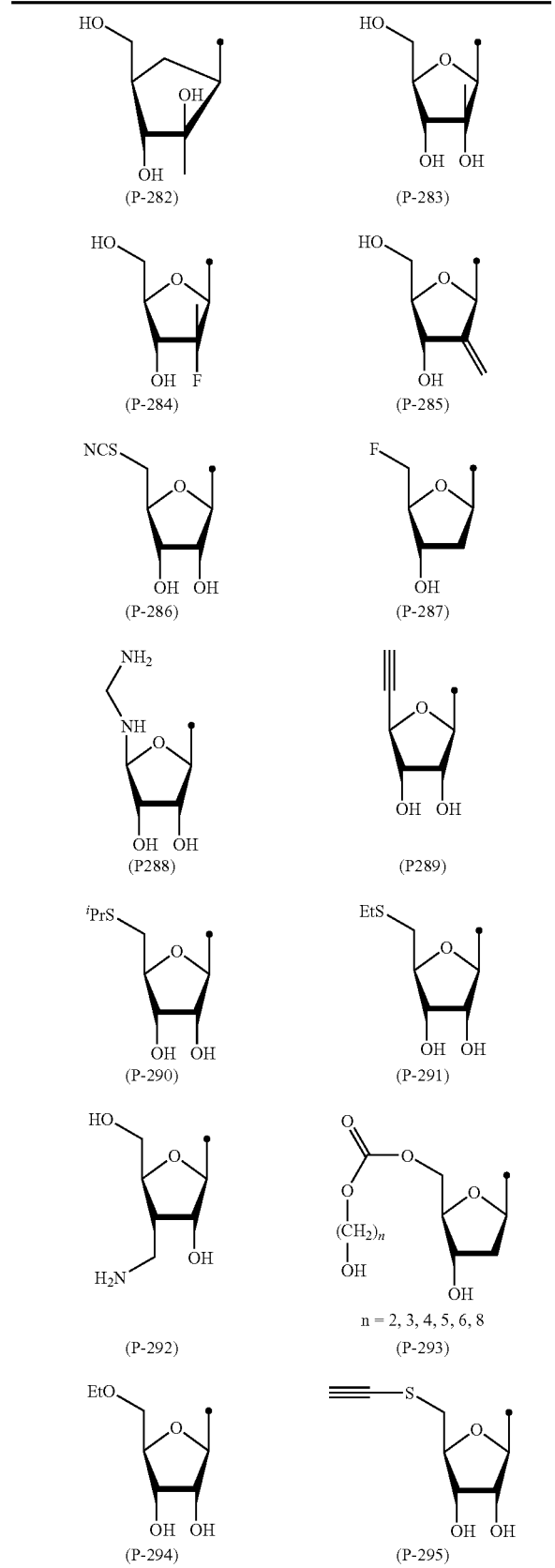

TABLE 12-continued
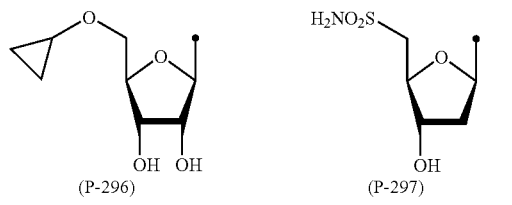
(P-296)  (P-297)
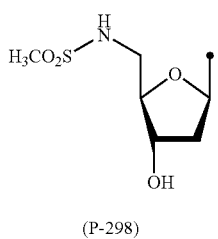
(P-298)  (P-299)
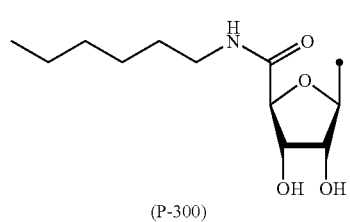
(P-300)
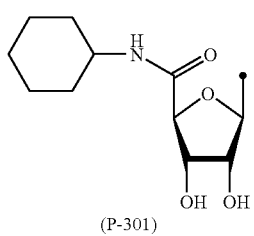 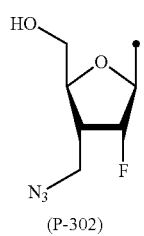
(P-301)  (P-302)
 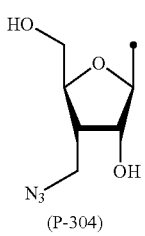
(P-303)  (P-304)
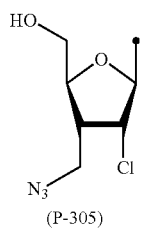 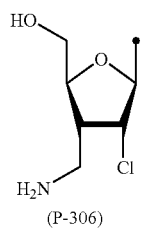
(P-305)  (P-306)
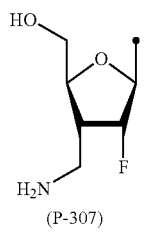 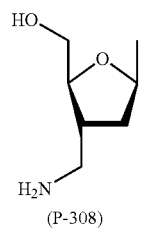
(P-307)  (P-308)
TABLE 12-continued
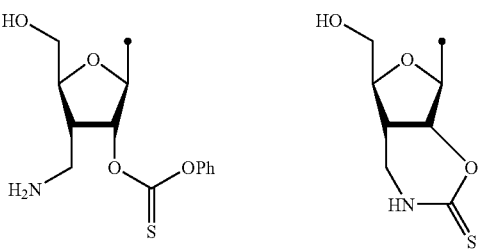
(P-309)  (P-310)
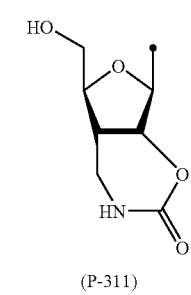 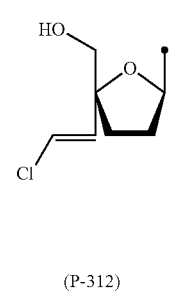
(P-311)  (P-312)
TABLE 13
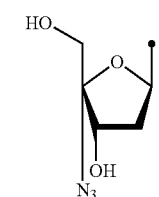 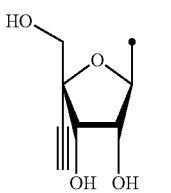
(P-313)  (P-314)
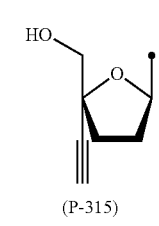 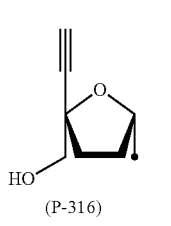
(P-315)  (P-316)
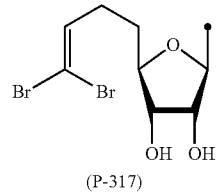 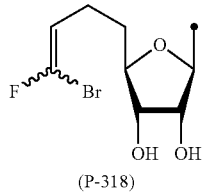
(P-317)  (P-318)
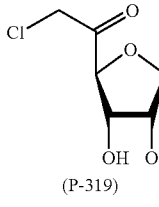 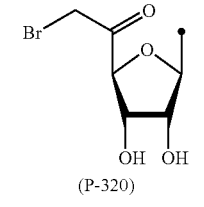
(P-319)  (P-320)

TABLE 13-continued
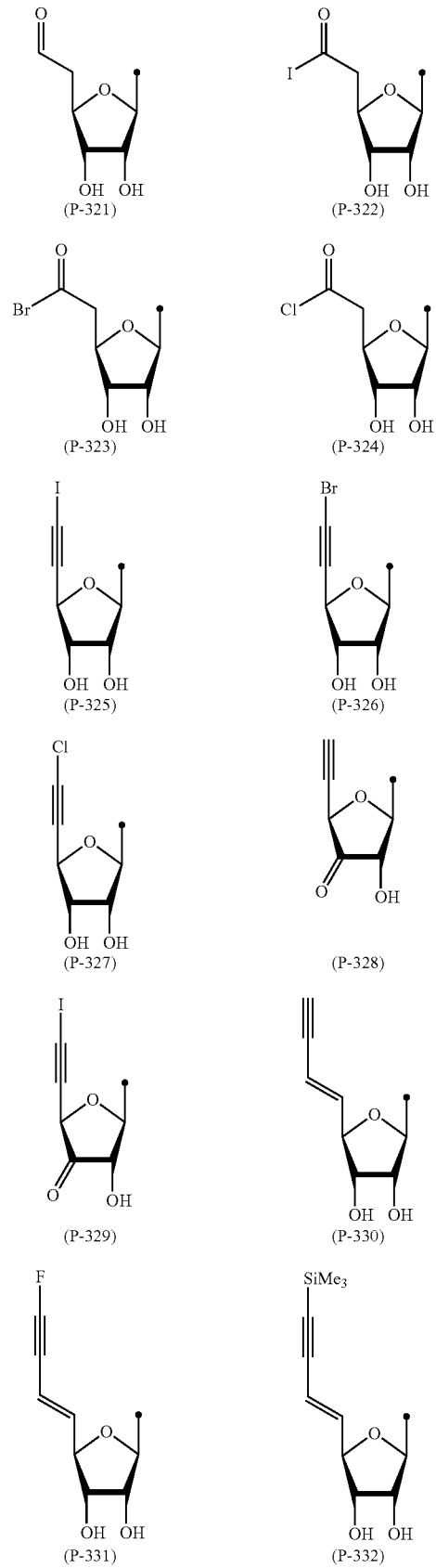
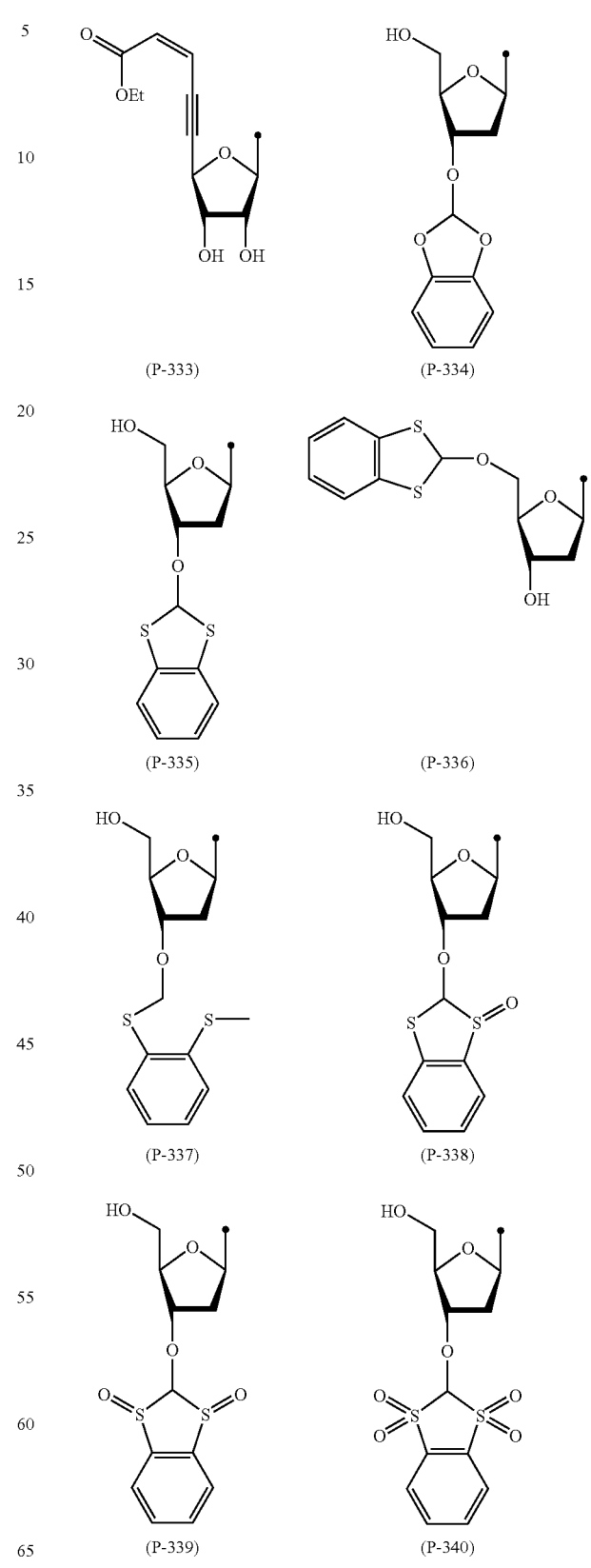

TABLE 13-continued
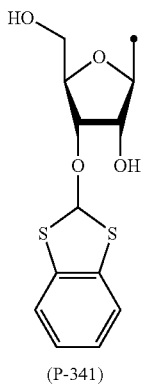
(P-341)
TABLE 14
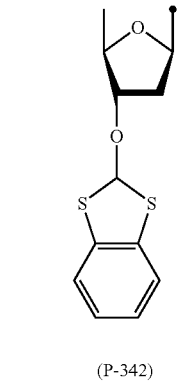 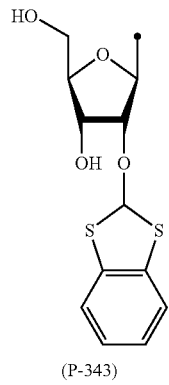
(P-342) (P-343)
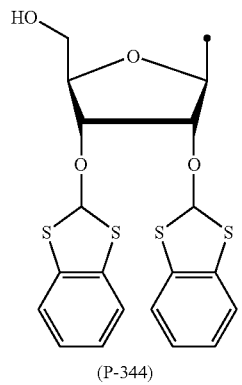 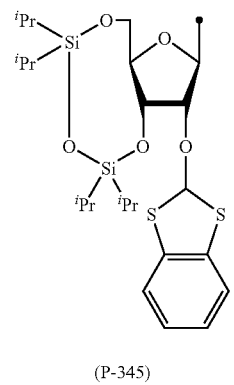
(P-344) (P-345)
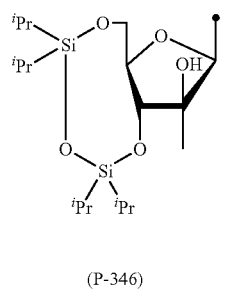 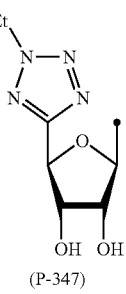
(P-346) (P-347)
TABLE 14-continued
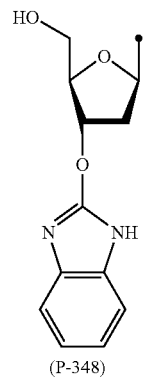 
(P-348) (P-349)
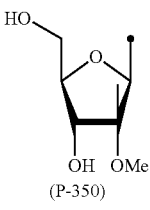 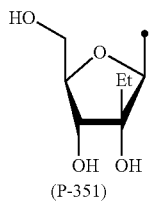
(P-350) (P-351)
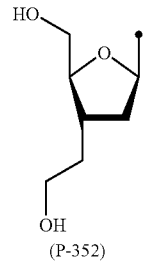 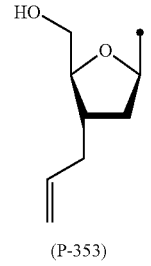
(P-352) (P-353)
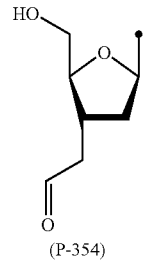 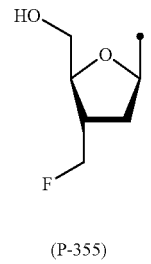
(P-354) (P-355)
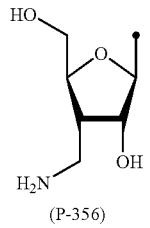 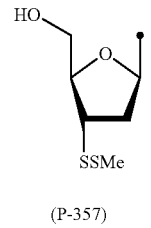
(P-356) (P-357)
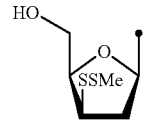 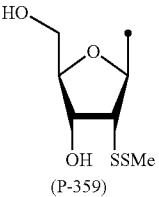
(P-358) (P-359)

TABLE 14-continued
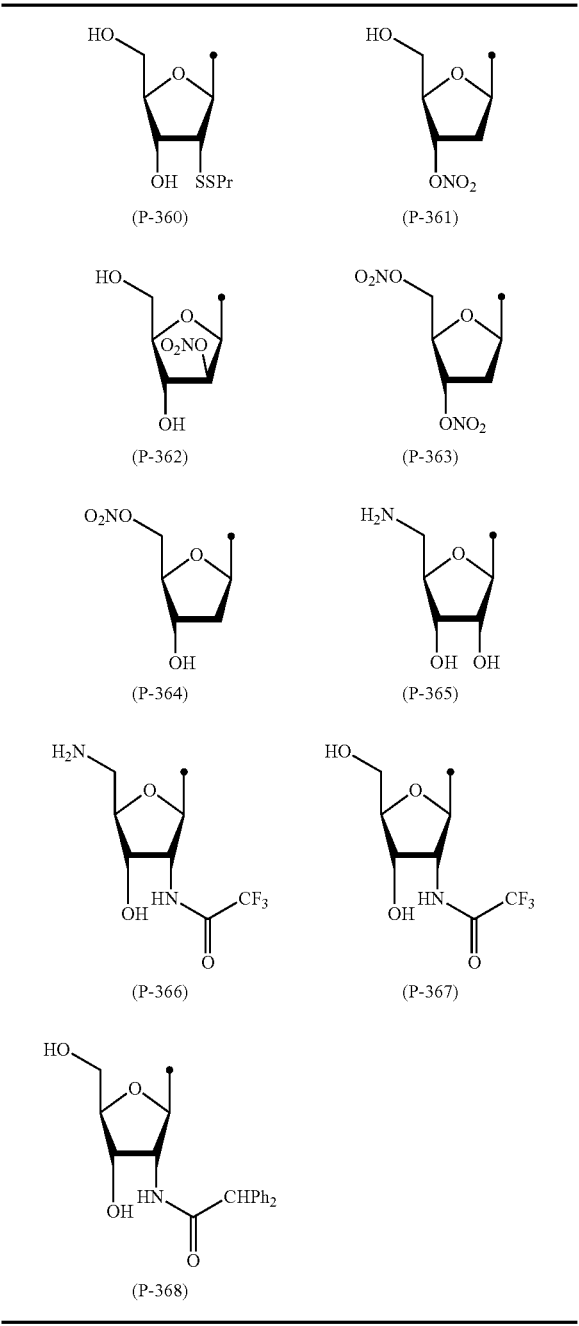
TABLE 15
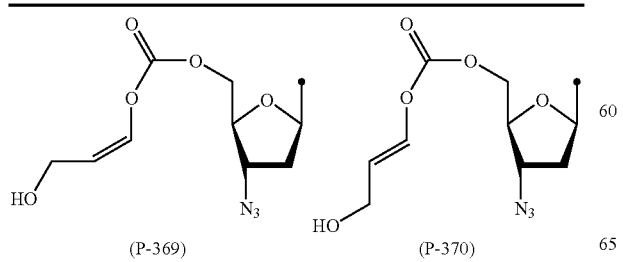
TABLE 15-continued
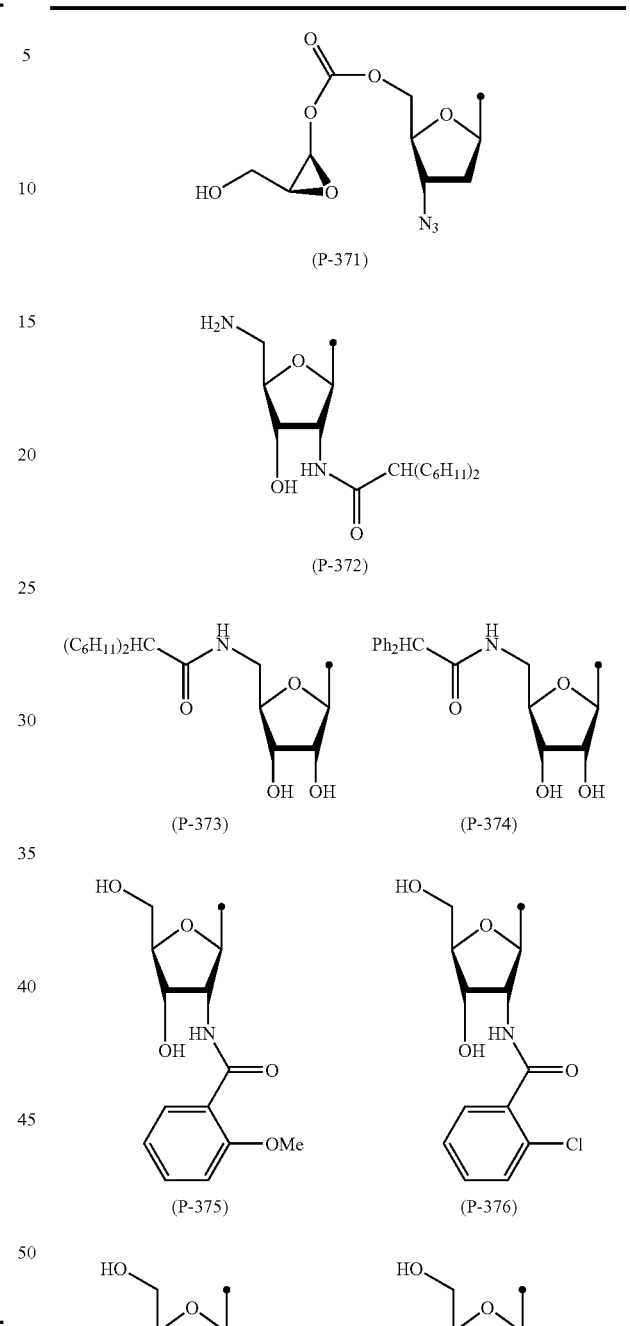

TABLE 15-continued
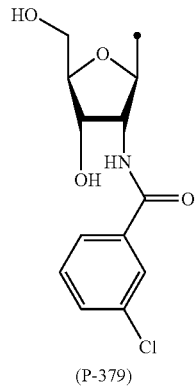
(P-379)
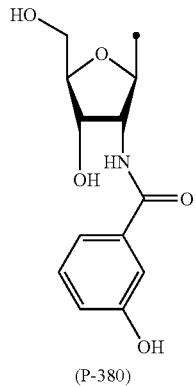
(P-380)
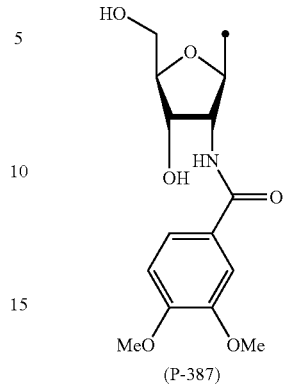
(P-387)
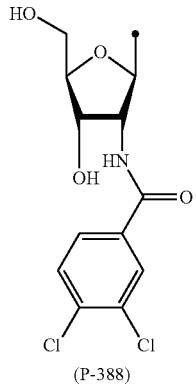
(P-388)
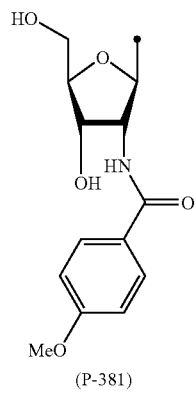
(P-381)
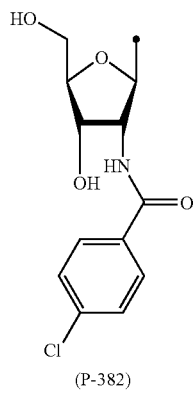
(P-382)
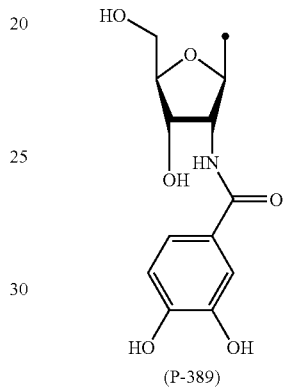
(P-389)
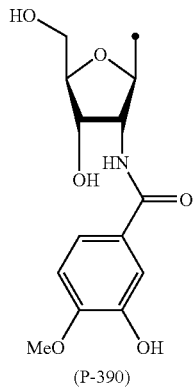
(P-390)
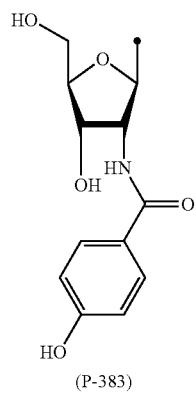
(P-383)
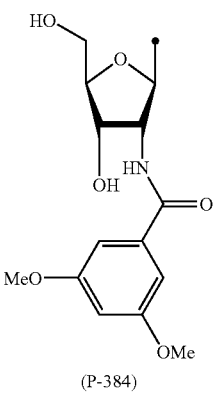
(P-384)
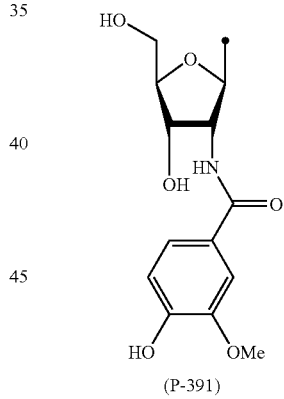
(P-391)
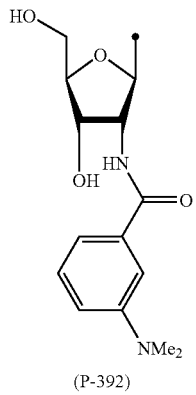
(P-392)
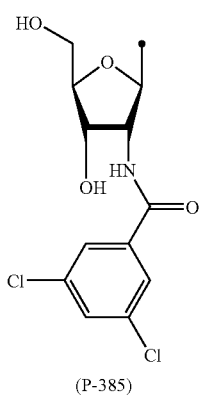
(P-385)
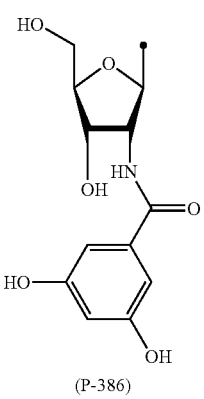
(P-386)
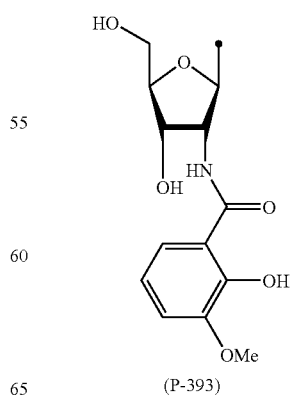
(P-393)

TABLE 16

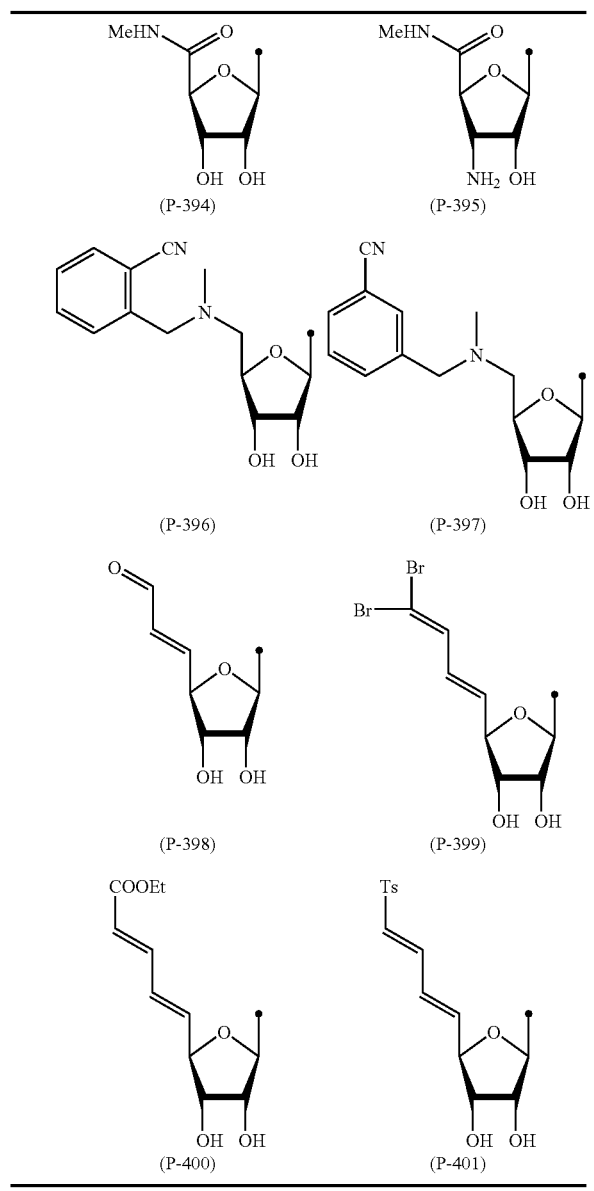

R³ is preferably a hydrogen atom, a methyl group, (P-34), (P-35), (P-75), (P-100), (P-101), (P-123), (P-152), (P-153), (P-314) or (P-315) in terms of usefulness as a medical or agricultural chemical or an intermediate thereof.

Specific examples of the optionally substituted C1-C6 alkyl group denoted by $R^4$ in the general formula (3) include the optionally substituted C1-C6 alkyl groups described in the description of $R^2$.

Specific examples of the optionally substituted C1-C4 alkoxy group include a methoxy group, an ethoxy group, a propoxy group, an isopropyloxy group, a cyclopropyloxy group, a butoxy group, an isobutyloxy group, a sec-butyloxy group, a tert-butyloxy group, a cyclobutyloxy group, a cyclopropylmethyloxy group and so on. Furthermore each of these alkoxy groups may be substituted by a halogen atom, and specific examples thereof include a chloromethoxy group, a 2-chloroethoxy group, a 3-chloropropoxy group, a difluoromethoxy group, a 3-fluoropropoxy group, a trifluoromethoxy group, a 2-fluoroethoxy group, a 2,2,2-trifluoroethoxy group, a 2,2,2-trichloroethoxy group, and so on.

Examples of the optionally substituted amino group denoted by $R^4$ include an amino group which may be substituted by a C1-C4 alkyl group and specific examples thereof include an amino group, a methylamino group, an ethylamino group, a propylamino group, an isopropylamino group, a butylamino group, an isobutylamino group, a sec-butylamino group, a tert-butylamino group, an N,N-dimethylamino group, an N,N-diethylamino group, an N,N-dipropylamino group, an N,N-diisopropylamino group, an N,N-dibutylamino group, an N,N-diisobutylamino group, an N,N-di-sec-butylamino group, an N,N-di-tert-butylamino group, and so on.

Furthermore, the amino group may be substituted by a protecting group for nitrogen, and specific examples of the substituted amino group include an acetylamino group, a propionylamino group, a pivaloylamino group, a propargylamino group, a benzoylamino group, a p-phenylbenzoylamino group, a benzylamino group, a p-methoxybenzylamino group, a tritylamino group, a 4,4'-dimethoxytritylamino group, a methoxyethoxymethylamino group, a phenyloxycarbonylamino group, a benzyloxycarbonylamino group, a tert-butoxycarbonylamino group, a 9-fluorenylmethoxycarbonylamino group, an allylamino group, a p-methoxyphenylamino group, a trifluoroacetylamino group, a methoxymethylamino group, a 2-(trimethylsilyl)ethoxymethylamino group, an allyloxycarbonylamino group, a trichloroethoxycarbonylamino group, and so on.

An example of the optically substituted carbamoyl group denoted by $R^4$ includes a carbamoyl group which may be substituted by a C1-C4 alkyl group on the nitrogen atom, and specific examples thereof include a carbamoyl group, an N-methylcarbamoyl group, an N-ethylcarbamoyl group, an N-propylcarbamoyl group, an N-isopropylcarbamoyl group, an N-butylcarbamoyl group, an N,N-dimethylcarbamoyl group, an N,N-diethylcarbamoyl group, an N,N-dipropylcarbamoyl group, an N,N-diisopropylcarbamoyl group, an N,N-dibutylcarbamoyl group, and so on.

Specific examples of the optionally substituted C2-C5 alkoxycarbonyl group denoted by $R^4$ include a methoxycarbonyl group, an ethoxycarbonyl group, a propoxycarbonyl group, an isopropyloxycarbonyl group, a butyloxycarbonyl group, an isobutyloxycarbonyl group, a sec-butyloxycarbonyl group, a tert-butyloxycarbonyl group and so on. Furthermore, each of these alkoxycarbonyl groups may be substituted by a halogen atom, and specific examples of the substituted alkoxycarbonyl group include a 2-chloroethoxycarbonyl group, a 3-chloropropyloxycarbonyl group, a difluoromethoxycarbonyl group, a 3-fluoropropyloxycarbonyl group, a trifluoromethoxycarbonyl group, a 2-fluoroethoxycarbonyl group, a 2,2,2-trifluoroethoxycarbonyl group, a 2,2,2-trichloroethoxycarbonyl group, and so on.

$R^4$ is preferably a hydrogen atom, a 2-chloroethyl group, an amino group, a tert-butoxycarbonylamino group or a carboxy group in terms of a good yield.

Specific examples of the optionally substituted C1-C6 alkyl group denoted by $R^5$ in the general formula (4) include the optionally substituted C1-C6 alkyl groups described in the description of $R^2$. Specific examples of the protecting group for nitrogen denoted by $R^5$ include the protecting groups for nitrogen described in the description of $R^2$. Specific examples of the pentose residues and analogs thereof denoted by $R^5$ include (P-1) to (P-401) described in the description of $R^3$. $R^5$ is preferably a hydrogen atom, a methyl group, (P-34), (P-35), (P-75), (P-100), (P-101), (P-123), (P-152), (P-153), (P-314) or (P-315) in terms of usefulness as a medical or agricultural chemical or an intermediate thereof.

Specific examples of the optionally substituted C1-C6 alkyl group denoted by $R^6$ in the general formula (4) include the optionally substituted C1-C6 alkyl groups described in the description of $R^2$. Specific examples of the optionally substituted amino group denoted by $R^6$ include the optionally substituted amino groups described in the description of $R^4$. Specific examples of the optionally substituted carbamoyl group denoted by $R^6$ include the optionally substituted carbamoyl groups described in the description of $R^4$. Specific examples of the optionally substituted C2-C5 alkoxycarbonyl group denoted by $R^6$ include the optionally substituted C2-C5 alkoxycarbonyl groups described in the description of $R^4$. $R^6$ is preferably a hydrogen atom, a 2-chloroethyl group, an amino group, a tert-butoxycarbonylamino group or a carboxy group in terms of a good yield.

Specific examples of the protecting group for nitrogen denoted by each of $R^7$ and $R^8$ in the general formula (4) include the protecting groups for nitrogen described in the description of $R^2$. Each of $R^7$ and $R^8$ is preferably a hydrogen atom or an acetyl group in terms of a good yield.

Specific examples of the optionally substituted C1-C6 alkyl group denoted by $R^9$ in the general formula (5) include the optionally substituted C1-C6 alkyl groups described in the description of $R^2$. Specific examples of the protecting group for nitrogen denoted by $R^9$ include the protecting groups for nitrogen described in the description of $R^2$. Specific examples of the pentose residues and analogs thereof denoted by $R^9$ include (P-1) to (P-401) described in the description of $R^3$. $R^9$ is preferably a hydrogen atom, a methyl group, (P-34), (P-35), (P-75), (P-100), (P-101), (P-123), (P-152), (P-153), (P-314) or (P-315) in terms of usefulness as a medical or agricultural chemical or an intermediate thereof.

Specific examples of the optionally substituted C1-C6 alkyl group denoted by $R^{10}$ in the general formula (5) include the optionally substituted C1-C6 alkyl groups described in the description of $R^2$. Specific examples of the optionally substituted amino group denoted by $R^{10}$ include the optionally substituted amino groups described in the description of $R^4$. Specific examples of the optionally substituted carbamoyl group denoted by $R^{10}$ include the optionally substituted carbamoyl groups described in the description of $R^4$. Specific examples of the optionally substituted C2-C5 alkoxycarbonyl group denoted by $R^{10}$ include the optionally substituted C2-C5 alkoxycarbonyl groups described in the description of $R^4$. $R^{10}$ is preferably a hydrogen atom, a 2-chloroethyl group, an amino group, a tert-butoxycarbonylamino group or a carboxy group in terms of a good yield.

Specific examples of the protecting group for nitrogen denoted by each of $R^{11}$ and $R^{12}$ in the general formula (5) include the protecting groups for nitrogen described in the description of $R^2$. Each of $R^{11}$ and $R^{12}$ is preferably a hydrogen atom or an acetyl group in terms of a good yield.

Specific examples of the optionally substituted C1-C6 alkyl group denoted by $R^{13}$ in the general formula (6) include the optionally substituted C1-C6 alkyl groups described in the description of $R^2$. Specific examples of the protecting group for nitrogen denoted by $R^{13}$ include the protecting groups for nitrogen described in the description of $R^2$. $R^{13}$ is preferably a hydrogen atom or a methyl group in terms of a good yield.

Specific examples of the optionally substituted C1-C6 alkyl group denoted by $R^{14}$ in the general formula (6) include the optionally substituted C1-C6 alkyl groups described in the description of $R^2$. Specific examples of the protecting group for nitrogen denoted by $R^{14}$ include the protecting groups for nitrogen described in the description of $R^2$. Specific examples of the pentose residues and analogs thereof denoted by $R^{14}$ include (P-1) to (P-401) described in the description of $R^3$. $R^{14}$ is preferably a hydrogen atom, a methyl group, (P-34), (P-35), (P-75), (P-100), (P-101), (P-123), (P-152), (P-153), (P-314) or (P-315) in terms of usefulness as a medial drug or an agricultural chemical or an intermediate thereof.

Specific examples of the protecting group for nitrogen denoted by each of $R^{15}$ and $R^{16}$ in the general formula (6) include the protecting group for nitrogen described in the description of $R^2$. Each of $R^{15}$ and $R^{16}$ is preferably a hydrogen atom or an acetyl group in terms of a good yield.

Specific examples of the optionally substituted C1-C6 alkyl group denoted by $R^{17}$ in the general formula (7) include the optionally substituted C1-C6 alkyl groups described in the description of $R^2$. Specific examples of the protecting group for nitrogen denoted by $R^{17}$ include the protecting groups for nitrogen described in the description of $R^2$. $R^{17}$ is preferably a hydrogen atom or a methyl group in terms of a good yield.

Specific examples of the optionally substituted C1-C6 alkyl group denoted by $R^{18}$ in the general formula (7) include the optionally substituted C1-C6 alkyl groups described in the description of $R^2$. Specific examples of the protecting group for nitrogen denoted by $R^{18}$ include the protecting groups for nitrogen described in the description of $R^2$. Specific examples of the pentose residues and analogs thereof denoted by $R^{18}$ include (P-1) to (P-401) described in the description of $R^3$. $R^{18}$ is preferably a hydrogen atom, a methyl group, (P-34), (P-35), (P-75), (P-100), (P-101), (P-123), (P-152), (P-153), (P-314) or (P-315) in terms of usefulness as a medical or agricultural chemical or an intermediate thereof.

Specific examples of the optionally substituted C1-C6 alkyl group denoted by $R^{19}$ in the general formula (8) include the optionally substituted C1-C6 alkyl groups described in the description of $R^2$. Specific examples of the protecting group for nitrogen denoted by $R^{19}$ include the protecting groups for nitrogen described in the description of $R^2$. $R^{19}$ is preferably a hydrogen atom or a methyl group in terms of a good yield.

Specific examples of the optionally substituted C1-C6 alkyl group denoted by $R^{20}$ in the general formula (8) include the optionally substituted C1-C6 alkyl groups described in the description of $R^2$. Specific examples of the protecting group for nitrogen denoted by $R^{20}$ include the protecting groups for nitrogen described in the description of $R^2$. Specific examples of the pentose residues and analogs thereof denoted by $R^{20}$ include (P-1) to (P-401) described in the description of $R^3$. $R^{20}$ is preferably a hydrogen atom, a methyl group, (P-34), (P-35), (P-75), (P-100), (P-101), (P-123), (P-152), (P-153), (P-314) or (P-315) in terms of usefulness as a medical or agricultural chemical or an intermediate thereof.

Specific examples of the optionally substituted C1-C6 alkyl group denoted by $R^{21}$ in the general formula (8) include the optionally substituted C1-C6 alkyl groups described in the description of $R^2$. Specific examples of the protecting group for nitrogen denoted by $R^{21}$ include the protecting groups for nitrogen described in the description of $R^2$. $R^{21}$ is preferably a hydrogen atom or a methyl group in terms of a good yield.

Specific examples of the optionally substituted C1-C6 alkyl group denoted by each of $R^{22}$ or $R^{23}$ in the general formula (9) include the optionally substituted C1-C6 alkyl groups described in the description of $R^2$. Each of $R^{22}$ and $R^{23}$ may be any one of the alkyl groups described above, and is preferably a methyl group or an ethyl group in terms of promising physiological activity. Specific examples of the optionally substituted C1-C6 alkyl group denoted by $R^{24}$ in the general formula (9) include the optionally substituted C1-C6 alkyl groups described in the description of $R^2$. Specific examples of the optionally substituted amino group denoted by $R^{24}$ include the optionally substituted amino groups described in the description of $R^4$. Specific examples of the optionally substituted C2-C5 alkoxycarbonyl group denoted by $R^{24}$ include the optionally substituted C2-C5 alkoxycarbonyl groups described in the description of $R^4$. $R^{24}$ is preferably a methyl group, an ethyl group, an amino group or an amino group substituted by a protecting group in terms of usefulness as a medical or agricultural chemical or an intermediate thereof.

Specific examples of the optionally substituted C1-C6 alkyl group denoted by each of $R^{25}$, $R^{26}$ and $R^{27}$ in the general formula (10) include the optionally substituted C1-C6 alkyl groups described in the description of $R^2$. Each of $R^{25}$, $R^{26}$ and $R^{27}$ is preferably a methyl group or an ethyl group in terms of promising performance as a sustained-release preparation.

Next, the production process of the present invention will be described in detail.

In a case where the uracils of the general formula (3) are used as a raw material, the production process is shown in the following [Process-A], and a 5-perfluoroalkyluracils represented by the general formula (11) are obtained.

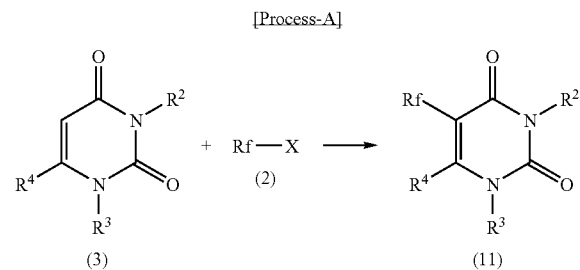

wherein $R^2$, $R^3$, $R^4$, Rf and X are the same as those described above.

In [Process-A], the sulfoxides (1) may be used as a solvent as they are, but it is also possible to use a solvent which does not adversely affect the reaction. Specific examples of the solvent include water, N,N-dimethylformamide, acetic acid, trifluoroacetic acid, tetrahydrofuran, diethyl ether, ethyl acetate, acetone, 1,4-dioxane, tert-butyl alcohol, ethanol, methanol, isopropyl alcohol, trifluoroethanol, hexamethylphosphoric triamide, N-methyl-2-pyrrolidone, N,N,N',N'-tetramethylurea, N,N'-dimethylpropyleneurea, and so on, and these may be used in combination properly. The solvent is preferably water, the sulfoxides (1), or a solvent mixture of water and the sulfoxides (1) in terms of a good yield.

The molar ratio of the uracils (3) and the sulfoxide (1) is preferably from 1:1 to 1:200, and more preferably from 1:10 to 1:100 in terms of a good yield.

The molar ratio of the uracils (3) and the perfluoroalkyl halides (2) is preferably from 1:1 to 1:100, and more preferably from 1:1.5 to 1:10 in terms of a good yield.

Examples of the peroxides include hydrogen peroxide, a hydrogen peroxide-urea composite, tert-butyl peroxide, peroxyacetic acid, and so on, and these may be used in combination properly. The peroxide is preferably hydrogen peroxide or a hydrogen peroxide-urea composite in terms of a good yield.

Hydrogen peroxide may be used after diluting it with water. On this occasion, the concentration can be from 3 to 70% by weight, but commercially available 35% by weight hydrogen peroxide may be used as it is. It is more preferable to dilute hydrogen peroxide with water to from 10 to 30% by weight in terms of a good yield and safety.

The molar ratio of the uracils (3) and the peroxides is preferably from 1:0.1 to 1:10, and more preferably from 1:1.5 to 1:3 in terms of a good yield.

The source of the iron compound is preferably an iron(II) salt in terms of a good yield and examples thereof include inorganic acid salts such as iron (II) sulfate, ammonium iron (II) sulfate, iron (II) tetrafluoroborate, iron (II) chloride, iron (II) bromide and iron (II) iodide, and organometallic compounds such as iron (II) acetate, iron (II) oxalate, bis(acetylacetonato)iron(II), ferrocene, and bis($\eta^5$-pentamethylcyclopentadieny)iron, and these may be used in combination properly. In addition, an iron powder, an iron(0) compound or an iron(I) salt may be used in combination with an oxidizing reagent such as a peroxide, so as to generate an iron(II) salt in the system. On this occasion, hydrogen peroxide used for the reaction may also be used as the oxidizing reagent as it is. The iron compound is preferably iron (II) sulfate, ammonium iron (II) sulfate, iron (II) tetrafluoroborate, ferrocene or an iron powder in terms of a good yield.

These iron compounds may be used in a solid state as they are, but they may also be used in the form of a solution. When they are used in the form of the solution, a solvent to be used may be any one of the sulfoxides (1) and the solvents as described above, and water is preferable among them. On this occasion, the concentration of the iron compound solution is preferably from 0.1 to 10 mol/l, and more preferably from 0.5 to 5 mol/l in terms of a good yield.

The molar ratio of the uracils (3) and the iron compounds is preferably from 1:0.01 to 1:10, and more preferably from 1:0.1 to 1:1 in terms of a good yield.

The reaction can be carried out at a temperature optionally selected from the range of from 20 to 100° C. The temperature is preferably from 20 to 70° C. in terms of a good yield.

In the case where the reaction is carried out in a closed system, the reaction can be carried out under a pressure optionally selected from the range of from the atmospheric pressure (0.1 MPa) to 1.0 MPa, and the reaction sufficiently proceeds even under the atmospheric pressure. Furthermore, an atmosphere in the reaction may be an inert gas such as argon or nitrogen, but the reaction sufficiently proceeds even in the atmosphere of air.

When the perfluoroalkyl halides of the general formula (2) are gas at room temperature, they may be used in a gaseous state as they are. On this occasion, they may be used as a gas mixture after diluting them with a gas such as argon, nitrogen, air, helium or oxygen, wherein a molar fraction of the perfluoroalkyl halides (2) are from 1 to 100%. In the case where the reaction is carried out in a closed system, the perfluoroalkyl halides (2) or the gas mixture thereof may be used as a reaction atmosphere. On this occasion, the pressure can be one optionally selected from the range of from the atmospheric pressure (0.1 MPa) to 1.0 MPa, but the reaction sufficiently proceeds even under the atmospheric pressure. On the other hand, the perfluoroalkyl halides (2) or the gas mixture thereof may be introduced by bubbling into a reaction solution in an open system. On this occasion, the introduction rate of the perfluoroalkyl halides (2) or the gas mixture thereof may be selected from the range of from 1 to 200 ml/min though it depends on a scale of the reaction, an amount of the catalyst, a temperature of the reaction, and a molar fraction of the perfluoroalkyl halides (2) in the gas mixture.

According to the process of the present invention, a yield of the desired product can be improved by addition of an acid. Examples of the acid include inorganic acids such as sulfuric acid, hydrochloric acid, hydrogen bromide, hydrogen iodide, nitric acid, phosphoric acid, hexafluorophosphoric acid and tetrafluoroboric acid, and organic acids such as formic acid, acetic acid, propionic acid, oxalic acid, p-toluenesulfonic acid, trifluoromethanesulfonic acid and trifluoroacetic acid. These may be used in combination properly. It is preferable to use sulfuric acid, tetrafluoroboric acid or trifluoromethanesulfonic acid in terms of a good yield.

In addition, an acid salt of sulfuric acid may also be used. Examples of the acid salt include tetramethylammonium hydrogen sulfate, tetraethylammonium hydrogen sulfate, tetrabutylammonium hydrogen sulfate, tetraphenylphosphonium hydrogen sulfate, and so on.

These acids may be used after diluting them. A solvent in that case may be selected from the sulfoxides (1) and the solvents as described above, and water, the sulfoxide compound (1) or a solvent mixture of water and the sulfoxide compound (1) is preferable among them.

The molar ratio of the uracils (3) and the acids is preferably from 1:0.001 to 1:5, and more preferably from 1:0.01 to 1:2 in terms of a good yield.

There are no particular restrictions on a method for isolating the desired product from the solution after the reaction, and the desired product can be obtained by one of the methods generally used such as solvent extraction, column chromatography, preparative thin-layer chromatography, preparative liquid chromatography, recrystallization and sublimation.

In a case where the cytosines of the general formula (4) are used as a raw material, the production process is shown in the following [Process-B], and a 5-perfluoroalkylcytosines represented by the general formula (12) are obtained.

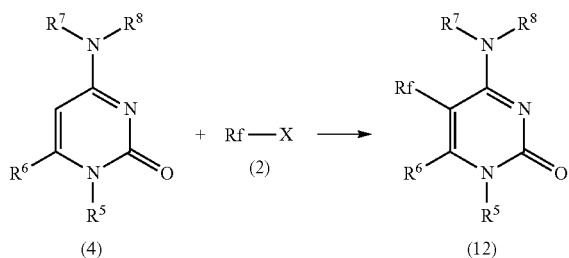

[Process-B]

wherein $R^5$, $R^6$, $R^7$, $R^8$, Rf and X are the same as those described above.

In [Process-B], the sulfoxides (1) may be used as a solvent as they are, but it is also possible to use a solvent which does not adversely affect the reaction. Specific examples of the solvent include water, N,N-dimethylformamide, acetic acid, trifluoroacetic acid, tetrahydrofuran, diethyl ether, ethyl acetate, acetone, 1,4-dioxane, tert-butyl alcohol, ethanol, methanol, isopropyl alcohol, trifluoroethanol, hexamethylphosphoric triamide, N-methyl-2-pyrrolidone, N,N,N',N'-tetramethylurea, N,N'-dimethylpropyleneurea, and so on, and these may be used in combination properly. The solvent is preferably water, the sulfoxides (1) or a solvent mixture of water and the sulfoxides (1) in terms of a good yield.

The molar ratio of the cytosines (4) and the sulfoxides (1) is preferably from 1:1 to 1:200, and more preferably from 1:10 to 1:100 in terms of a good yield.

The molar ratio of the cytosines (4) and the perfluoroalkyl halides (2) is preferably from 1:1 to 1:100, and more preferably from 1:1.5 to 1:10 in terms of a good yield.

Examples of the peroxides include hydrogen peroxide, a hydrogen peroxide-urea composite, tert-butyl peroxide, peroxyacetic acid, and so on, and these may be used in combination properly. The peroxide is preferably hydrogen peroxide in terms of a good yield.

Hydrogen peroxide may be used after diluting it with water. On this occasion, the concentration can be from 3 to 70% by weight, but commercially available 35% by weight hydrogen peroxide may be used as it is. It is more preferable to dilute hydrogen peroxide with water to from 10 to 30% by weight in terms of a good yield and safety.

The molar ratio of the cytosines (4) and the peroxides is preferably from 1:0.1 to 1:10, and more preferably from 1:1.5 to 1:3 in terms of a good yield.

The source of the iron compound is preferably an iron(II) salt in terms of a good yield and examples thereof include inorganic acid salts such as iron (II) sulfate, ammonium iron (II) sulfate, iron (II) tetrafluoroborate, iron (II) chloride, iron (II) bromide and iron (II) iodide, and organometallic compounds such as iron (II) acetate, iron (II) oxalate, bis(acetylacetonato)iron(II), ferrocene, and bis($\eta^5$-pentamethylcyclopentadienyl)iron, and these may be used in combination properly. In addition, an iron powder, an iron(0) compound or an iron(I) salt may be used in combination with an oxidizing reagent such as a peroxide, so as to generate an iron(II) salt in the system. On this occasion, hydrogen peroxide used for the reaction may also be used as the oxidizing reagent as it is. The iron compound is preferably iron (II) sulfate in terms of a good yield.

These iron compounds may be used in a solid state as they are, but they may also be used in the form of a solution. When they are used in the form of the solution, a solvent to be used may be any one of the sulfoxides (1) and the solvents as described above, and water is preferable among them. On this occasion, the concentration of the iron compound solution is preferably from 0.1 to 10 mol/l, and more preferably from 0.5 to 5 mol/l.

The molar ratio of the cytosines (4) and the iron compounds is preferably from 1:0.01 to 1:10, and more preferably from 1:0.1 to 1:1 in terms of a good yield.

The reaction can be carried out at a temperature optionally selected from the range of from 20 to 100° C. The temperature is preferably from 20 to 70° C. in terms of a good yield.

In the case where the reaction is carried out in a closed system, the reaction can be carried out under a pressure optionally selected from the range of from the atmospheric pressure (0.1 MPa) to 1.0 MPa, and the reaction sufficiently proceeds even under the atmospheric pressure. Furthermore, an atmosphere in the reaction may be an inert gas such as argon or nitrogen, but the reaction sufficiently proceeds even in the atmosphere of air.

When the perfluoroalkyl halides of the general formula (2) are gas at room temperature, they may be used in a gaseous state as they are. On this occasion, they may be used as a gas mixture after diluting them with a gas such as argon, nitrogen, air, helium or oxygen, wherein a molar fraction of the perfluoroalkyl halides (2) is from 1 to 100%. In the case where the reaction is carried out in a closed system, the perfluoroalkyl halides (2) or the gas mixture thereof may be used as a reaction atmosphere. On this occasion, the pressure can be one optionally selected from the range of from the atmospheric pressure (0.1 MPa) to 1.0 MPa, but the reaction sufficiently proceeds even under the atmospheric pressure. On the other hand, the perfluoroalkyl halides (2) or the gas mixture thereof may be introduced by bubbling into a reaction solution in an open system. On this occasion, the introduction rate of the perfluoroalkyl halides (2) or the gas mixture thereof may be selected from the range of from 1 to 200 ml/min though it depends on a scale of the reaction, an amount of the catalyst, a temperature of the reaction, and a molar fraction of the perfluoroalkyl halides (2) in the gas mixture.

According to the process of the present invention, a yield of the desired product can be improved by addition of an acid. Examples of the acid include inorganic acids such as sulfuric acid, hydrochloric acid, hydrogen bromide, hydrogen iodide, nitric acid, phosphoric acid, hexafluorophosphoric acid and tetrafluoroboric acid, and organic acids such as formic acid, acetic acid, propionic acid, oxalic acid, p-toluenesulfonic acid, trifluoromethanesulfonic acid and trifluoroacetic acid. These may be used in combination properly. It is preferable to use sulfuric acid in terms of a good yield.

These acids may be used after diluting them. A solvent in that case may be selected from the sulfoxides (1) and the solvents as described above, and water, the sulfoxides (1), or a solvent mixture of water and the sulfoxides (1) is preferable among them.

The molar ratio of the cytosines (4) and the acids is preferably from 1:0.001 to 1:5, and more preferably from 1:0.01 to 1:2 in terms of a good yield.

There are no particular restrictions on a method for isolating the desired product from the solution after the reaction, and the desired product can be obtained by one of the methods generally used such as solvent extraction, column chromatography, preparative thin-layer chromatography, preparative liquid chromatography, recrystallization and sublimation.

In a case where the adenines of the general formula (5) are used as a raw material, the production process is shown in the following [Process-C], and an 8-perfluoroalkyladenines represented by the general formula (13) are obtained.

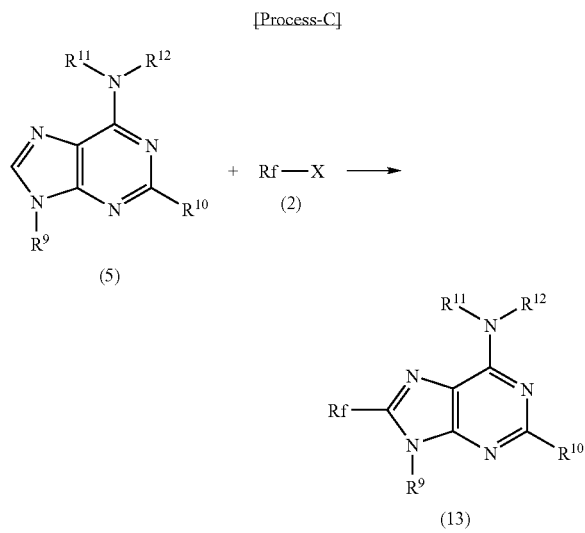

wherein $R^9$, $R^{10}$, $R^{11}$, $R^{12}$, Rf and X are the same as those described above.

In [Process-C], the sulfoxides (1) may be used as a solvent as they are, but it is also possible to use a solvent which does not adversely affect the reaction. Specific examples of the solvent include water, N,N-dimethylformamide, acetic acid, trifluoroacetic acid, tetrahydrofuran, diethyl ether, ethyl acetate, acetone, 1,4-dioxane, tert-butyl alcohol, ethanol, methanol, isopropyl alcohol, trifluoroethanol, hexamethylphosphoric triamide, N-methyl-2-pyrrolidone, N,N,N',N'-tetramethylurea, N,N'-dimethylpropyleneurea, and so on, and these may be used in combination properly. The solvent is preferably water, the sulfoxides (1) or a solvent mixture of water and the sulfoxides (1) in terms of a good yield.

The molar ratio of the adenines (5) and the sulfoxides (1) is preferably from 1:1 to 1:200, and more preferably from 1:10 to 1:100 in terms of a good yield.

The molar ratio of the adenines (5) and the perfluoroalkyl halides (2) is preferably from 1:1 to 1:100, and more preferably from 1:1.5 to 1:10 in terms of a good yield.

Examples of the peroxides include hydrogen peroxide, a hydrogen peroxide-urea composite, tert-butyl peroxide, peroxyacetic acid, and so on, and these may be used in combination properly. The peroxide is preferably hydrogen peroxide in terms of a good yield.

Hydrogen peroxide may be used after diluting it with water. On this occasion, the concentration can be from 3 to 70% by weight, but commercially available 35% by weight hydrogen peroxide may be used as it is. It is more preferable to dilute hydrogen peroxide with water to from 10 to 30% by weight in terms of a good yield and safety.

The molar ratio of the adenines (5) and the peroxides is preferably from 1:0.1 to 1:10, and more preferably from 1:1.5 to 1:3 in terms of a good yield.

The source of the iron compound is preferably an iron(II) salt in terms of a good yield and examples thereof include inorganic acid salts such as iron (II) sulfate, ammonium iron (II) sulfate, iron (II) tetrafluoroborate, iron (II) chloride, iron (II) bromide and iron (II) iodide, and organometallic compounds such as iron (II) acetate, iron (II) oxalate, bis(acetylacetonato)iron(II), ferrocene, and bis($\eta^5$-pentamethylcyclopentadienyl)iron, and these may be used in combination properly. In addition, an iron powder, an iron(0) compound or an iron(I) salt may be used in combination with an oxidizing reagent such as a peroxide, so as to generate an iron(II) salt in the system. On this occasion, hydrogen peroxide used for the reaction may also be used as the oxidizing reagent as it is. The iron compound is preferably iron (II) sulfate in terms of a good yield.

These iron compounds may be used in a solid state as they are, but they may also be used in the form of a solution. When they are used in the form of the solution, a solvent to be used may be any one of the sulfoxides (1) and the solvents as described above, and water is preferable among them. On this occasion, the concentration of the iron compound solution is preferably from 0.1 to 10 mol/l, and more preferably from 0.5 to 5 mol/l.

The molar ratio of the adenines (5) and the iron compounds is preferably from 1:0.01 to 1:10, and more preferably from 1:0.1 to 1:1 in terms of a good yield.

The reaction can be carried out at a temperature optionally selected from the range of from 20 to 100° C. The temperature is preferably from 20 to 70° C. in terms of a good yield.

In the case where the reaction is carried out in a closed system, the reaction can be carried out under a pressure optionally selected from the range of from the atmospheric pressure (0.1 MPa) to 1.0 MPa, and the reaction sufficiently proceeds even under the atmospheric pressure. Furthermore, an atmosphere in the reaction may be an inert gas such as argon or nitrogen, but the reaction sufficiently proceeds even in the atmosphere of air.

When the perfluoroalkyl halides of the general formula (2) are gas at room temperature, they may be used in a gaseous state as they are. On this occasion, it may be used as a gas mixture after diluting them with a gas such as argon, nitrogen, air, helium or oxygen, wherein a molar fraction of the perfluoroalkyl halides (2) is from 1 to 100%. In the case where the reaction is carried out in a closed system, the perfluoroalkyl halides (2) or the gas mixture thereof may be used as a reaction atmosphere. On this occasion, the pressure can be one optionally selected from the range of from the atmospheric pressure (0.1 MPa) to 1.0 MPa, but the reaction sufficiently proceeds even under the atmospheric pressure. On the other hand, the perfluoroalkyl halides (2) or the gas mixture thereof may be introduced by bubbling into a reaction solution in an open system. On this occasion, the introduction rate of the perfluoroalkyl halides (2) or the gas mixture thereof may be selected from the range of from 1 to 200 ml/min though it depends on a scale of the reaction, an amount of the catalyst, a temperature of the reaction, and a molar fraction of the perfluoroalkyl halides (2) in the gas mixture.

According to the process of the present invention, a yield of the desired product can be improved by addition of an acid. Examples of the acid include inorganic acids such as sulfuric acid, hydrochloric acid, hydrogen bromide, hydrogen iodide, nitric acid, phosphoric acid, hexafluorophosphoric acid and tetrafluoroboric acid, and organic acids such as formic acid, acetic acid, propionic acid, oxalic acid, p-toluenesulfonic acid, trifluoromethanesulfonic acid and trifluoroacetic acid. These may be used in combination properly. It is preferable to use sulfuric acid in terms of a good yield.

These acids may be used after diluting them. A solvent in that case may be selected from the sulfoxides (1) and the solvents as described above, and water, the sulfoxides (1), or a solvent mixture of water and the sulfoxides (1) is preferable among them.

The molar ratio of the adenines (5) and the acids is preferably from 1:0.001 to 1:5, and more preferably from 1:0.01 to 1:2 in terms of a good yield.

There are no particular restrictions on a method for isolating the desired product from the solution after the reaction, and the desired product can be obtained by one of the methods generally used such as solvent extraction, column chromatography, preparative thin-layer chromatography, preparative liquid chromatography, recrystallization and sublimation.

In a case where the guanines of the general formula (6) are used as a raw material, the production process is shown in the following [Process-D], and an 8-perfluoroalkylguanines represented by the general formula (14) are obtained.

[Process-D]

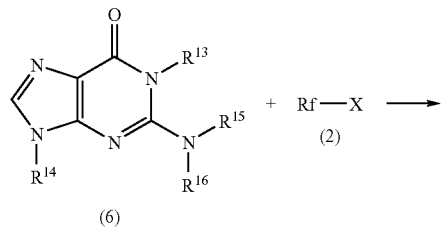

-continued

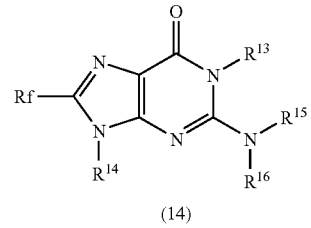

wherein $R^{13}$, $R^{14}$, $R^{15}$, $R^{16}$, Rf and X are the same as those described above.

In [Process-D], the sulfoxides (1) may be used as a solvent as they are, but it is also possible to use a solvent which does not adversely affect the reaction. Specific examples of the solvent include water, N,N-dimethylformamide, acetic acid, trifluoroacetic acid, tetrahydrofuran, diethyl ether, ethyl acetate, acetone, 1,4-dioxane, tert-butyl alcohol, ethanol, methanol, isopropyl alcohol, trifluoroethanol, hexamethylphosphoric triamide, N-methyl-2-pyrrolidone, N,N,N',N'-tetramethylurea, N,N'-dimethylpropyleneurea, and so on, and these may be used in combination properly. The solvent is preferably water, the sulfoxides (1) or a solvent mixture of water and the sulfoxides (1) in terms of a good yield.

The molar ratio of the guanines (6) and the sulfoxides (1) is preferably from 1:1 to 1:5000, and more preferably from 1:10 to 1:3000 in terms of a good yield.

The molar ratio of the guanines (6) and the perfluoroalkyl halides (2) is preferably from 1:1 to 1:100, and more preferably from 1:1.5 to 1:10 in terms of a good yield.

Examples of the peroxides include hydrogen peroxide, a hydrogen peroxide-urea composite, tert-butyl peroxide, peroxyacetic acid, and so on, and these may be used in combination properly. The peroxide is preferably hydrogen peroxide in terms of a good yield.

Hydrogen peroxide may be used after diluting it with water. On this occasion, the concentration can be from 3 to 70% by weight, but commercially available 35% by weight hydrogen peroxide may be used as it is. It is more preferable to dilute hydrogen peroxide with water to from 10 to 30% by weight in terms of a good yield and safety.

The molar ratio of the guanines (6) and the peroxides is preferably from 1:0.1 to 1:10, and more preferably from 1:1.5 to 1:3 in terms of a good yield.

The source of the iron compound is preferably an iron(II) salt in terms of a good yield and examples thereof include inorganic acid salts such as iron (II) sulfate, ammonium iron (II) sulfate, iron (II) tetrafluoroborate, iron (II) chloride, iron (II) bromide and iron (II) iodide, and organometallic compounds such as iron (II) acetate, iron (II) oxalate, bis(acetylacetonato)iron(II), ferrocene, and bis($\eta^5$-pentamethylcyclopentadienyl)iron, and these may be used in combination properly. In addition, an iron powder, an iron(0) compound or an iron(I) salt may be used in combination with an oxidizing reagent such as a peroxide, so as to generate an iron(II) salt in the system. On this occasion, hydrogen peroxide used for the reaction may also be used as the oxidizing reagent as it is. The iron compound is preferably iron (II) sulfate in terms of a good yield.

These iron compounds may be used in a solid state as they are, but they may also be used in the form of a solution. When they are used in the form of the solution, a solvent to be used may be any one of the sulfoxides (1) and the solvents as described above, and water is preferable among them. On this occasion, the concentration of the iron compound solution is preferably from 0.1 to 10 mol/l, and more preferably from 0.5 to 5 mol/l.

The molar ratio of the guanines (6) and the iron compounds is preferably from 1:0.01 to 1:10, and more preferably from 1:0.1 to 1:1 in terms of a good yield.

The reaction can be carried out at a temperature optionally selected from the range of from 20 to 100° C. The temperature is preferably from 20 to 70° C. in terms of a good yield.

In the case where the reaction is carried out in a closed system, the reaction can be carried out under a pressure optionally selected from the range of from the atmospheric pressure (0.1 MPa) to 1.0 MPa, and the reaction sufficiently proceeds even under the atmospheric pressure. Furthermore, an atmosphere in the reaction may be an inert gas such as argon or nitrogen, but the reaction sufficiently proceeds even in the atmosphere of air.

When the perfluoroalkyl halides of the general formula (2) are gas at room temperature, they may be used in a gaseous state as they are. On this occasion, it may be used as a gas mixture as diluted with a gas such as argon, nitrogen, air, helium or oxygen, wherein a molar fraction of the perfluoroalkyl halides (2) is from 1 to 100%. In the case where the reaction is carried out in a closed system, the perfluoroalkyl halides (2) or the gas mixture thereof may be used as a reaction atmosphere. On this occasion, the pressure can be one optionally selected from the range of from the atmospheric pressure (0.1 MPa) to 1.0 MPa, but the reaction sufficiently proceeds even under the atmospheric pressure. On the other hand, the perfluoroalkyl halides (2) or the gas mixture thereof may be introduced by bubbling into a reaction solution in an open system. On this occasion, the introduction rate of the perfluoroalkyl halides (2) or the gas mixture thereof may be selected from the range of from 1 to 200 ml/min though it depends on a scale of the reaction, an amount of the catalyst, a temperature of the reaction, and a molar fraction of the perfluoroalkyl halides (2) in the gas mixture.

According to the process of the present invention, a yield of the desired product can be improved by addition of an acid. Examples of the acid include inorganic acids such as sulfuric acid, hydrochloric acid, hydrogen bromide, hydrogen iodide, nitric acid, phosphoric acid, hexafluorophosphoric acid and tetrafluoroboric acid, and organic acids such as formic acid, acetic acid, propionic acid, oxalic acid, p-toluenesulfonic acid, trifluoromethanesulfonic acid and trifluoroacetic acid. These may be used in combination properly. It is preferable to use sulfuric acid in terms of a good yield.

These acids may be used after diluting them. A solvent in that case may be selected from the sulfoxides (1) and the solvents as described above, and water, the sulfoxides (1) or a solvent mixture of water and the sulfoxides (1) is preferable among them.

The molar ratio of the guanines (6) and the acids is preferably from 1:0.001 to 1:5, and more preferably from 1:0.01 to 1:2 in terms of a good yield.

There are no particular restrictions on a method for isolating the desired product from the solution after the reaction, and the desired product can be obtained by one of the methods generally used such as solvent extraction, column chromatography, preparative thin-layer chromatography, preparative liquid chromatography, recrystallization and sublimation.

In a case where the hypoxanthines of the general formula (7) are used as a raw material, the production process is shown in the following [Process-E], and an 8-perfluoroalkylhypoxanthines represented by the general formula (15) are obtained.

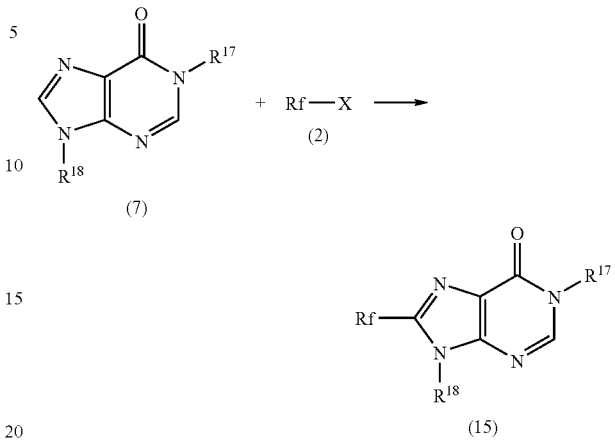

wherein $R^{17}$, $R^{18}$, Rf and X are the same as those described above.

In [Process-E], the sulfoxides (1) may be used as a solvent as they are, but it is also possible to use a solvent which does not adversely affect the reaction. Specific examples of the solvent include water, N,N-dimethylformamide, acetic acid, trifluoroacetic acid, tetrahydrofuran, diethyl ether, ethyl acetate, acetone, 1,4-dioxane, tert-butyl alcohol, ethanol, methanol, isopropyl alcohol, trifluoroethanol, hexamethylphosphoric triamide, N-methyl-2-pyrrolidone, N,N,N',N'-tetramethylurea, N,N'-dimethylpropyleneurea, and so on, and these may be used in combination properly. The solvent is preferably water, the sulfoxides (1) or a solvent mixture of water and the sulfoxides (1) in terms of a good yield.

The molar ratio of the hypoxanthines (7) and the sulfoxides (1) is preferably from 1:1 to 1:200, and more preferably from 1:10 to 1:100 in terms of a good yield.

The molar ratio of the hypoxanthines (7) and the perfluoroalkyl halides (2) is preferably from 1:1 to 1:100, and more preferably from 1:1.5 to 1:10 in terms of a good yield.

Examples of the peroxides include hydrogen peroxide, a hydrogen peroxide-urea composite, tert-butyl peroxide, peroxyacetic acid, and so on, and these may be used in combination properly. The peroxide is preferably hydrogen peroxide in terms of a good yield.

Hydrogen peroxide may be used after diluting it with water. On this occasion, the concentration may be from 3 to 70% by weight, but commercially available 35% by weight hydrogen peroxide may be used as it is. It is more preferable to dilute hydrogen peroxide with water to from 10 to 30% by weight in terms of a good yield and safety.

The molar ratio of the hypoxanthines (7) and the peroxides is preferably from 1:0.1 to 1:10, and more preferably from 1:1.5 to 1:3 in terms of a good yield.

The source of the iron compound is preferably an iron(II) salt in terms of a good yield and examples thereof include inorganic acid salts such as iron (II) sulfate, ammonium iron (II) sulfate, iron (II) tetrafluoroborate, iron (II) chloride, iron (II) bromide and iron (II) iodide, and organometallic compounds such as iron (II) acetate, iron (II) oxalate, bis(acetylacetonato)iron(II), ferrocene, and bis($\eta^5$-pentamethylcyclopentadieny)iron, and these may be used in combination properly. In addition, an iron powder, an iron(0) compound or an iron(I) salt may be used in combination with an oxidizing reagent such as a peroxide, so as to generate an iron(II) salt in the system. On this occasion, hydrogen peroxide used for the reaction may also be used as the oxidizing reagent as it is. The iron compound is preferably iron (II) sulfate or ferrocene in terms of a good yield.

These iron compounds may be used in a solid state as they are, but they may also be used in the form of a solution. When they are used in the form of the solution, a solvent to be used may be any one of the sulfoxides (1) and the solvents as described above, and water is preferable among them. On this occasion, the concentration of the iron compound solution is preferably from 0.1 to 10 mol/l, and more preferably from 0.5 to 5 mol/l.

The molar ratio of the hypoxanthines (7) and the iron compounds is preferably from 1:0.01 to 1:10, and more preferably from 1:0.1 to 1:1 in terms of a good yield.

The reaction can be carried out at a temperature optionally selected from the range of from 20 to 100° C. The temperature is preferably from 20 to 70° C. in terms of a good yield.

In the case where the reaction is carried out in a closed system, the reaction can be carried out under a pressure optionally selected from the range of from the atmospheric pressure (0.1 MPa) to 1.0 MPa, and the reaction sufficiently proceeds even under the atmospheric pressure. Furthermore, an atmosphere in the reaction may be an inert gas such as argon or nitrogen, but the reaction sufficiently proceeds even in the atmosphere of air.

When the perfluoroalkyl halides of the general formula (2) are gas at room temperature, they may be used in a gaseous state as they are. On this occasion, they may be used as a gas mixture as diluted with a gas such as argon, nitrogen, air, helium or oxygen, wherein a molar fraction of the perfluoroalkyl halides (2) is from 1 to 100%. In the case where the reaction is carried out in a closed system, the perfluoroalkyl halides (2) or the gas mixture thereof may be used as a reaction atmosphere. On this occasion, the pressure can be one optionally selected from the range of from the atmospheric pressure (0.1 MPa) to 1.0 MPa, but the reaction sufficiently proceeds even under the atmospheric pressure. On the other hand, the perfluoroalkyl halides (2) or the gas mixture thereof may be introduced by bubbling into a reaction solution in an open system. On this occasion, the introduction rate of the perfluoroalkyl halides (2) or the gas mixture thereof may be selected from the range of from 1 to 200 ml/min though it depends on a scale of the reaction, an amount of the catalyst, a temperature of the reaction, and a molar fraction of the perfluoroalkyl halides (2) in the gas mixture.

According to the process of the present invention, a yield of the desired product can be improved by addition of an acid. Examples of the acid include inorganic acids such as sulfuric acid, hydrochloric acid, hydrogen bromide, hydrogen iodide, nitric acid, phosphoric acid, hexafluorophosphoric acid and tetrafluoroboric acid, and organic acids such as formic acid, acetic acid, propionic acid, oxalic acid, p-toluenesulfonic acid, trifluoromethanesulfonic acid and trifluoroacetic acid. These may be used in combination properly. It is preferable to use sulfuric acid in terms of a good yield.

These acids may be used after diluting them. A solvent in that case may be selected from the sulfoxides (1) and the solvents as described above, and water, the sulfoxides (1) or a solvent mixture of water and the sulfoxides (1) is preferable among them.

The molar ratio of the hypoxanthines (7) and the acids is preferably from 1:0.001 to 1:5, and more preferably from 1:0.01 to 1:2 in terms of a good yield.

There are no particular restrictions on a method for isolating the desired product from the solution after the reaction, and the desired product can be obtained by one of generally used methods such as solvent extraction, column chromatography, preparative thin-layer chromatography, preparative liquid chromatography, recrystallization and sublimation.

In a case where the xanthines of the general formula (8) are used as a raw material, the production process is shown in the following [Process-F], and an 8-perfluoroalkylxanthines represented by the general formula (16) are obtained.

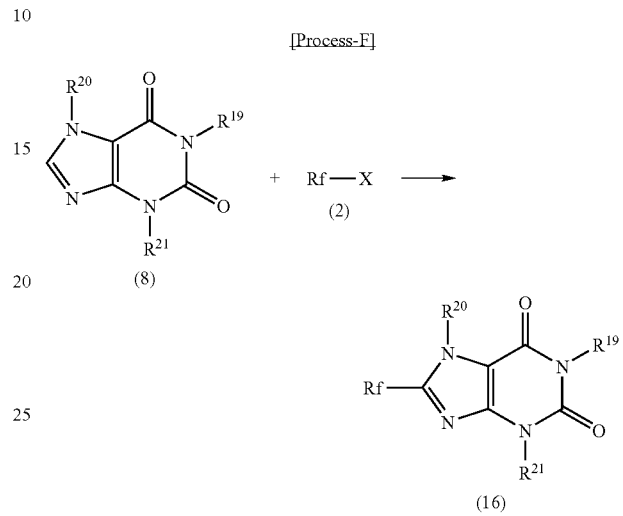

wherein $R^{19}$, $R^{20}$, $R^{21}$, Rf and X are the same as those described above.

In [Process-F], the sulfoxides (1) may be used as a solvent as they are, but it is also possible to use a solvent which does not adversely affect the reaction. Specific examples of the solvent include water, N,N-dimethylformamide, acetic acid, trifluoroacetic acid, tetrahydrofuran, diethyl ether, ethyl acetate, acetone, 1,4-dioxane, tert-butyl alcohol, ethanol, methanol, isopropyl alcohol, trifluoroethanol, hexamethylphosphoric triamide, N-methyl-2-pyrrolidone, N,N,N',N'-tetramethylurea, N,N'-dimethylpropyleneurea, and so on, and these may be used in combination properly. The solvent is preferably water, the sulfoxides (1) or a solvent mixture of water and the sulfoxides (1) in terms of a good yield.

The molar ratio of the xanthines (8) and the sulfoxides (1) is preferably from 1:1 to 1:5000, and more preferably from 1:10 to 1:1000 in terms of a good yield.

The molar ratio of the xanthines (8) and the perfluoroalkyl halides (2) is preferably from 1:1 to 1:100, and more preferably from 1:1.5 to 1:10 in terms of a good yield.

Examples of the peroxides include hydrogen peroxide, a hydrogen peroxide-urea composite, tert-butyl peroxide, peroxyacetic acid, and so on, and these may be used in combination properly. The peroxide is preferably hydrogen peroxide in terms of a good yield.

Hydrogen peroxide may be used after diluting it with water. On this occasion, the concentration can be from 3 to 70% by weight, but commercially available 35% by weight hydrogen peroxide may be used as it is. It is more preferable to dilute hydrogen peroxide with water to from 10 to 30% by weight in terms of a good yield and safety.

The molar ratio of the xanthines (8) and the peroxides is preferably from 1:0.1 to 1:10, and more preferably from 1:1.5 to 1:3 in terms of a good yield.

The source of the iron compound is preferably an iron(II) salt in terms of a good yield and examples thereof include inorganic acid salts such as iron (II) sulfate, ammonium iron (II) sulfate, iron (II) tetrafluoroborate, iron (II) chloride, iron (II) bromide and iron (II) iodide, and organometallic compounds such as iron (II) acetate, iron (II) oxalate, bis(acetylacetonato)iron(II), ferrocene, and bis($\eta^5$-pentamethylcyclopentadieny)iron, and these may be used in combination properly. In addition, an iron powder, an iron(0) compound or an iron(I) salt may be used in combination with an oxidizing reagent such as a peroxide, so as to generate an iron(II) salt in the system. On this occasion, hydrogen peroxide used for the reaction may also be used as the oxidizing reagent as it is. The iron compound is preferably iron (II) sulfate, iron (II) tetrafluoroborate, ferrocene or an iron powder in terms of a good yield.

These iron compounds may be used in a solid state as they are, but they may also be used in the form of a solution. When they are used in the form of the solution, a solvent to be used may be any one of the sulfoxides (1) and the solvents as described above, and water is preferable among them. On this occasion, the concentration of the iron compound solution is preferably from 0.1 to 10 mol/l, and more preferably from 0.5 to 5 mol/l.

The molar ratio of the xanthines (8) and the iron compounds is preferably from 1:0.01 to 1:10, and more preferably from 1:0.1 to 1:1 in terms of a good yield.

The reaction can be carried out at a temperature optionally selected from the range of from 20 to 100° C. The temperature is preferably from 20 to 70° C. in terms of a good yield.

In the case where the reaction is carried out in a closed system, the reaction can be carried out under a pressure optionally selected from the range of from the atmospheric pressure (0.1 MPa) to 1.0 MPa, and the reaction sufficiently proceeds even under the atmospheric pressure. Furthermore, an atmosphere in the reaction may be an inert gas such as argon or nitrogen, but the reaction sufficiently proceeds even in the atmosphere of air.

When the perfluoroalkyl halides of the general formula (2) are gas at room temperature, it may be used in a gaseous state as they are. On this occasion, they may be used as a gas mixture as diluted with a gas such as argon, nitrogen, air, helium or oxygen, wherein a molar fraction of the perfluoroalkyl halides (2) is from 1 to 100%. In the case where the reaction is carried out in a closed system, the perfluoroalkyl halides (2) or the gas mixture thereof may be used as a reaction atmosphere. On this occasion, the pressure can be one optionally selected from the range of from the atmospheric pressure (0.1 MPa) to 1.0 MPa, but the reaction sufficiently proceeds even under the atmospheric pressure. On the other hand, the perfluoroalkyl halides (2) or the gas mixture thereof may be introduced by bubbling into a reaction solution in an open system. On this occasion, the introduction rate of the perfluoroalkyl halides (2) or the gas mixture thereof may be selected from the range of from 1 to 200 ml/min though it depends on a scale of the reaction, an amount of the catalyst, a temperature of the reaction, and a molar fraction of the perfluoroalkyl halides (2) in the gas mixture.

According to the process of the present invention, a yield of the desired product can be improved by addition of an acid. Examples of the acid include inorganic acids such as sulfuric acid, hydrochloric acid, hydrogen bromide, hydrogen iodide, nitric acid, phosphoric acid, hexafluorophosphoric acid and tetrafluoroboric acid, and organic acids such as formic acid, acetic acid, propionic acid, oxalic acid, p-toluenesulfonic acid, trifluoromethanesulfonic acid and trifluoroacetic acid.

These may be used in combination properly. It is preferable to use sulfuric acid or tetrafluoroboric acid in terms of a good yield.

These acids may be used after diluting them. A solvent in that case may be selected from the sulfoxides (1) and the solvents as described above, and water, the sulfoxides (1) or a solvent mixture of water and the sulfoxide compound (1) is preferable among them.

The molar ratio of the xanthines (8) and the acids is preferably from 1:0.001 to 1:5, and more preferably from 1:0.01 to 1:2 in terms of a good yield.

There are no particular restrictions on a method for isolating the desired product from the solution after the reaction, and the desired product can be obtained by one of the methods generally used such as solvent extraction, column chromatography, preparative thin-layer chromatography, preparative liquid chromatography, recrystallization and sublimation.

Of the compounds obtained by the production process as described above, a 5-perfluoroalkyluracils represented by the general formula (9) and an 8-perfluoroalkylxanthines represented by the general formula (10) are novel compounds and are expected to be used as medical drugs or intermediates for medical and agricultural chemicals.

EXAMPLES

Now, the present invention will be described in detail with reference to examples, but it should be understood that the present invention is by no means restricted to these examples.

Example 1

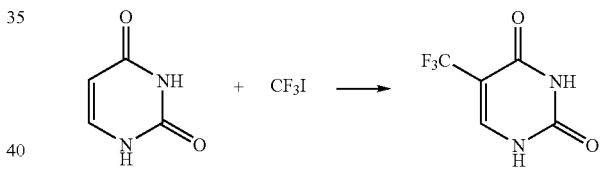

0.11 g (1.0 mmol) of uracil was weighed and placed in a 50 ml two-neck flask equipped with a magnetic rotor and the atmosphere in the flask was replaced with argon. The following materials were added thereinto: 2.0 ml of a 1N dimethyl sulfoxide solution, 1.0 ml of a 2.1 mol/l dimethyl sulfoxide solution of trifluoromethyl iodide, 0.2 ml of a 30% hydrogen peroxide aqueous solution and 0.3 ml of a 1.0 mol/l aqueous solution of iron (II) sulfate. The mixture was stirred at 40 to 50° C. for 20 minutes and then the resulting solution was cooled to room temperature. Formation of 5-trifluoromethyl uracil ($^{19}$F-NMR yield: 94%) was confirmed by $^{19}$F-NMR with 2,2,2-trifluoroethanol as an internal standard. 5-Trifluoromethyluracil was obtained as a white solid (0.17 g, yield: 93%) by preparative thin-layer chromatography.

$^1$H-NMR (deuterated acetone): δ8.09 (s, 1H), 10.5 (brs, 2H).

$^{13}$C-NMR (deuterated acetone): δ104.0 (q, $J_{CF}$=32.4 Hz), 123.6 (q, $J_{CF}$=268.2 Hz), 144.2 (q, $J_{CF}$=5.9 Hz), 150.9, 160.2.

$^{19}$F-NMR (deuterated acetone): δ-64.1.

MS (m/z): 180[M]$^+$.

Example 2

Formation of 5-trifluoromethyluracil ($^{19}$F-NMR yield: 80%) was confirmed in the same manner as in Example 1, except that a 1.0 mol/l of aqueous solution of ammonium iron (II) sulfate was used instead of the 1.0 mol/l of aqueous solution of iron (II) sulfate.

Example 3

0.11 g (1.0 mmol) of uracil and 0.028 g (0.5 mmol) of iron powder were weighed and placed in a 50 ml two-neck flask equipped with a magnetic rotor and the atmosphere in the flask was replaced with argon. The following materials were added thereinto: 2.0 ml of dimethyl sulfoxide, 2.0 ml of a 1N dimethyl sulfoxide solution of sulfuric acid, 1.0 ml of a 3.0 mol/l dimethyl sulfoxide solution of trifluoromethyl iodide and 0.2 ml of a 30% hydrogen peroxide aqueous solution. The mixture was stirred at 40 to 50° C. for 20 minutes and then the resulting solution was cooled to room temperature. Formation of 5-trifluoromethyluracil ($^{19}$F-NMR yield: 32%) was confirmed in the same manner as in Example 1.

Example 4

0.11 g (1.0 mmol) of uracil was weighed and placed in a 50 ml two-neck flask equipped with a magnetic rotor and the atmosphere in the flask was replaced with argon. The following materials were added thereinto: 0.21 ml of a 42% tetrafluoroboric acid aqueous solution, 2.0 ml of dimethyl sulfoxide, 3.0 ml of a 2.0 mol/l dimethyl sulfoxide solution of trifluoromethyl iodide, 0.3 ml of a 1.0 mol/l aqueous solution of iron (II) tetrafluoroborate and 0.2 ml of a 30% hydrogen peroxide aqueous solution. The mixture was stirred at 40 to 50° C. for 20 minutes and then the resulting solution was cooled to room temperature. Formation of 5-trifluoromethyluracil ($^{19}$F-NMR yield: 94%) was confirmed in the same manner as in Example 1.

Example 5

0.11 g (1.0 mmol) of uracil was weighed and placed in a 50 ml two-neck flask equipped with a magnetic rotor and the atmosphere in the flask was replaced with argon.

The following materials were added thereinto: 2.0 ml of a 1N dimethyl sulfoxide solution of sulfuric acid, 3.0 ml of a 2.0 mol/l dimethyl sulfoxide solution of trifluoromethyl iodide, 0.12 g of hydrogen peroxide-urea composite and 0.3 ml of a 1 mol/l aqueous solution of iron (II) sulfate. The mixture was stirred at 40 to 50° C. for 20 minutes and then the resulting solution was cooled to room temperature. Formation of 5-trifluoromethyl uracil ($^{19}$F-NMR yield: 70%) was confirmed in the same manner as in Example 1.

Example 6

Formation of 5-trifluoromethyluracil ($^{19}$F-NMR yield: 38%) was confirmed exactly in the same manner as in Example 1, except that dimethyl sulfoxide was used instead of the 1N dimethyl sulfoxide solution of sulfuric acid.

Example 7

0.11 g (1.0 mmol) of uracil was weighed and placed in a 50 ml two-neck flask equipped with a magnetic rotor and the atmosphere in the flask was replaced with trifluoromethyl iodide. The following materials were added thereinto: 5.0 ml of dibutyl sulfoxide, 0.053 ml of concentrated sulfuric acid, 0.2 ml of a 30% hydrogen peroxide aqueous solution and 0.3 ml of a 1.0 mol/l aqueous solution of iron (II) sulfate. The mixture was stirred at 40 to 50° C. for 20 minutes and then the resulting solution was cooled to room temperature. Formation of 5-trifluoromethyluracil ($^{19}$F-NMR yield: 0.2%) was confirmed by $^{19}$F-NMR with 2,2,2-trifluoroethanol as an internal standard.

Example 8

0.11 g (1.0 mmol) of uracil was weighed and placed in a 50 ml two-neck flask equipped with a magnetic rotor and the atmosphere in the flask was replaced with trifluoromethyl iodide. The following materials were added thereinto: 5.0 g of diphenyl sulfoxide, 0.053 ml of concentrated sulfuric acid, 0.2 ml of a 30% hydrogen peroxide aqueous solution and 0.3 ml of a 1.0 mol/l aqueous solution of iron (II) sulfate. The mixture was stirred at 40 to 50° C. for 20 minutes and then the resulting solution was cooled to room temperature. Formation of 5-trifluoromethyluracil ($^{19}$F-NMR yield: 0.5%) was confirmed by $^{19}$F-NMR with 2,2,2-trifluoroethanol as an internal standard.

Example 9

Formation of 5-trifluoromethyluracil ($^{19}$F-NMR yield: 76%) was confirmed exactly in the same manner as in Example 1, except that the reaction was carried out in the atmosphere of air without the replacement with argon.

Example 10

1.1 g (10 mmol) of uracil was weighed and placed in a 100 ml two-neck flask equipped with a magnetic rotor and the atmosphere in the flask was replaced with argon. The following materials were added thereinto: 20 ml of a 1N dimethyl sulfoxide solution of sulfuric acid, 22.5 ml of dimethyl sulfoxide, 7.5 ml of a 2.0 mol/l dimethyl sulfoxide solution of trifluoromethyl iodide, 2.0 ml of a 30% hydrogen peroxide aqueous solution and 3.0 ml of a 1.0 mol/l aqueous solution of iron (II) sulfate. The mixture was stirred at 40 to 50° C. for 30 minutes and then the resulting solution was cooled to room temperature. Formation of 5-trifluoromethyluracil ($^{19}$F-NMR yield: 94%) was confirmed in the same manner as in Example 1.

Example 11

1.1 g (10 mmol) of uracil was weighed and placed in a 100 ml two-neck flask equipped with a magnetic rotor and the atmosphere in the flask was replaced with argon. The following materials were added thereinto: 0.055 ml of concentrated sulfuric acid, 9 ml of dimethyl sulfoxide, 24.5 mmol of trifluoromethyl iodide, 2.0 ml of a 30% hydrogen peroxide aqueous solution and 1.5 ml of a 1.0 mol/l aqueous solution of iron (II) sulfate. The mixture was stirred at 60 to 70° C. for 10 minutes and then the resulting solution was cooled to room temperature. Formation of 5-trifluoromethyluracil ($^{19}$F-NMR yield: 97%) was confirmed in the same manner as in Example 1.

Example 12

11.2 g (100 mmol) of uracil was weighed and placed in a 300 ml two-neck flask equipped with a magnetic rotor and the atmosphere in the flask was replaced with argon. The following materials were added thereinto: 80 ml of dimethyl sulfoxide, 0.55 ml of concentrated sulfuric acid, 245 mmol of trifluoromethyl iodide, 20 ml of a 30% hydrogen peroxide aqueous solution and 10 ml of a 1.5 mol/l aqueous solution of iron (II) sulfate. The mixture was stirred at 60 to 70° C. for 100 minutes and then the resulting solution was cooled to room temperature. Formation of 5-trifluoromethyluracil ($^{19}$F-NMR yield: 97%) was confirmed in the same manner as in Example 1.

Example 13

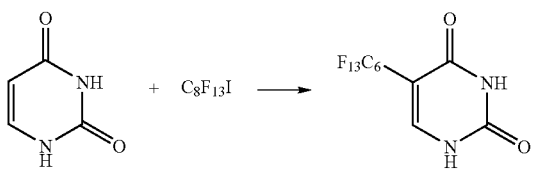

0.11 g (1.0 mmol) of uracil was weighed and placed in a 50 ml two-neck flask equipped with a magnetic rotor and the atmosphere in the flask was replaced with argon. The following materials were added thereinto: 2.0 ml of a 1N dimethyl sulfoxide solution of sulfuric acid, 1.3 ml of tridecafluoro-1-iodohexane, 1.2 ml of dimethyl sulfoxide, 0.3 ml of a 1.0 mol/l aqueous solution of iron (II) sulfate and 0.2 ml of a 30% hydrogen peroxide aqueous solution. The mixture was stirred at 40 to 50° C. for 20 minutes and then the resulting solution was cooled to room temperature. Formation of 5-perfluorohexyluracil ($^{19}$F-NMR yield: 29%) was confirmed by $^{19}$F-NMR with benzotrifluoride as an internal standard. 5-Perfluorohexyluracil was obtained as a white solid (0.107 g, yield: 25%) by column chromatography.

$^1$H-NMR (deuterated chloroform): δ8.01 (d, $J_{HF}$=5.7 Hz, 1H), 11.59 (brs, 1H), 11.80 (d, $J_{HF}$=4.8 Hz, 1H).

$^{19}$F-NMR (deuterated chloroform): δ−126.1 (q, $J_{FF}$=7.0 Hz, 2F), −122.8 (brs, 2F), −122.1 (brs, 2F), −121.2 (brs, 2F), −108.5 (m, 2F), −80.5 (t, $J_{FF}$=9.5 Hz, 3F)

MS (m/z): 430[M]$^+$.

Example 14

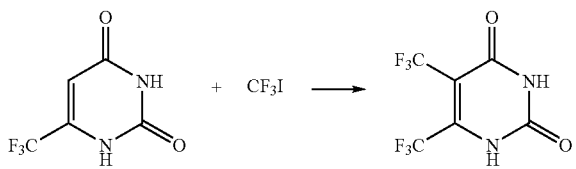

0.18 g (1.0 mmol) of 6-trifluoromethyluracil and 0.058 g (0.3 mmol) of ferrocene were weighed and placed in a 50 ml two-neck flask equipped with a magnetic rotor and the atmosphere in the flask was replaced with argon. The following materials were added thereinto: 1.8 ml of dimethyl sulfoxide, 2.0 ml of a 1N dimethyl sulfoxide solution of sulfuric acid, 1.0 ml of a 2.1 mol/l dimethyl sulfoxide solution of trifluoromethyl iodide and 0.2 ml of a 30% hydrogen peroxide aqueous solution. The mixture was stirred at 60 to 70° C. for 20 minutes and then the resulting solution was cooled to room temperature. Formation of 5,6-bis(trifluoromethyl)uracil ($^{19}$F-NMR yield: 63%) was confirmed by $^{19}$F-NMR with 2,2,2-trifluoroethanol as an internal standard. 5,6-Bis(trifluoromethyl)uracil was obtained as a white solid (0.12 g, yield: 48%) by preparative thin-layer chromatography.

$^1$H-NMR (deuterated acetone): δ10.73 (brs, 2H).

$^{13}$C-NMR (deuterated acetone): δ102.5 (q, $J_{CF}$=32.7 Hz), 120.6 (q, $J_{CF}$=277.3 Hz), 123.2 (q, $J_{CF}$=270.2 Hz), 147.0 (q, $J_{CF}$=37.0 Hz), 152.3, 161.2.

$^{19}$F-NMR (deuterated acetone): δ−64.8 (q, $J_{FF}$=14.6 Hz), −58.4 (q, $J_{FF}$=14.6 Hz).

MS (m/z): 248 [M]$^+$.

Example 15

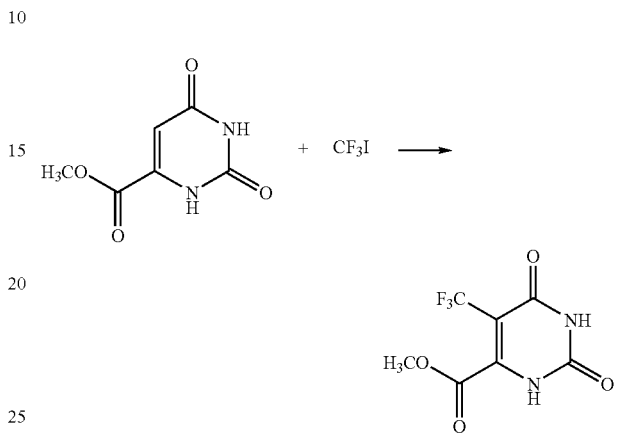

0.17 g (1.0 mmol) of 6-methoxycarbonyluracil and 0.058 g (0.3 mmol) of ferrocene were weighed and placed in a 50 ml two-neck flask equipped with a magnetic rotor and the atmosphere in the flask was replaced with argon.

The following materials were added thereinto: 1.8 ml of dimethyl sulfoxide, 2.0 ml of a 1N dimethyl sulfoxide solution of sulfuric acid, 1.0 ml of a 3.0 mol/l dimethyl sulfoxide solution of trifluoromethyl iodide and 0.2 ml of a 30% hydrogen peroxide aqueous solution. The mixture was stirred at 60 to 70° C. for 20 minutes and then the resulting solution was cooled to room temperature. Formation of 6-methoxycarbonyl-5-trifluoromethyluracil ($^{19}$F-NMR yield: 84%) was confirmed by $^{19}$F-NMR with 2,2,2-trifluoroethanol as an internal standard. 6-Methoxycarbonyl-5-trifluoromethyluracil was obtained as a white solid (0.20 g, yield: 80%) by column chromatography.

$^1$H-NMR (deuterated acetone): δ3.94 (s, 3H), 10.70 (s, 1H), 11.10 (brs, 1H).

$^{13}$C-NMR (deuterated acetone): δ54.5, 100.8 (q, $J_{CF}$=32.2 Hz), 123.1 (q, $J_{CF}$=269.7 Hz), 147.4 (q, $J_{CF}$=3.52 Hz), 149.9, 160.1, 161.6.

$^{19}$F-NMR (deuterated acetone): δ−60.6.

MS (m/z): 238[M]$^+$.

Example 16

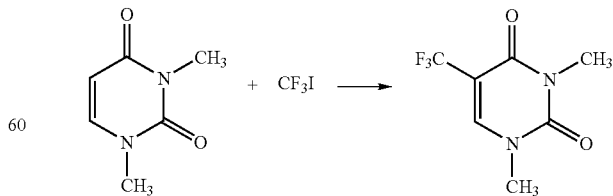

0.14 g (1.0 mmol) of 1,3-dimethyluracil was weighed and placed in a 50 ml two-neck flask equipped with a magnetic rotor and the atmosphere in the flask was replaced with argon.

The following materials were added thereinto: 2.0 ml of a 1N dimethyl sulfoxide solution of sulfuric acid, 1.0 ml of a 3.0 mol/l dimethyl sulfoxide solution of trifluoromethyl iodide, 0.2 ml of a 30% hydrogen peroxide aqueous solution and 0.3 ml of a 1.0 mol/l aqueous solution of iron (II) sulfate. The mixture was stirred at 40 to 50° C. for 20 minutes and then the resulting solution was cooled to room temperature. Formation of 1,3-dimethyl-5-trifluoromethyluracil ($^{19}$F-NMR yield: 78%) was confirmed by $^{19}$F-NMR with 2,2,2-trifluoroethanol as an internal standard. 1,3-Dimethyl-5-trifluoromethyluracil was obtained as a white solid (0.12 g, yield: 44%) by preparative thin-layer chromatography.

$^1$H-NMR (deuterated acetone): δ3.25 (s, 3H), 3.51 (s, 3H), 8.23 (q, $J_{HF}$=1.05 Hz, 1H).

$^{13}$C-NMR (deuterated acetone): δ27.8, 37.6, 102.9 (q, $J_{CF}$=32.3 Hz), 123.8 (q, $J_{CF}$=268.4 Hz), 146.4 (q, $J_{CF}$=5.91 Hz), 151.9, 159.5.

$^{19}$F-NMR (deuterated acetone): δ-60.6.

MS (m/z): 208 [M]$^+$.

Example 17

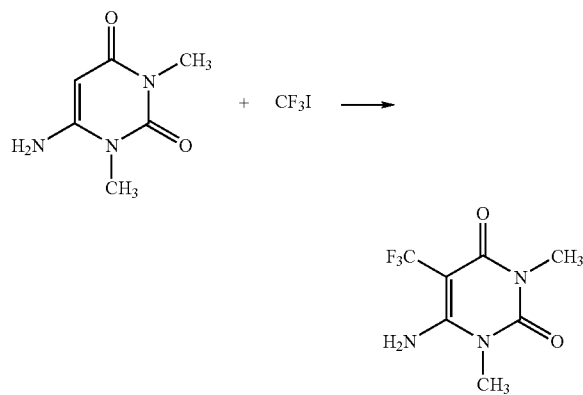

0.16 g (1.0 mmol) of 6-amino-1,3-dimethyluracil was weighed and placed in a 50 ml two-neck flask equipped with a magnetic rotor and the atmosphere in the flask was replaced with argon. The following materials were added thereinto: 2.0 ml of a 1N dimethyl sulfoxide solution of sulfuric acid, 1.0 ml of a 2.1 mol/l dimethyl sulfoxide solution of trifluoromethyl iodide, 0.2 ml of a 30% hydrogen peroxide aqueous solution and 0.3 ml of a 1.0 mol/l aqueous solution of iron (II) sulfate. The mixture was stirred at 40 to 50° C. for 20 minutes and then the resulting solution was cooled to room temperature. Formation of 6-amino-1,3-dimethyl-5-trifluoromethyluracil ($^{19}$F-NMR yield: 95%) was confirmed by $^{19}$F-NMR with 2,2,2-trifluoroethanol as an internal standard. 6-Amino-1,3-dimethyl-5-trifluoromethyluracil was obtained as a white solid (0.20 g, yield: 95%) by column chromatography.

$^1$H-NMR (deuterated chloroform): δ3.29 (s, 3H), 3.53 (s, 3H), 6.20 (s, 2H).

$^{13}$C-NMR (deuterated chloroform): δ28.0, 29.7, 80.5 (q, $J_{CF}$=30.2 Hz), 125.9 (q, $J_{CF}$=269.1 Hz), 150.4, 153.2, 159.8.

$^{19}$F-NMR (deuterated chloroform): δ-54.9.

MS (m/z): 223[M]$^+$.

Example 18

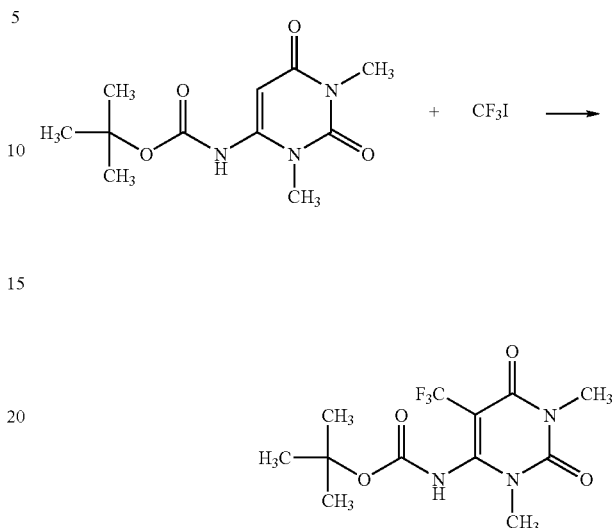

0.26 g (1.0 mmol) of 6-tert-butoxycarbonylamino-1,3-dimethyluracil was weighed and placed in a 50 ml two-neck flask equipped with a magnetic rotor and the atmosphere in the flask was replaced with argon. The following materials were added thereinto: 2.0 ml of a 1N dimethyl sulfoxide solution of sulfuric acid, 1.0 ml of a 2.1 mol/l dimethyl sulfoxide solution of trifluoromethyl iodide, 0.2 ml of a 30% hydrogen peroxide aqueous solution and 0.3 ml of a 1.0 mol/l aqueous solution of iron (II) sulfate. The mixture was stirred at 40 to 50° C. for 20 minutes and then the resulting solution was cooled to room temperature. Formation of 6-tert-butoxycarbonylamino-1,3-dimethyl-5-trifluoromethyluracil ($^{19}$F-NMR yield: 95%) was confirmed by $^{19}$F-NMR with 2,2,2-trifluoroethanol as an internal standard. 6-tert-Butoxycarbonylamino-1,3-dimethyl-5-trifluoromethyluracil was obtained as a white solid (0.30 g, yield: 93%) by column chromatography.

$^1$H-NMR (deuterated chloroform): δ1.51 (s, 9H), 3.32 (s, 3H), 3.46 (s, 3H), 6.89 (brs, 1H).

$^{13}$C-NMR (deuterated chloroform): δ27.9, 28.5, 32.2, 84.2, 98.4 (q, $J_{CF}$=22.8 Hz), 122.8 (q, $J_{CF}$=271.5 Hz), 147.5, 150.6, 151.3, 158.6.

$^{19}$F-NMR (deuterated chloroform): δ-54.8.

MS (m/z): 250[M−OC$_4$H$_9$]$^+$.

Example 19

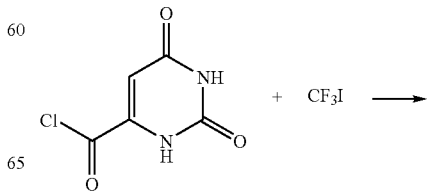

-continued

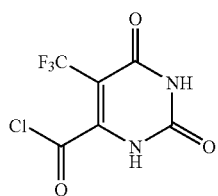

0.16 g (1.0 mmol) of 6-(2-chloromethyl)uracil and 0.058 g (0.3 mmol) of ferrocene were weighed and placed in a 50 ml two-neck flask equipped with a magnetic rotor and the atmosphere in the flask was replaced with argon. The following materials were added thereinto: 1.8 ml of dimethyl sulfoxide, 2.0 ml of a 1N dimethyl sulfoxide solution of sulfuric acid, 1.0 ml of a 2.1 mol/l dimethyl sulfoxide solution of trifluoromethyl iodide and 0.2 ml of a 30% hydrogen peroxide aqueous solution. The mixture was stirred at 60 to 70° C. for 20 minutes and then the resulting solution was cooled to room temperature. Formation of 6-(2-chloromethyl)-5-trifluoromethyluracil ($^{19}$F-NMR yield: 55%) was confirmed by $^{19}$F-NMR with 2,2,2-trifluoroethanol as an internal standard. 6-(2-Chloromethyl)-5-trifluoromethyluracil was obtained as a white solid (0.10 g, yield: 45%) by preparative thin-layer chromatography.

$^{1}$H-NMR (deuterated dimethyl sulfoxide): δ4.47 (s, 2H), 11.78 (brs, 1H), 11.82 (brs, 1H).

$^{13}$C-NMR (deuterated dimethyl sulfoxide): δ38.8, 100.9 (q, J$_{CF}$=30.7 Hz), 123.6 (q, J$_{CF}$=270.9 Hz), 150.3, 153.9, 160.9.

$^{19}$F-NMR (deuterated dimethyl sulfoxide): δ-56.5.

MS (m/z): 228 [M]$^{+}$.

Example 20

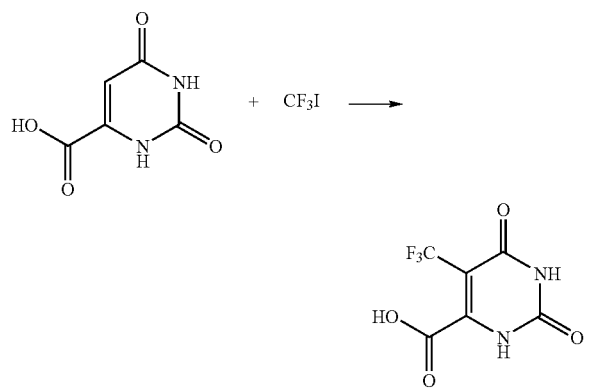

0.17 g (1.0 mmol) of 6-carboxyuracil and 0.058 g (0.3 mmol) of ferrocene were weighed and placed in a 50 ml two-neck flask equipped with a magnetic rotor and the atmosphere in the flask was replaced with argon. The following materials were added thereinto: 1.8 ml of dimethyl sulfoxide, 2.0 ml of a 1N dimethyl sulfoxide solution of sulfuric acid, 1.0 ml of a 3.0 mol/l dimethyl sulfoxide solution of trifluoromethyl iodide and 0.2 ml of a 30% hydrogen peroxide aqueous solution. The mixture was stirred at 60 to 70° C. for 20 minutes and then the resulting solution was cooled to room temperature. Formation of 6-carboxy-5-trifluoromethyluracil ($^{19}$F-NMR yield: 95%) was confirmed by $^{19}$F-NMR with 2,2,2-trifluoroethanol as an internal standard. 6-Carboxy-5-trifluoromethyluracil was obtained (0.076 g, yield: 34%) by column chromatography.

$^{1}$H-NMR (deuterated dimethyl sulfoxide): δ11.71 (brs, 1H), 12.13 (brs, 1H).

$^{13}$C-NMR (deuterated dimethyl sulfoxide): δ97.2 (q, J$_{CF}$=31.5 Hz), 122.9 (q, J$_{CF}$=269.9 Hz), 149.8, 150.3, 160.6, 162.3.

$^{19}$F-NMR (deuterated dimethyl sulfoxide): δ-58.6.

MS (m/z): 223[M−H]$^{+}$.

Example 21

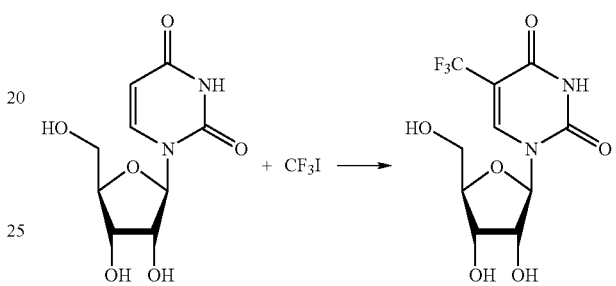

0.24 g (1.0 mmol) of uridine was weighed and placed in a 50 ml two-neck flask equipped with a magnetic rotor and the atmosphere in the flask was replaced with argon.

The following materials were added thereinto: 1.5 ml of dimethyl sulfoxide, 2 ml of a 1N dimethyl sulfoxide solution of sulfuric acid, 1 ml of a 3.0 mol/l dimethyl sulfoxide solution of trifluoromethyl iodide, 0.3 ml of a 1 mol/l aqueous solution of iron (II) sulfate and 0.2 ml of a 30% hydrogen peroxide aqueous solution. The mixture was stirred at 40 to 50° C. for 20 minutes and then the resulting solution was cooled to room temperature. Formation of 5-trifluoromethyluridine ($^{19}$F-NMR yield: 51%) was confirmed by $^{19}$F-NMR with 2,2,2-trifluoroethanol as an internal standard. 5-Trifluoromethyluridine was obtained (0.071 g, yield: 23%) by column chromatography.

$^{1}$H-NMR (deuterated dimethyl sulfoxide): δ2.84 (brs, 3H), 3.88 (m, 3H), 4.60 (m, 1H), 4.32 (d, J=13.6 Hz, 2H), 4.60 (brs, 1H), 5.88 (d, J=13.6 Hz, 1H), 8.88 (s, 1H).

$^{19}$F-NMR (deuterated dimethyl sulfoxide): δ-61.8.

Example 22

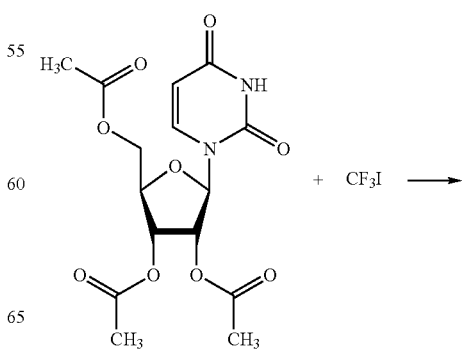

-continued

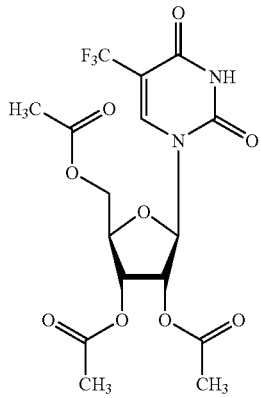

0.37 g (1.0 mmol) of 2',3',5'-tri-O-acetyluridine and 0.058 g (0.3 mmol) of ferrocene were weighed and placed in a 50 ml two-neck flask equipped with a magnetic rotor and the atmosphere in the flask was replaced with argon. The following materials were added thereinto: 1.8 ml of dimethyl sulfoxide, 2.0 ml of a 1N dimethyl sulfoxide solution of sulfuric acid, 1.0 ml of a 2.1 mol/l dimethyl sulfoxide solution of trifluoromethyl iodide and 0.2 ml of a 30% hydrogen peroxide aqueous solution. The mixture was stirred at 60 to 70° C. for 20 minutes and then the resulting solution was cooled to room temperature. Formation of 5-trifluoromethyl-2',3',5'-tri-O-acetyluridine ($^{19}$F-NMR yield: 45%) was confirmed by $^{19}$F-NMR with 2,2,2-trifluoroethanol as an internal standard. 5-Trifluoromethyl-2',3',5'-tri-O-acetyluridine was obtained as a white solid (0.17 g, yield: 40%) by column chromatography.

$^1$H-NMR (deuterated chloroform): δ2.11 (s, 3H), 2.13 (s, 3H), 2.14 (s, 3H), 4.34 (d, J=13.6 Hz, 1H), 4.43 (m, 1H), 4.43 (dd, J=3.2 Hz, 13.6 Hz, 1H), 5.34 (t, J=5.4 Hz, 1H), 5.37 (t, J=5.4 Hz, 1H), 6.07 (d, J=5.4 Hz, 1H), 8.01 (s, 1H), 9.48 (s, 1H).

$^{13}$C-NMR (deuterated chloroform): δ20.3, 20.4, 62.7, 69.9, 73.2, 80.5, 87.7, 106.2 (q, $J_{CF}$=33.3 Hz), 121.6 (q, $J_{CF}$=270.3 Hz), 140.2 (q, $J_{CF}$=6.0 Hz), 149.3, 158.0, 169.6, 169.7, 170.2.

$^{19}$F-NMR (deuterated chloroform): δ-64.0.

Example 23

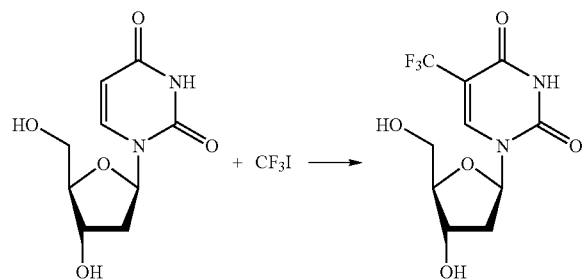

0.23 g (1.0 mmol) of 2'-deoxyuridine was weighed and placed in a 50 ml two-neck flask equipped with a magnetic rotor and the atmosphere in the flask was replaced with argon. The following materials were added thereinto: 2.0 ml of a 1N dimethyl sulfoxide solution of sulfuric acid, 1.0 ml of a 2.1 mol/l dimethyl sulfoxide solution of trifluoromethyl iodide, 0.2 ml of a 30% hydrogen peroxide aqueous solution and 0.3 ml of a 1.0 mol/l aqueous solution of iron (II) sulfate. The mixture was stirred at 40 to 50° C. for 20 minutes and then the resulting solution was cooled to room temperature. Formation of 5-trifluoromethyl-2'-deoxyuridine ($^{19}$F-NMR yield: 85%) was confirmed by $^{19}$F-NMR with 2,2,2-trifluoroethanol as an internal standard. 5-Trifluoromethyl-2'-deoxyuridine was obtained as a white solid (0.17 g, yield: 58%) by column chromatography.

$^1$H-NMR (deuterated chloroform): δ2.35 (ddd, J=60.10 Hz, 6.25 Hz, 13.53 Hz, 1H), 2.39 (ddd, J=3.61 Hz, 6.25 Hz, 13.53 Hz, 1H), 3.86 (dd, J=11.7 Hz, 15.3 Hz, 2H), 4.02 (dd, J=3.61 Hz, 6.10 Hz, 1H), 4.46 (brs, 2H), 4.53 (brs, 1H), 6.27 (t, J=6.25 Hz, 1H), 8.84 (s, 1H), 10.45 (s, 1H).

$^{13}$C-NMR (deuterated chloroform): δ42.0, 62.0, 71.4, 86.9, 89.0, 104.5 (q, $J_{CF}$=32.4 Hz), 123.7 (q, $J_{CF}$=268.6 Hz), 143.1 (q, $J_{CF}$=5.66 Hz), 150.5, 159.4.

$^{19}$F-NMR (deuterated chloroform): δ-63.7.

Example 24

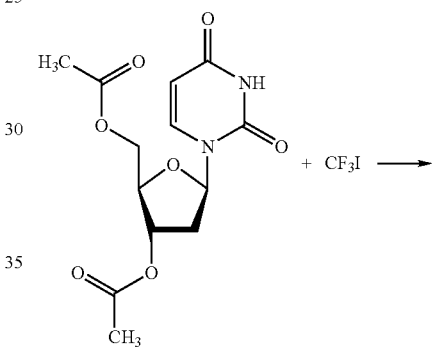

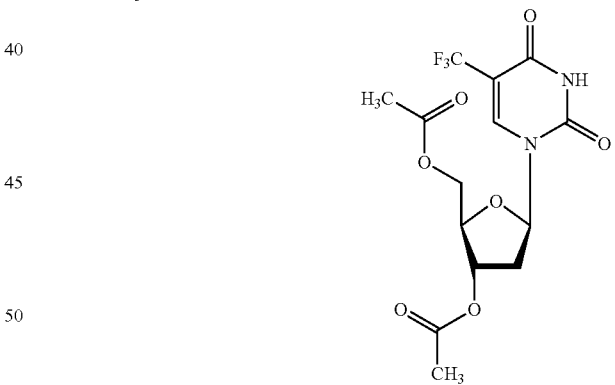

0.32 g (1.0 mmol) of 3',5'-di-O-acetyl-2'-deoxyuridine and 0.058 g (0.3 mmol) of ferrocene were weighed and placed in a 50 ml two-neck flask equipped with a magnetic rotor and the atmosphere in the flask was replaced with argon. The following materials were added thereinto: 1.8 ml of dimethyl sulfoxide, 2.0 ml of a 1N dimethyl sulfoxide solution of sulfuric acid, 1.0 ml of a 2.1 mol/l dimethyl sulfoxide solution of trifluoromethyl iodide and 0.2 ml of a 30% hydrogen peroxide aqueous solution. The mixture was stirred at 60 to 70° C. for 20 minutes and then the resulting solution was cooled to room temperature. Formation of 5-trifluoromethyl-3',5'-di-O-acetyl-2'-deoxyuridine ($^{19}$F-NMR yield: 75%) was confirmed by $^{19}$F-NMR with trifluoroethanol as an internal standard. 5-Trifluoromethyl-3',5'-di-O-acetyl-2'-deoxyuridine was obtained as a white solid (0.19 g, yield: 50%) by column chromatography.

$^1$H-NMR (deuterated chloroform): δ2.10 (s, 3H), 2.13 (s, 3H), 2.19 (ddd, J=6.63 Hz, 8.00 Hz, 14.34 Hz, 1H), 2.63 (ddd, J=1.96 Hz, 5.72 Hz, 14.34 Hz, 1H), 4.28-4.37 (m, 2H), 4.44 (dd, J=2.66 Hz, 11.77 Hz, 1H), 5.23 (td, J=1.96 Hz, 6.63 Hz, 1H), 6.28 (dd, J=5.72 Hz, 8.00 Hz, 1H), 8.09 (s, 1H), 9.27 (s, 1H).

$^{13}$C-NMR (deuterated chloroform): δ20.5, 20.9, 38.7, 63.7, 74.0, 83.1, 86.1, 105.7 (q, $J_{CF}$=33.3 Hz), 121.7 (q, $J_{CF}$=270.2 Hz), 140.0 (q, $J_{CF}$=5.91 Hz), 149.2, 158.1, 170.2, 170.4.

$^{19}$F-NMR (deuterated chloroform): δ-63.7.

Example 25

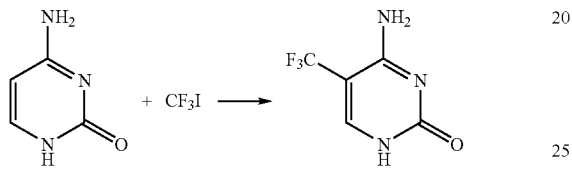

0.11 g (1.0 mmol) of cytosine was weighed and placed in a 50 ml two-neck flask equipped with a magnetic rotor and the atmosphere in the flask was replaced with argon. The following materials were added thereinto: 2.0 ml of dimethyl sulfoxide, 2.0 ml of a 1N dimethyl sulfoxide solution of sulfuric acid, 1.0 ml of a 3.0 mol/l dimethyl sulfoxide solution of trifluoromethyl iodide, 0.2 ml of a 30% hydrogen peroxide aqueous solution and 0.3 ml of a 1.0 mol/l aqueous solution of iron (II) sulfate. The mixture was stirred at 40 to 50° C. for 20 minutes and then the resulting solution was cooled to room temperature. Formation of 5-trifluoromethylcytosine ($^{19}$F-NMR yield: 27%) was confirmed by $^{19}$F-NMR with 2,2,2-trifluoroethanol as an internal standard. 5-Trifluoromethylcytosine was obtained as a white solid (0.010 g, yield: 5.6%) by column chromatography.

$^1$H-NMR (deuterated dimethyl sulfoxide): δ6.95 (brs, 2H), 7.72 (brs, 2H), 7.95 (s, 1H).

$^{13}$C-NMR (deuterated dimethyl sulfoxide): δ94.3 (q, $J_{CF}$=33.5 Hz), 124.2 (q, $J_{CF}$=268.7 Hz), 145.8, 156.0, 161.5.

$^{19}$F-NMR (deuterated dimethyl sulfoxide): δ-60.8.

MS (m/z): 181[M]$^+$.

Example 26

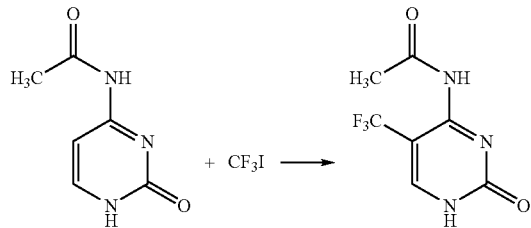

0.15 g (1.0 mmol) of N$^4$-acetylcytosine was weighed and placed in a 50 ml two-neck flask equipped with a magnetic rotor and the atmosphere in the flask was replaced with argon. The following materials were added thereinto: 17 ml of dimethyl sulfoxide, 2.0 ml of a 1N dimethyl sulfoxide solution of sulfuric acid, 1.0 ml of a 3.0 mol/l dimethyl sulfoxide solution of trifluoromethyl iodide, 0.2 ml of a 30% hydrogen peroxide aqueous solution and 0.3 ml of a 1.0 mol/l aqueous solution of iron (II) sulfate. The mixture was stirred at 40 to 50° C. for 20 minutes and then the resulting solution was cooled to room temperature. Formation of N$^4$-acetyl-5-trifluoromethylcytosine ($^{19}$F-NMR yield: 35%) was confirmed by $^{19}$F-NMR with 2,2,2-trifluoroethanol as an internal standard. N$^4$-acetyl-5-trifluoromethylcytosine was obtained as a white solid (0.067 g, yield: 30%) by column chromatography.

$^1$H-NMR (deuterated dimethyl sulfoxide): δ2.56 (s, 3H), 8.04 (s, 1H), 11.58 (brs, 2H).

$^{13}$C-NMR (deuterated dimethyl sulfoxide): δ23.0, 102.3 (q, $J_{CF}$=31.9 Hz), 123.4 (q, $J_{CF}$=268.8 Hz), 144.7 (q, $J_{CF}$=5.6 Hz), 151.2, 160.5, 172.1.

$^{19}$F-NMR (deuterated dimethyl sulfoxide): δ-61.8.

MS (m/z): 224[M+H]$^+$.

Example 27

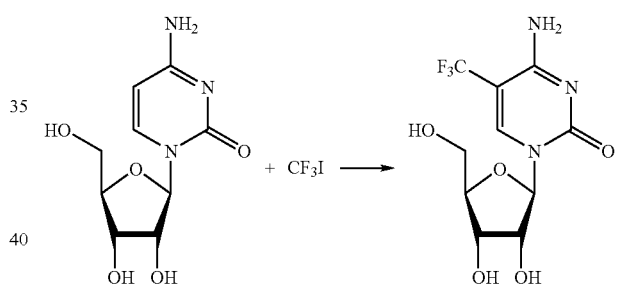

0.24 g (1.0 mmol) of cytidine was weighed and placed in a 50 ml two-neck flask equipped with a magnetic rotor and the atmosphere in the flask was replaced with argon. The following materials were added thereinto: 4.0 ml of dimethyl sulfoxide, 1.0 ml of a 3.0 mol/l dimethyl sulfoxide solution of trifluoromethyl iodide, 0.3 ml of a 1.0 mol/l aqueous solution of iron (II) sulfate and 0.2 ml of a 30% hydrogen peroxide aqueous solution. The mixture was stirred at 40 to 50° C. for 20 minutes and then the resulting solution was cooled to room temperature. Formation of 5-trifluoromethylcytidine ($^{19}$F-NMR yield: 24%) was confirmed by $^{19}$F-NMR with 2,2,2-trifluoroethanol as an internal standard. 5-Trifluoromethylcytidine was obtained (0.034 g, yield: 11%) by column chromatography.

$^1$H-NMR (deuterated dimethyl sulfoxide): δ3.52 (m, 1H), 3.70 (m, 1H), 3.96 (m, 3H), 5.00 (d, J=13.6 Hz, 1H), 5.28 (t, J=5.4 Hz, 1H), 5.48 (d, J=13.6 Hz, 1H), 5.76 (m, 1H), 7.16 (brs, 1H), 7.72 (brs, 2H), 8.84 (s, 1H)

$^{19}$F-NMR (deuterated dimethyl sulfoxide): δ-60.9. .

Example 28

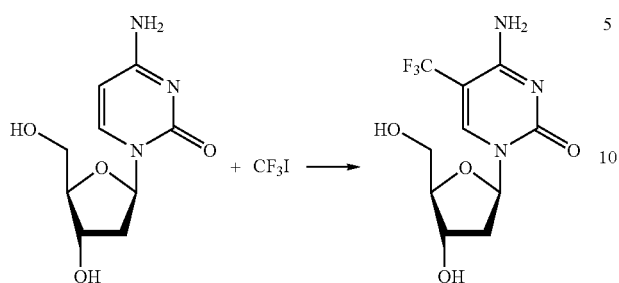

0.15 g (1.0 mmol) of 2'-deoxycytidine was weighed and placed in a 50 ml two-neck flask equipped with a magnetic rotor and the atmosphere in the flask was replaced with argon. The following materials were added thereinto: 2.0 ml of dimethyl sulfoxide, 2.0 ml of a 1N dimethyl sulfoxide solution of sulfuric acid, 1.0 ml of a 3.0 mol/l dimethyl sulfoxide solution of trifluoromethyl iodide, 0.2 ml of a 30% hydrogen peroxide aqueous solution and 0.3 ml of a 1.0 mol/l aqueous solution of iron (II) sulfate. The mixture was stirred at 40 to 50° C. for 20 minutes and then the resulting solution was cooled to room temperature. Formation of 5-trifluoromethyl-2'-deoxycytidine ($^{19}$F-NMR yield: 11%) was confirmed by $^{19}$F-NMR with 2,2,2-trifluoroethanol as an internal standard. 5-Trifluoromethyl-2'-deoxycytidine was obtained as a white solid (0.01 g, yield: 3.3%) by column chromatography.

$^1$H-NMR (deuterated dimethyl sulfoxide): δ2.16 (m, 2H), 3.62 (m, 2H), 3.82 (m, 1H), 4.20 (m, 1H), 5.06 (d, J=12.5 Hz, 1H), 5.19 (d, J=12.5 Hz, 1H), 6.04 (t, J=5.6 Hz, 1H), 7.04 (brs, 1H), 7.64 (brs, 2H), 8.60 (s, 1H).

$^{19}$F-NMR (deuterated dimethyl sulfoxide): δ-60.8.

Example 29

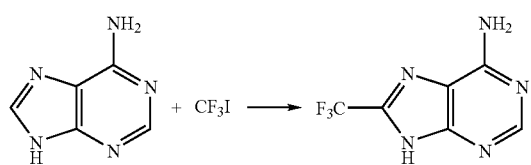

0.13 g (1.0 mmol) of adenine was weighed and placed in a 50 ml two-neck flask equipped with a magnetic rotor and the atmosphere in the flask was replaced with argon. The following materials were added thereinto: 2.0 ml of dimethyl sulfoxide, 2.0 ml of a 1N dimethyl sulfoxide solution of sulfuric acid, 1.0 ml of a 3.0 mol/l dimethyl sulfoxide solution of trifluoromethyl iodide, 0.2 ml of a 30% hydrogen peroxide aqueous solution and 0.3 ml of a 1.0 mol/l aqueous solution of iron (II) sulfate. The mixture was stirred at 40 to 50° C. for 20 minutes and then the resulting solution was cooled to room temperature. Formation of 8-trifluoromethyladenine ($^{19}$F-NMR yield: 26%) was confirmed by $^{19}$F-NMR with 2,2,2-trifluoroethanol as an internal standard. 8-Trifluoromethyladenine was obtained as a white solid (0.02 g, yield: 10%) by preparative thin-layer chromatography.

$^1$H-NMR (deuterated dimethyl sulfoxide): δ8.31 (s, 1H), 14.08 (brs, 2H).

$^{13}$C-NMR (deuterated dimethyl sulfoxide): δ119.9, 121.0 (q, $J_{CF}$=270.2 Hz), 147.1, 147.1, 150.9, 156.8.

$^{19}$F-NMR (deuterated dimethyl sulfoxide): δ-62.9.

MS (m/z): 203[M]$^+$

Example 30

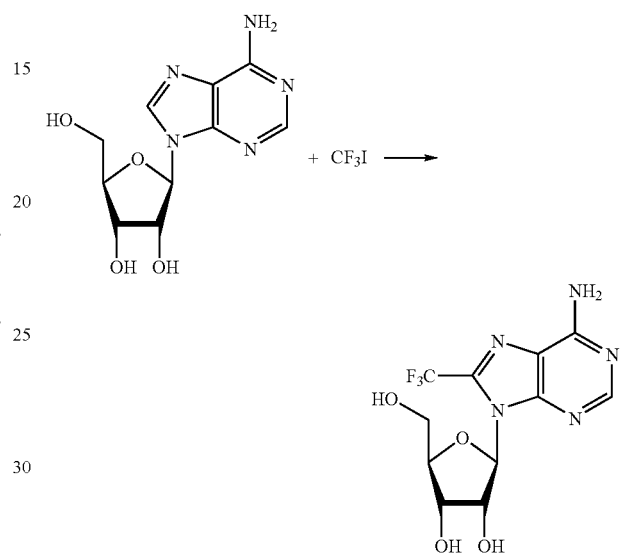

0.27 g (1.0 mmol) of adenosine was weighed and placed in a 50 ml two-neck flask equipped with a magnetic rotor and the atmosphere in the flask was replaced with argon. The following materials were added thereinto: 4.0 ml of dimethyl sulfoxide, 1.0 ml of a 3.0 mol/l dimethyl sulfoxide solution of trifluoromethyl iodide, 0.3 ml of a 1.0 mol/l aqueous solution of iron (II) sulfate and 0.2 ml of a 30% hydrogen peroxide aqueous solution. The mixture was stirred at 40 to 50° C. for 20 minutes and then the resulting solution was cooled to room temperature. Formation of 8-trifluoromethyladenosine ($^{19}$F-NMR yield: 6.7%) was confirmed by $^{19}$F-NMR with 2,2,2-trifluoroethanol as an internal standard. 8-Trifluoromethyladenosine was obtained as a white solid (0.01 g, yield: 3.1%) by column chromatography.

$^1$H-NMR (deuterated dimethyl sulfoxide): δ3.62 (m, 2H), 4.04 (m, 1H), 4.23 (m, 1H), 5.05 (dd, 1H), 5.24 (m, 1H), 5.52 (m, 2H), 5.81 (d, 1H), 7.92 (brs, 2H), 8.24 (s, 1H).

$^{19}$F-NMR (deuterated dimethyl sulfoxide): δ-60.2.

Example 31

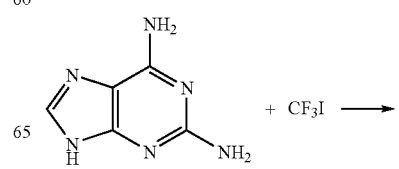

-continued

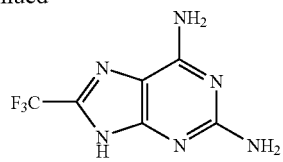

0.15 g (1.0 mmol) of 2,6-diaminopurine was weighed and placed in a 50 ml two-neck flask equipped with a magnetic rotor and the atmosphere in the flask was replaced with argon. The following materials were added thereinto: 4.0 ml of dimethyl sulfoxide, 1.0 ml of a 3.0 mol/l dimethyl sulfoxide solution of trifluoromethyl iodide, 0.3 ml of a 1.0 mol/l aqueous solution of iron (II) sulfate and 0.2 ml of a 30% hydrogen peroxide aqueous solution. The mixture was stirred at 40 to 50° C. for 20 minutes and then the resulting solution was cooled to room temperature. Formation of 2,6-diamino-8-trifluoromethylpurine ($^{19}$F-NMR yield: 45%) was confirmed by $^{19}$F-NMR with 2,2,2-trifluoroethanol as an internal standard. 2,6-Diamino-8-trifluoromethylpurine was obtained as a white solid (0.050 g, yield: 23%) by column chromatography.

$^1$H-NMR (deuterated dimethyl sulfoxide): δ6.17 (s, 2H), 7.26 (s, 2H), 12.2 (brs, 1H).

$^{13}$C-NMR (deuterated dimethyl sulfoxide): δ114.8, 116.0 (q, $J_{CF}$=269.1 Hz), 144.3, 152.7, 157.0, 161.7.

$^{19}$F-NMR (deuterated dimethyl sulfoxide): δ-62.6.

MS (m/z): 218[M]$^+$.

Example 32

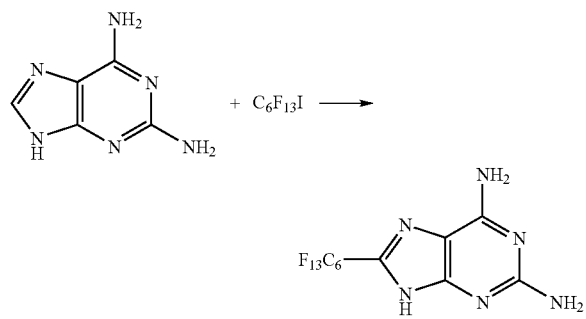

0.15 g (1.0 mmol) of 2,6-diaminopurine was weighed and placed in a 50 ml two-neck flask equipped with a magnetic rotor and the atmosphere in the flask was replaced with argon. The following materials were added thereinto: 3.0 ml of dimethyl sulfoxide, 2.0 ml of a 1N dimethyl sulfoxide solution of sulfuric acid, 1.3 ml of tridecafluoro-1-iodohexane, 0.3 ml of a 1.0 mol/l aqueous solution of iron (II) sulfate and 0.2 ml of a 30% hydrogen peroxide aqueous solution. The mixture was stirred at 40 to 50° C. for 20 minutes and then the resulting solution was cooled to room temperature. Formation of 2,6-diamino-8-perfluorohexylpurine ($^{19}$F-NMR yield: 10%) was confirmed by $^{19}$F-NMR with 2,2,2-trifluoroethanol as an internal standard. 2,6-Diamino-8-perfluorohexylpurine was obtained as a white solid (0.018 g, yield: 4.0%) by column chromatography.

$^1$H-NMR (deuterated dimethyl sulfoxide): δ6.20 (s, 2H), 7.31 (s, 2H), 12.2 (brs, 1H).

$^{19}$F-NMR (deuterated dimethyl sulfoxide): δ-126.2 (q, $J_{FF}$=4.7 Hz, 2F), -122.9 (brs, 2F), -121.9 (m, 4F), -108.9 (m, 2F), -80.7 (t, $J_{FF}$=9.5 Hz, 3F)

MS (m/z): 469[M+H]$^+$.

Example 33

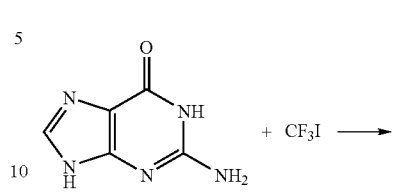

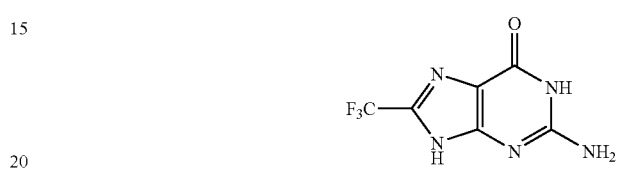

0.15 g (1.0 mmol) of guanine was weighed and placed in a 500 ml two-neck flask equipped with a magnetic rotor and the atmosphere in the flask was replaced with argon. The following materials were added thereinto: 197 ml of dimethyl sulfoxide, 2.0 ml of a 1N dimethyl sulfoxide solution of sulfuric acid, 1.0 ml of a 3.0 mol/l dimethyl sulfoxide solution of trifluoromethyl iodide, 0.2 ml of a 30% hydrogen peroxide aqueous solution and 0.3 ml of a 1.0 mol/l aqueous solution of iron (II) sulfate. The mixture was stirred at 40 to 50° C. for 20 minutes and then the resulting solution was cooled to room temperature. Formation of 8-trifluoromethylguanine ($^{19}$F-NMR yield: 46%) was confirmed by $^{19}$F-NMR with 2,2,2-trifluoroethanol as an internal standard. 8-Trifluoromethylguanine was obtained as a white solid (0.019 g, yield: 9%) by column chromatography.

$^1$H-NMR (deuterated dimethyl sulfoxide): δ6.60 (brs, 2H), 10.81 (brs, 1H), 13.73 (brs, 1H).

$^{13}$C-NMR (deuterated dimethyl sulfoxide): δ116.3, 119.2 (q, $J_{CF}$=269.3 Hz), 134.9 (q, $J_{CF}$=40.7 Hz), 152.8, 154.7, 156.6.

$^{19}$F-NMR (deuterated dimethyl sulfoxide): δ-63.0.

MS (m/z): 218[M–H].

Example 34

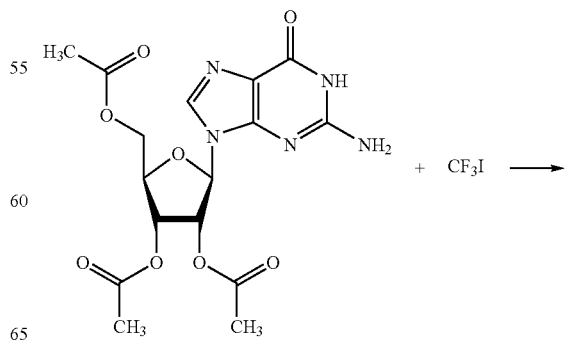

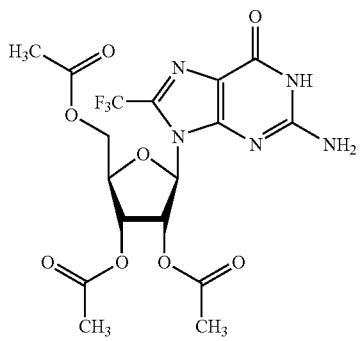

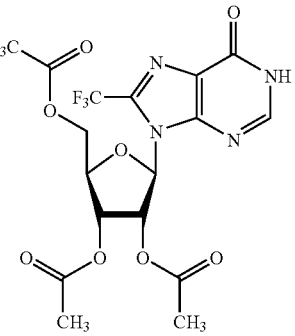

0.41 g (1.0 mmol) of 2',3',5'-tri-O-acetylguanosine was weighed and placed in a 50 ml two-neck flask equipped with a magnetic rotor and the atmosphere in the flask was replaced with argon. The following materials were added thereinto: 2.0 ml of dimethyl sulfoxide, 2.0 ml of a 1N dimethyl sulfoxide solution of sulfuric acid, 1.0 ml of a 3.0 mol/l of dimethyl sulfoxide solution of trifluoromethyl iodide, 0.3 ml of a 1.0 mol/l aqueous solution of iron (II) sulfate and 0.2 ml of a 30% hydrogen peroxide aqueous solution. The mixture was stirred at 40 to 50° C. for 20 minutes and then the resulting solution was cooled to room temperature. Formation of 8-trifluoromethyl-2',3',5'-tri-O-acetylguanosine ($^{19}$F-NMR yield: 51%) was confirmed by $^{19}$F-NMR with 2,2,2-trifluoroethanol as an internal standard. 8-Trifluoromethyl-2',3',5'-tri-O-acetylguanosine was obtained as a yellow solid (0.22 g, yield: 47%) by silica gel column chromatography.

$^1$H-NMR (deuterated chloroform): δ20.03 (s, 3H), 2.13 (s, 3H), 2.16 (s, 3H), 4.30 (m, 1H), 4.44 (m, 2H), 5.87 (t, J=5.0 Hz, 1H), 5.94 (d, J=5.0 Hz, 1H), 6.47 (brs, 2H), 12.1 (s, 1H).

$^{13}$C-NMR (deuterated chloroform): δ20.3, 20.5, 20.6, 62.9, 70.6, 71.6, 77.2, 80.6, 87.6, 116.4, 118.3 (q, $J_{CF}$=270.5 Hz), 152.6, 154.6, 158.9, 169.5, 169.5, 170.8.

$^{19}$F-NMR (deuterated chloroform): δ-61.5.

Example 35

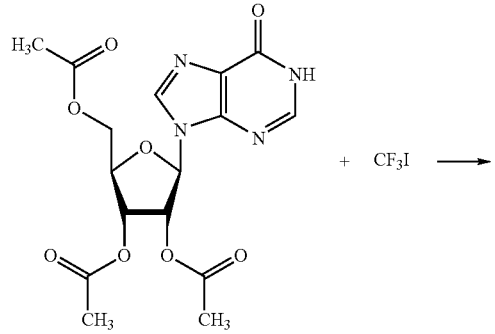

+ CF$_3$I →

0.39 g (1.0 mmol) of 2',3',5'-tri-O-acetylinosine was weighed and placed in a 50 ml two-neck flask equipped with a magnetic rotor and the atmosphere in the flask was replaced with argon. The following materials were added thereinto: 5.0 ml of dimethyl sulfoxide, 2.0 ml of a 1N dimethyl sulfoxide solution of sulfuric acid, 1.0 ml of a 3.0 mol/l of dimethyl sulfoxide solution of trifluoromethyl iodide, 0.3 ml of a 1.0 mol/l aqueous solution of iron (II) sulfate and 0.2 ml of a 30% hydrogen peroxide aqueous solution. The mixture was stirred at 40 to 50° C. for 20 minutes and then the resulting solution was cooled to room temperature. Formation of 8-trifluoromethyl-2',3',5'-tri-O-acetylinosine ($^{19}$F-NMR yield: 7.0%) was confirmed by $^{19}$F-NMR with 2,2,2-trifluoroethanol as an internal standard. 8-Trifluoromethyl-2',3',5'-tri-O-acetylinosine was obtained (0.018 g, yield: 4.0%) by column chromatography.

$^1$H-NMR (deuterated dimethyl sulfoxide): δ2.08 (s, 6H), 2.16 (s, 3H), 4.35-4.45 (m, 2H), 4.51 (dd, J=3.6, 11.3 Hz, 1H) 5.73 (dd, J=5.5, 5.6 Hz, 1H), 6.08 (d, J=5.5 Hz, 1H), 6.27 (dd, J=5.6 Hz, 1H), 8.26 (s, 1H), 12.49 (brs, 1H).

$^{13}$C-NMR (deuterated dimethyl sulfoxide): δ20.2, 20.5, 20.7, 62.8, 70.3, 72.0, 80.7, 88.0, 118.1 (q, $J_{CF}$=271.7 Hz), 124.2, 138.2 (q, $J_{CF}$=40.7 Hz), 147.2, 150.1, 158.6, 169.2, 169.5, 170.5.

$^{19}$F-NMR (deuterated dimethyl sulfoxide): δ-61.5.

Example 36

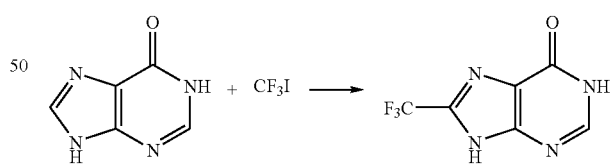

0.14 g (1.0 mmol) of hypoxanthine and 0.058 g (0.3 mmol) of ferrocene were weighed and placed in a 50 ml two-neck flask equipped with a magnetic rotor and the atmosphere in the flask was replaced with argon. The following materials were added thereinto: 2.0 ml of dimethyl sulfoxide, 2.0 ml of a 1N dimethyl sulfoxide solution of sulfuric acid, 1.0 ml of a 3.0 mol/l of dimethyl sulfoxide solution of trifluoromethyl iodide and 0.2 ml of a 30% hydrogen peroxide aqueous solution. The mixture was stirred at 60 to 70° C. for 20 minutes and then the resulting solution was cooled to room temperature. Formation of 8-trifluoromethylhypoxanthine ($^{19}$F-NMR yield: 24%) was confirmed by $^{19}$F-NMR with 2,2,2-trifluoroethanol as an internal standard. 8-Trifluoromethylhypoxanthine was obtained (0.026 g, yield: 13%) by column chromatography.

$^1$H-NMR (deuterated dimethyl sulfoxide): δ8.13 (s, 1H), 12.52 (s, 1H), 14.89 (brs, 1H).

$^{13}$C-NMR (deuterated dimethyl sulfoxide): δ119.0 (q, $J_{CF}$=270.1 Hz), 122.6, 138.0 (q, $J_{CF}$=41.2 Hz), 147.6, 152.3, 156.4.

$^{19}$F-NMR (deuterated dimethyl sulfoxide): δ-63.2.

MS (m/z): 205[M+H]$^+$.

Example 37

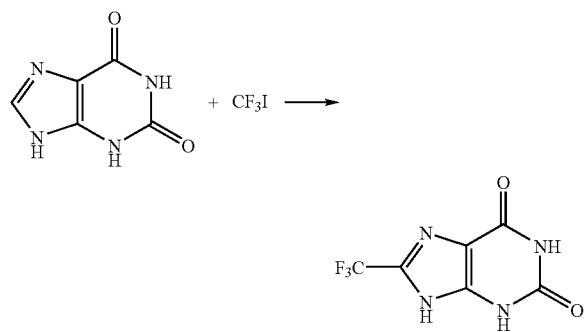

0.19 g (1.0 mmol) of xanthine was weighed and placed in a 100 ml two-neck flask equipped with a magnetic rotor and the atmosphere in the flask was replaced with argon.

The following materials were added thereinto: 47 ml of dimethyl sulfoxide, 2.0 ml of a 1N dimethyl sulfoxide solution of sulfuric acid, 1.0 ml of a 3.0 mol/l of dimethyl sulfoxide solution of trifluoromethyl iodide, 0.2 ml of a 30% hydrogen peroxide aqueous solution and 0.3 ml of a 1.0 mol/l aqueous solution of iron (II) sulfate. The mixture was stirred at 40 to 50° C. for 20 minutes and then the resulting solution was cooled to room temperature. Formation of 8-trifluoromethylxanthine ($^{19}$F-NMR yield: 44%) was confirmed by $^{19}$F-NMR with 2,2,2-trifluoroethanol as an internal standard. 8-Trifluoromethylxanthine was obtained (0.044 g, yield: 20%) by column chromatography.

$^1$H-NMR (deuterated dimethyl sulfoxide): δ11.16 (s, 1H), 11.83 (s, 1H), 15.07 (brs, 1H).

$^{13}$C-NMR (deuterated dimethyl sulfoxide): δ110.0, 118.7 (q, $J_{CF}$=269.9 Hz), 138.0 (q, $J_{CF}$=41.1 Hz), 148.1, 151.7, 156.2.

$^{19}$F-NMR (deuterated dimethyl sulfoxide): δ-63.1.

MS (m/z): 221[M+H]$^+$.

Example 38

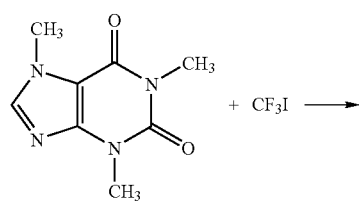

-continued

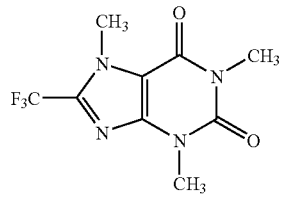

0.19 g (1.0 mmol) of caffeine was weighed and placed in a 50 ml two-neck flask equipped with a magnetic rotor and the atmosphere in the flask was replaced with argon.

The following materials were added thereinto: 2.0 ml of dimethyl sulfoxide, 2.0 ml of a 1N dimethyl sulfoxide solution of sulfuric acid, 1.0 ml of a 3.0 mol/l of dimethyl sulfoxide solution of trifluoromethyl iodide, 0.3 ml of a 1.0 mol/l aqueous solution of iron (II) sulfate and 0.2 ml of a 30% hydrogen peroxide aqueous solution. The mixture was stirred at 40 to 50° C. for 20 minutes and then the resulting solution was cooled to room temperature. Formation of 8-trifluoromethylcaffeine ($^{19}$F-NMR yield: 17%) was confirmed by $^{19}$F-NMR with 2,2,2-trifluoroethanol as an internal standard. 8-Trifluoromethylcaffeine was obtained as a white solid (0.033 g, yield: 13%) by column chromatography.

$^1$H-NMR (deuterated acetone): δ3.33 (s, 3H), 3.52 (s, 3H), 4.21 (q, $J_{HF}$=1.25 Hz, 3H).

$^{13}$C-NMR (deuterated acetone): δ27.8, 29.7, 33.3 (q, $J_{CF}$=1.98 Hz), 110.3, 119.2 (q, $J_{CF}$=270.2 Hz), 138.4 (q, $J_{CF}$=39.6 Hz), 147.0.

$^{19}$F-NMR (deuterated acetone): δ-62.1 (d, $J_{HF}$=1.25 Hz)

MS (m/z): 262[M]$^+$.

Example 39

Formation of 8-trifluoromethylcaffeine ($^{19}$F-NMR yield: 48%) was confirmed in the same manner as in Example 38, except that 0.5 ml of a 1N dimethyl sulfoxide solution of sulfuric acid was used instead of 2.0 ml of the 1N dimethyl sulfoxide solution of sulfuric acid.

Example 40

1.94 g (10 mmol) of caffeine was weighed and placed in a 100 ml two-neck flask equipped with a magnetic rotor and the atmosphere in the flask was replaced with argon.

The following materials were added thereinto: 20 ml of dimethyl sulfoxide, 20 ml of a 1N dimethyl sulfoxide solution of sulfuric acid, 10 ml of a 3.0 mol/l dimethyl sulfoxide solution of trifluoromethyl iodide, 3.0 ml of a 1.0 mol/l aqueous solution of iron (II) sulfate and 2.0 ml of a 30% hydrogen peroxide aqueous solution. The mixture was stirred at 50 to 60° C. for 60 minutes and then the resulting solution was cooled to room temperature. Formation of 8-trifluoromethylcaffeine ($^{19}$F-NMR yield: 20%) was confirmed by $^{19}$F-NMR with 2,2,2-trifluoroethanol as an internal standard.

Example 41

1.94 g (10 mmol) of caffeine was weighed and placed in a 300 ml two-neck flask equipped with a magnetic rotor and the atmosphere in the flask was replaced with argon.

The following materials were added thereinto: 50 ml of dimethyl sulfoxide, 0.055 ml of concentrated sulfuric acid, 30 mmol of gaseous trifluoromethyl iodide, 3.0 ml of a 1.0 mol/l aqueous solution of iron (II) sulfate and 2.0 ml of a 30% hydrogen peroxide aqueous solution. The mixture was stirred at 50 to 60° C. for 60 minutes and then the resulting solution was cooled to room temperature. Formation of 8-trifluoromethylcaffeine ($^{19}$F-NMR yield: 23%) was confirmed by $^{19}$F-NMR with 2,2,2-trifluoroethanol as an internal standard.

Example 42

Formation of 8-trifluoromethylcaffeine ($^{19}$F-NMR yield: 15%) was confirmed in the same manner as in Example 41, except that a 1.0 mol/l aqueous solution of ammonium iron (II) sulfate was used instead of the 1.0 mol/l aqueous solution of iron (II) sulfate.

Example 43

0.19 g (1.0 mmol) of caffeine was weighed and placed in a 50 ml two-neck flask equipped with a magnetic rotor and the atmosphere in the flask was replaced with argon.
The following materials were added thereto: 0.21 ml of a 42% tetrafluoroboric acid aqueous solution, 4.0 ml of dimethyl sulfoxide, 1.0 ml of a 3.0 mol/l dimethyl sulfoxide solution of trifluoromethyl iodide, 0.3 ml of a 1.0 mol/l aqueous solution of iron (II) tetrafluoroborate and 0.2 ml of a 30% hydrogen peroxide aqueous solution. The mixture was stirred at 40 to 50° C. for 20 minutes and then the resulting solution was cooled to room temperature. Formation of 8-trifluoromethylcaffeine ($^{19}$F-NMR yield: 11%) was confirmed by $^{19}$F-NMR with 2,2,2-trifluoroethanol as an internal standard.

Example 44

0.19 g (1.0 mmol) of caffeine was weighed and placed in a 50 ml two-neck flask equipped with a magnetic rotor and the atmosphere in the flask was replaced with argon. The following materials were added thereto: 0.016 g (0.3 mmol) of iron powder, 2.0 ml of dimethyl sulfoxide, 2.0 ml of a 1N dimethyl sulfoxide solution of sulfuric acid, 1.0 ml of a 3.0 mol/l dimethyl sulfoxide solution of trifluoromethyl iodide and 0.2 ml of a 30% hydrogen peroxide aqueous solution. The mixture was stirred at 40 to 50° C. for 20 minutes and then the resulting solution was cooled to room temperature. Formation of 8-trifluoromethylcaffeine ($^{19}$F-NMR yield: 37%) was confirmed by $^{19}$F-NMR with 2,2,2-trifluoroethanol as an internal standard.

Example 45

0.19 g (1.0 mmol) of caffeine and 0.056 g (0.3 mmol) of ferrocene were weighed and placed in a 50 ml two-neck flask equipped with a magnetic rotor and the atmosphere in the flask was replaced with argon. The following materials were added thereto: 2.0 ml of dimethyl sulfoxide, 2.0 ml of a 1N dimethyl sulfoxide solution of sulfuric acid, 1.0 ml of a 3.0 mol/l of dimethyl sulfoxide solution of trifluoromethyl iodide, 0.3 ml of a 1.0 mol/l aqueous solution of iron (II) sulfate and 0.2 ml of a hydrogen peroxide aqueous solution. The mixture was stirred at 40 to 50° C. for 20 minutes and then the resulting solution was cooled to room temperature. Formation of 8-trifluoromethylcaffeine ($^{19}$F-NMR yield: 17%) was confirmed by $^{19}$F-NMR with 2,2,2-trifluoroethanol as an internal standard.

Example 46

Formation of 8-trifluoromethylcaffeine ($^{19}$F-NMR yield: 13%) was confirmed in the same manner as in Example 41 except that the reaction was carried out in the atmosphere of air without the replacement with argon.

Example 47

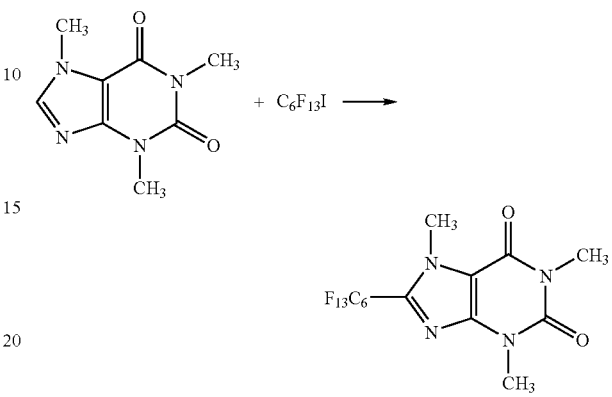

0.18 g (1.0 mmol) of caffeine was weighed and placed in a 50 ml two-neck flask equipped with a magnetic rotor and the atmosphere in the flask was replaced with argon. The following materials were added thereto: 3.0 ml of dimethyl sulfoxide, 2.0 ml of a 1N dimethyl sulfoxide solution of sulfuric acid, 1.3 ml of tridecafluoro-1-iodohexane, 0.3 ml of a 1.0 mol/l aqueous solution of iron (II) sulfate and 0.2 ml of a 30% hydrogen peroxide aqueous solution. The mixture was stirred at 40 to 50° C. for 20 minutes and then the resulting solution was cooled to room temperature. Formation of 8-perfluorohexylcaffeine ($^{19}$F-NMR yield: 30%) was confirmed by $^{19}$F-NMR with 2,2,2-trifluoroethanol as an internal standard. 8-Perfluorohexylcaffeine was obtained as a white solid (0.077 g, yield: 15%) by column chromatography.

$^{1}$H-NMR (deuterated acetone): δ3.33 (s, 3H), 3.52 (s, 3H), 4.21 (s, 3H).

$^{19}$F-NMR (deuterated acetone): δ-125.9 (m, 2F), -122.8 (s, 2F), -122.0 (m, 2F), -114.2 (m, 4F), -80.5 (q, $J_{FF}$=9.4 Hz, 3F).

MS (m/z): 513[M+H]$^+$.

Example 48

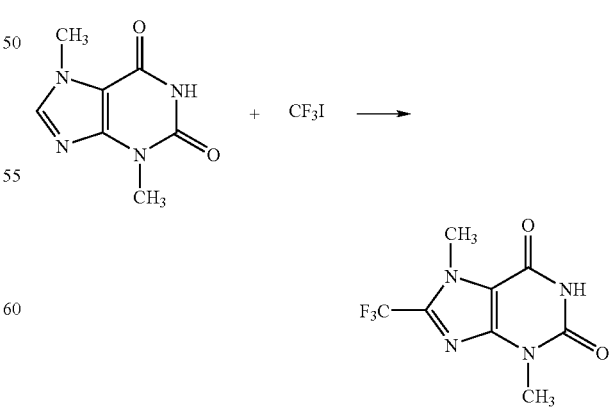

0.18 g (1.0 mmol) of theobromine was weighed and placed in a 50 ml two-neck flask equipped with a magnetic rotor and the atmosphere in the flask was replaced with argon. The following materials were added thereinto: 17 ml of dimethyl sulfoxide, 2.0 ml of a 1N dimethyl sulfoxide solution of sulfuric acid, 1.0 ml of a 3.0 mol/l dimethyl sulfoxide solution of trifluoromethyl iodide, 0.3 ml of a 1.0 mol/l aqueous solution of iron (II) sulfate and 0.2 ml of a 30% hydrogen peroxide aqueous solution. The mixture was stirred at 40 to 50° C. for 20 minutes and then the resulting solution was cooled to room temperature. Formation of 8-trifluoromethyltheobromine ($^{19}$F-NMR yield: 12%) was confirmed by $^{19}$F-NMR with 2,2,2-trifluoroethanol as an internal standard. 8-Trifluoromethyltheobromine was obtained as a white solid (0.024 g, yield: 10%) by column chromatography.

$^1$H-NMR (deuterated dimethyl sulfoxide): δ3.34 (s, 3H), 4.04 (s, J=1.7 Hz, 3H), 11.48 (brs, 1H).

$^{13}$C-NMR (deuterated dimethyl sulfoxide): δ33.1 (q, $J_{CF}$=1.9 Hz), 42.1, 109.9 (q, $J_{CF}$=1.9 Hz), 118.2 (q, $J_{CF}$=270.7 Hz), 137.0 (q, $J_{CF}$=39.2 Hz), 147.5, 150.6, 155.2.

$^{19}$F-NMR (deuterated dimethyl sulfoxide): δ-61.6.

MS (m/z): 248[M]$^+$.

Example 49

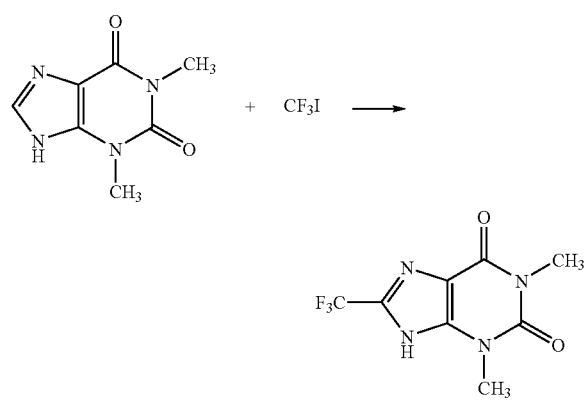

0.18 g (1.0 mmol) of theophylline was weighed and placed in a 50 ml two-neck flask equipped with a magnetic rotor and the atmosphere in the flask was replaced with argon. The following materials were added thereinto: 2.0 ml of dimethyl sulfoxide, 2.0 ml of a 1N dimethyl sulfoxide solution of sulfuric acid, 1.0 ml of a 3.0 mol/l dimethyl sulfoxide solution of trifluoromethyl iodide, 0.2 ml of a 30% hydrogen peroxide aqueous solution and 0.3 ml of a 1.0 mol/l aqueous solution of iron (II) sulfate. The mixture was stirred at 40 to 50° C. for 20 minutes and then the resulting solution was cooled to room temperature. Formation of 8-trifluoromethyltheophylline ($^{19}$F-NMR yield: 48%) was confirmed by $^{19}$F-NMR with 2,2,2-trifluoroethanol as an internal standard. 8-Trifluoromethyltheophylline was obtained as a white solid (0.086 g, yield: 35%) by column chromatography.

$^1$H-NMR (deuterated dimethyl sulfoxide): δ3.24 (s, 3H), 3.42 (s, 3H), 15.2 (brs, 1H).

$^{13}$C-NMR (deuterated dimethyl sulfoxide): δ27.9, 29.9, 109.1, 118.2 (q, $J_{CF}$=270.0 Hz), 137.3 (q, $J_{CF}$=37.2 Hz), 146.8, 150.9, 154.6.

$^{19}$F-NMR (deuterated dimethyl sulfoxide): δ-62.3.

MS (m/z): 248[M]$^+$.

Example 50

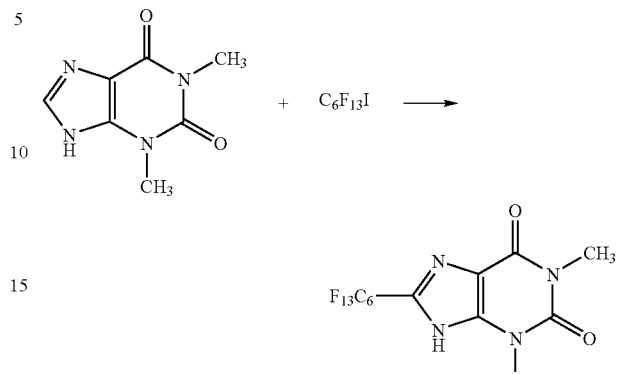

0.18 g (1.0 mmol) of theophylline was weighed and placed in a 50 ml two-neck flask equipped with a magnetic rotor and the atmosphere in the flask was replaced with argon. The following materials were added thereinto: 3.0 ml of dimethyl sulfoxide, 2.0 ml of a 1N dimethyl sulfoxide solution of sulfuric acid, 1.3 ml of tridecafluoro-1-iodohexane, 0.3 ml of a 1.0 mol/l aqueous solution of iron (II) sulfate and 0.2 ml of a 30% hydrogen peroxide aqueous solution. The mixture was stirred at 40 to 50° C. for 20 minutes and then the resulting solution was cooled to room temperature. Formation of 8-perfluorohexyltheophylline ($^{19}$F-NMR yield: 12%) was confirmed by $^{19}$F-NMR with 2,2,2-trifluoroethanol as an internal standard. 8-Perfluorohexyltheophylline was obtained as a white solid (0.02 g, yield: 4.0%) by column chromatography.

$^1$H-NMR (deuterated acetone): δ3.34 (s, 3H), 3.57 (s, 3H), 14.2 (brs, 1H).

$^{19}$F-NMR (deuterated acetone): δ-127.0 (m, 2F), -123.6 (brs, 2F), -122.9 (m, 2F), -122.4 (brs, 2F), -112.3 (m, 2F), -81.9 (t, $J_{FF}$=7.1 Hz, 3F).

MS (m/z): 499[M+H]$^+$.

Example 51

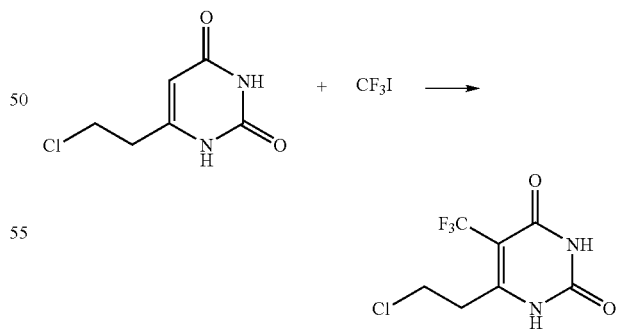

Formation of 6-(2-chloroethyl)-5-trifluoromethyluracil ($^{19}$F-NMR yield: 55%) was confirmed in the same manner as in Example 22, except that 0.16 g of 6-(2-chloroethyl)uracil was used instead of 0.37 g of 2',3',5'-tri-O-acetyluridine. Then 6-(2-chloroethyl)-5-trifluoromethyluracil was obtained as a white solid (0.10 g, yield: 45%) by preparative thin-layer chromatography.

INDUSTRIAL APPLICABILITY

The nucleobase having a perfluoroalkyl group according to the present invention is useful as a medical drug, an intermediate for preparing medical and agricultural chemicals, and so on.

The entire disclosure of Japanese Patent Application No. 2005-324943 filed on Nov. 9, 2005 including the specification, claims, and summary is incorporated herein by reference in its entirety.

The invention claimed is:

1. A process for producing a nucleobase having a perfluoroalkyl group, the process comprising: carrying out a reaction of a compound represented by the general formula (3):

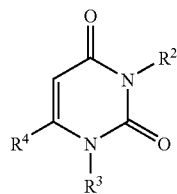

(3)

wherein $R^2$ is a hydrogen atom, an optionally substituted C1-C6 alkyl group or a protecting group for nitrogen, $R^3$ is a hydrogen atom, an optionally substituted C1-C6 alkyl group, a protecting group for nitrogen, or a pentose residue, and $R^4$ is a hydrogen atom, an optionally substituted C1-C6 alkyl group, an optionally substituted C1-C4 alkoxy group, an optionally substituted amino group, a carboxy group, an optionally substituted carbamoyl group, or an optionally substituted C2-C5 alkoxycarbonyl group; a compound represented by the general formula (4):

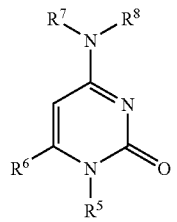

(4)

wherein $R^5$ is a hydrogen atom, an optionally substituted C1-C6 alkyl group, a protecting group for nitrogen, or a pentose residue, $R^6$ is a hydrogen atom, an optionally substituted C1-C6 alkyl group, an optionally substituted amino group, a carboxy group, an optionally substituted carbamoyl group, or an optionally substituted C2-C5 alkoxycarbonyl group, and each of $R^7$ and $R^8$ is a hydrogen atom or a protecting group for nitrogen; a compound represented by the general formula (5):

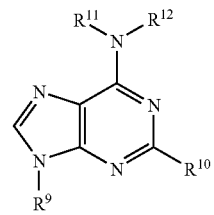

(5)

wherein $R^9$ is a hydrogen atom, an optionally substituted C1-C6 alkyl group, a protecting group for nitrogen, or a pentose residue, $R^{10}$ is a hydrogen atom, an optionally substituted C1-C6 alkyl group, an optionally substituted amino group, a carboxy group, an optionally substituted carbamoyl group, or an optionally substituted C2-C05 alkoxycarbonyl group, and each of $R^{11}$ and $R^{12}$ is a hydrogen atom or a protecting group for nitrogen; a compound represented by the general formula (6):

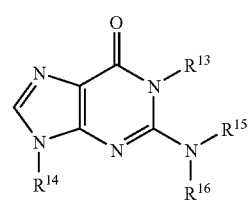

(6)

wherein $R^{13}$ is a hydrogen atom, an optionally substituted C1-C6 alkyl group or a protecting group for nitrogen, $R^{14}$ is a hydrogen atom, an optionally substituted C1-C6 group, a protecting group for nitrogen, or a pentose residue, and each of $R^{15}$ and $R^{16}$ is a hydrogen atom or a protecting group for nitrogen; a compound represented by the general formula (7):

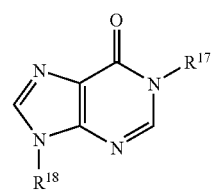

(7)

wherein $R^{17}$ is a hydrogen atom, an optionally substituted C1-C6 alkyl group or a protecting group for nitrogen, and $R^{18}$ is a hydrogen atom, an optionally substituted C1-C6 alkyl group, a protecting group for nitrogen, or a pentose residue; or a compound represented by the general formula (8):

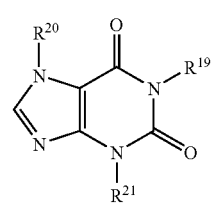

(8)

wherein $R^{19}$ is a hydrogen atom, an optionally substituted C1-C6 alkyl group or a protecting group for nitrogen, $R^{20}$ is a hydrogen atom, an optionally substituted C1-C6 alkyl group, a protecting group for nitrogen, or a pentose residue, and $R^{21}$ is a hydrogen atom, an optionally substituted C1-C6 alkyl group or a protecting group for nitrogen, with a perfluoroalkyl halide represented by the general formula (2):

$$Rf-X \qquad (2)$$

wherein Rf is a C1-C6 perfluoroalkyl group and X is a halogen atom, in the presence of a sulfoxide represented by the general formula (1):

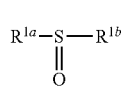
(1)

wherein each of $R^{1a}$ and $R^{1b}$ is a C1-C12 alkyl group or an optionally substituted phenyl group, and in the presence of a peroxide, an iron compound and an acid.

2. The process according to claim 1, wherein the compound is represented by the general formula (3).

3. The process according to claim 1, wherein X is iodo or bromo.

4. The process according to claim 1, wherein Rf is a trifluoromethyl group or a perfluoroethyl group.

5. The process according to claim 1, wherein the source of the iron compound is iron (II) sulfate, ammonium iron (II) sulfate, iron (II) tetrafluoroborate, iron (II) chloride, iron (II) bromide, iron (II) iodide, iron (II) acetate, iron (II) oxalate, bis(acetylacetonato)iron(II), ferrocene, bis($\eta^5$-pentamethylcyclopentadieny)iron or an iron powder.

6. The process according to claim 5, wherein the source of the iron compound is iron (II) sulfate, ammonium iron (II) sulfate, iron (II) tetrafluoroborate, ferrocene or an iron powder.

7. The process according to claim 1, wherein the peroxide is hydrogen peroxide, a hydrogen peroxide-urea composite, tert-butyl peroxide or peroxyacetic acid.

8. The process according to claim 7, wherein the peroxide is hydrogen peroxide or a hydrogen peroxide-urea composite.

9. The process according to claim 1, wherein the acid is sulfuric acid, hydrochloric acid, hydrogen bromide, hydrogen iodide, nitric acid, phosphoric acid, hexafluorophosphoric acid, tetrafluoroboric acid, formic acid, acetic acid, propionic acid, oxalic acid, p-toluenesulfonic acid, trifluoromethanesulfonic acid or trifluoroacetic acid.

10. The process according to claim 9, wherein the acid is sulfuric acid, tetrafluoroboric acid or trifluoromethanesulfonic acid.

11. The process according to claim 1, wherein each of $R^{1a}$ and $R^{1b}$ is a methyl group, a butyl group or a phenyl group.

12. The process according to claim 1, wherein a temperature of the reaction is from 20 to 100° C.

13. The process according to claim 1, wherein a pressure of the reaction is from the atmospheric pressure (0.1 MPa) to 1.0 MPa.

14. 5-Perfluoroalkyluracils represented by the general formula (9):

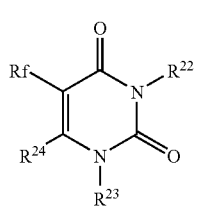
(9)

wherein Rf is a C1-C6 perfluoroalkyl group, each of $R^{22}$ and $R^{23}$ is a hydrogen atom or an optionally substituted C1-C6 alkyl group, and $R^{24}$ is an optionally substituted amino group or an optionally substituted C2-C5 alkoxycarbonyl group, provided that when both $R^{22}$ and $R^{23}$ are hydrogen atoms, $R^{24}$ is an optionally substituted C2-C5 alkoxycarbonyl group.

15. 8-Perfluoroalkylxanthines represented by the general formula (10):

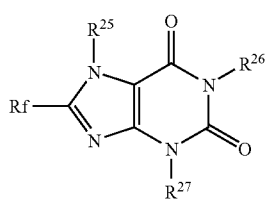
(10)

wherein Rf is a C1-C6 perfluoroalkyl group, and each of $R^{25}$, $R^{26}$ and $R^{27}$ is a hydrogen atom or an optionally substituted C1-C6 alkyl group, provided that $R^{25}$, $R^{26}$ and $R^{27}$ are not all hydrogen atoms.

* * * * *